United States Patent
Clement et al.

(10) Patent No.: US 11,718,845 B2
(45) Date of Patent: *Aug. 8, 2023

(54) METHODS FOR INCREASING GENE-EDITING FREQUENCIES IN MAIZE CELLS

(71) Applicant: INARI AGRICULTURE TECHNOLOGY, INC., Cambridge, MA (US)

(72) Inventors: Erik William Clement, Somerville, MA (US); Yajie Niu, Lexington (CN); Frank Anthony Skraly, Watertown, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 70 days.

This patent is subject to a terminal disclaimer.

(21) Appl. No.: 17/449,011

(22) Filed: Sep. 27, 2021

(65) Prior Publication Data
US 2022/0002706 A1    Jan. 6, 2022

Related U.S. Application Data

(63) Continuation of application No. 15/908,191, filed on Feb. 28, 2018, now Pat. No. 11,168,319.

(60) Provisional application No. 62/516,600, filed on Jun. 7, 2017, provisional application No. 62/464,991, filed on Feb. 28, 2017.

(51) Int. Cl.
| | | |
|---|---|---|
| *C12N 15/10* | (2006.01) | |
| *C12N 5/00* | (2006.01) | |
| *C12N 15/11* | (2006.01) | |
| *C12N 9/22* | (2006.01) | |

(52) U.S. Cl.
CPC ......... *C12N 15/102* (2013.01); *C12N 5/0025* (2013.01); *C12N 9/22* (2013.01); *C12N 15/11* (2013.01); *C12N 2310/20* (2017.05); *C12N 2500/02* (2013.01); *C12N 2500/14* (2013.01); *C12N 2500/16* (2013.01); *C12N 2800/80* (2013.01)

(58) Field of Classification Search
CPC .................. C12N 2500/02; C12N 2310/20
See application file for complete search history.

(56) References Cited

U.S. PATENT DOCUMENTS

| | | | |
|---|---|---|---|
| 8,106,258 B2 * | 1/2012 | Duncan | C12N 15/8207 800/278 |
| 11,168,319 B1 * | 11/2021 | Clement | C12N 15/8206 |
| 2015/0267189 A1 * | 9/2015 | Angel | A61P 1/02 435/468 |
| 2016/0355838 A1 * | 12/2016 | Septiningsih | C12N 9/16 |
| 2019/0211344 A1 | 7/2019 | Krieger et al. | |
| 2021/0363536 A1 | 11/2021 | Clement et al. | |

OTHER PUBLICATIONS

Gurushidze et al (Doubled Haploidy as a Tool for Chimaera Dissolution of TALEN-Induced Mutations in Barley. Biotechnologies for Plant Mutation Breeding pp. 129-141. Published online Dec. 2016). (Year: 2016).*
Xie et al (RNA-Guided Genome Editing in Plants Using a CRISPR-Cas System. Molecular Plant. vol. 6: 1975-1983, 2013). (Year: 2013).*
Lin et al (Enhanced homology-directed human genome engineering by controlled timing of CRISPR/Cas9 delivery ELife 1-13, 2014). (Year: 2014).*
Li et al (TALEN-Mediated Homologous Recombination Produces Site-Directed DNA Base Change and Herbicide-Resistant Rice. Journal of Genetics and Genomics 43. 297-305, 2016) (Year: 2016).*
Livanos et al (Plant cell division. ROS homeostasis is required. Plant Signaling & Behavior 7:7, 771-778; Jul. 2012). (Year: 2012).*
Zhou et al (Optimal ROS signaling is critical for nuclear reprogramming. Cell Rep. May 3; 15(5): 919-925, 2016). (Year: 2016).*
Blokhina et al (Antioxidants, Oxidative Damage and Oxygen Deprivation Stress: a Review. Annals of Botany 91:179-194, 2003) (Year: 2003).*
Dan, Yinghui, "Biological functions of antioxidants in plant transformation", In Vitro Cell Dev. Biol. Plant, vol. 44, pp. 149-161, 2008.
United States Patent and Trademark Office in connection with U.S. Appl. No. 16/963,372, filed Jul. 20, 2020, "Restriction Requirement", 8 pages, dated Feb. 4, 2022.

* cited by examiner

*Primary Examiner* — Charles Logsdon
*Assistant Examiner* — Wayne Zhong
(74) *Attorney, Agent, or Firm* — McKee, Voorhees & Sease, PLC

(57) ABSTRACT

Plant cell cultures as well as related methods, systems, and compositions for increasing the frequency and efficiency of plant genome editing are provided. Various plant cell growth conditions and/or treatments where such increases in gene editing frequencies are obtained are disclosed.

4 Claims, No Drawings
Specification includes a Sequence Listing.

METHODS FOR INCREASING GENE-EDITING FREQUENCIES IN MAIZE CELLS

FIELD

Aspects of this disclosure relate to agricultural biotechnology. Disclosed herein are methods useful in the culture and genomic editing of plants, plant parts, plant cells, and plant protoplasts.

INCORPORATION OF SEQUENCE LISTING

A sequence listing containing the file named "63200-172185_ST25.txt" which is 9,937 bytes (measured in MS-Windows®) and created on Feb. 27, 2018, comprises 17 nucleotide sequences, is provided herewith via the USPTO's EFS system and is herein incorporated by reference in its entirety.

BACKGROUND

Recent advances in genome editing technologies have provided opportunities for precise modification of the genome in many types of organisms, including plants and animals. For example, technologies based on genome editing proteins, such as zinc finger nucleases, TALENs, and CRISPR systems are advancing rapidly and it is now possible to target genetic changes to specific DNA sequences in the genome. Methods for growing and manipulating plant cells and plant protoplasts, including isolated cells and protoplasts, are especially useful for genome editing as well as genetic engineering technologies.

SUMMARY

Disclosed herein are methods of culturing plant cells or plant protoplasts having improved viability and/or increased gene-editing frequencies under cell culture conditions, valuable for use in plant tissue culture and plant biotechnology. Also disclosed are compositions derived from such plant cells or plant protoplasts having improved viability and/or increased gene-editing frequencies, such as novel plant cells or plant protoplasts, plant callus, plant tissues or parts, whole plants, and seeds having one or more altered genetic sequences. Further disclosed herein are plant cell cultures, methods, and systems that provide for increased plant gene-editing frequencies in plant cells, populations of plant cells with increased plant gene-editing frequencies, as well as for plant cells, plants, and plant parts with genome modifications.

In one aspect, the disclosure provides a plant cell or a plant protoplast culture including: (a) at least one plant cell or one plant protoplast; and (b) a culture medium including (i) a non-conventionally high concentration (such as at least 30, at least 40, at least 60, at least 80, or at least 100 millimolar) of a divalent cation, or (ii) an antioxidant, such as, but not limited to, a low-molecular-weight thiol antioxidant; or (iii) a combination of (i) and (ii). In an embodiment, the culture includes (a) at least one plant cell or one plant protoplast; and (b) a culture medium including: (i) at least 40 millimolar $Ca^{2+}$ or $Mg^{2+}$; (ii) an antioxidant; or (iii) a combination of (i) and (ii). Specific embodiments include plant protoplast cultures wherein the culture medium contains from between or about 40-100 millimolar $Ca^{2+}$ or $Mg^{2+}$ or 1 millimolar glutathione. Certain embodiments include plant cell cultures wherein the culture medium contains from 30, 40, 50, or 60 to 80, 100, 120, or 150 millimolar $Ca^{2+}$ and/or $Mg^{2+}$ and/or 0.1, 0.2, or 0.4 to 0.6, 0.8, 1, 1.2, 1.4, 1,6, 1.8, or millimolar of a low-molecular-weight anti-oxidant or low-molecular-weight thiol. The plant cell or plant protoplast is obtained from any plant part or tissue or callus, and from any monocot or dicot plant species of interest, for example, row crop plants, fruit-producing plants and trees, vegetables, trees, and ornamental plants including ornamental flowers, shrubs, trees, groundcovers, and turf grasses. In certain embodiments, the culture includes plant cells or plant protoplasts that are encapsulated or enclosed in a polymer or in a vesicle or liposome or other fluid compartment; in other embodiments the plant cells or plant protoplasts are not encapsulated. In many embodiments, the culture is in a liquid medium; in other embodiments, the culture is in a solid or semi-solid medium, or in a combination of liquid and solid or semi-solid media. In certain embodiments, the viability of the protoplasts in the culture is improved, e. g., by at least 10% after at least about one day of culture time, when compared to the viability of protoplasts in control cultures without (i) a relatively high concentration (such as at least 20 millimolar) of a divalent cation, or (ii) an antioxidant, such as, but not limited to, a low-molecular-weight thiol antioxidant; or (iii) a combination of (i) and (ii). In certain embodiments, the culture medium is maintained under hypoxic conditions, e. g., under about one-half normal atmospheric oxygen concentrations or less, for example, at between or about 5 to about 10%, or about 5 to about 10%, oxygen by volume. In certain embodiments, the cell division rate of the protoplasts is improved compared to that of protoplasts in control cultures without (i) a relatively high concentration (such as at least 20 millimolar) of a divalent cation, or (ii) an antioxidant, such as, but not limited to, a low-molecular-weight thiol antioxidant; or (iii) hypoxic conditions; or (iv) any combination of (i), (ii), and (iii).

In another embodiment, the disclosure provides a method of improving viability of a plant protoplast, including the step of including in the culture conditions of the protoplast (i) a relatively high concentration (such as at least 20 millimolar) of a divalent cation, or (ii) an antioxidant, such as, but not limited to, a low-molecular-weight thiol antioxidant; or (iii) a combination of (i) and (ii). In certain embodiments of the method, viability of a plant protoplast is improved by including in the protoplast culture medium at least one of: (a) at least 40 millimolar $Ca^{2+}$ or $Mg^{2+}$; and (b) at least 1 millimolar low-molecular-weight thiol. In certain embodiments of the method, viability of a plant protoplast is improved by including in the protoplast culture medium between or about 40-100 millimolar $Ca^{2+}$ or $Mg^{2+}$ or about 1 millimolar glutathione. In certain embodiments of the method, viability of a plant protoplast is improved, e. g., by at least 10% after at least about one day of culture time, when compared to the viability of protoplasts in control cultures without (i) a relatively high concentration (such as at least 20 millimolar) of a divalent cation, or (ii) an antioxidant, such as, but not limited to, a low-molecular-weight thiol antioxidant; or (iii) a combination of (i) and (ii). In certain embodiments of the method, the culture conditions further include use of hypoxic conditions, e. g., wherein the plant protoplasts are cultured under about one-half normal atmospheric oxygen concentrations or less, for example, at between or about 5 to about 10% oxygen by volume. In certain embodiments, the cell division rate of the protoplasts is improved compared to that of protoplasts in control cultures without (i) a relatively high concentration (such as at least 20 millimolar) of a divalent cation, or (ii)

an antioxidant, such as, but not limited to, a low-molecular-weight thiol antioxidant; or (iii) hypoxic conditions; or (iv) any combination of (i), (ii), and (iii). Related aspects of the disclosure include the protoplast having improved viability, increased gene-editing frequencies, and/or improved cell division rates, as provided by these methods, as well as living plant material (e.g., callus, a somatic embryo, plantlets, plants, seeds, or progeny plants of future generations) grown or regenerated from such a protoplast.

In another embodiment, the disclosure provides a method of improving the cell division rate of a plant cell or plant protoplast culture, wherein the culture conditions comprise hypoxic conditions, i.e., where the cells or protoplasts are grown at less than normal atmospheric oxygen conditions (less than about 21% oxygen by volume). In certain embodiments, plant cells or plant protoplasts are cultured at about one-half normal atmospheric oxygen conditions, or at about 10% oxygen by volume, or at about 5% oxygen by volume, or at between or about 5% to about 10% oxygen by volume, or between or about 1% to about 5% oxygen by volume, or between or about 1% to about 10% oxygen by volume. In certain embodiments, the culture conditions further comprise including in the culture medium a relatively high level of divalent cations, for example, at least 10 millimolar divalent cations (e.g., at least 40 millimolar $Ca^{2+}$ or $Mg^{2+}$). In certain embodiments, the culture conditions further comprise including in the culture medium an antioxidant, such as an antioxidant thiol (e.g., between or about at least about 0.1 to about 1 millimolar antioxidant thiol, or between or about at least about 0.5 to about 100 millimolar antioxidant thiol such as glutathione). In certain embodiments, the cell division rate of the plant cell or plant protoplast culture subjected to or grown under hypoxic conditions is improved by at least 10%, at least 15%, at least 25%, at least 50%, at least 75%, at least 100%, or by at least 2-fold, in comparison to a similar culture subjected to or grown under non-hypoxic conditions.

Protoplasts having improved viability, increased gene editing frequencies, and/or improved cell division rates as provided by the methods and culture conditions described herein are useful in plant tissue culture and plant biotechnology, e.g., in methods involving genetic engineering or genome editing. Thus, in another aspect, the disclosure provides a composition or plant cell culture including: (a) at least one plant cell or protoplast having improved viability and/or increased gene-editing frequencies, provided by including in the culture conditions of the protoplast (i) a relatively high concentration (such as at least 20 millimolar) of a divalent cation, or (ii) an antioxidant, such as, but not limited to, a low-molecular-weight thiol antioxidant; or (iii) hypoxic conditions; or (iv) any combination of (i), (ii), and (iii); (b) at least one effector molecule (e.g., a polynucleotide or a protein or a combination of both) for inducing a genetic alteration in the plant cell or plant protoplast; and (c) optionally, at least one delivery agent (such as at least one chemical, enzymatic, or physical agent). Certain embodiments include plant cell cultures or compositions comprising; (a) at least one plant cell or protoplast having improved viability and/or increased gene-editing frequencies provided by including in the culture conditions of the protoplast (i) a relatively high concentration (such as at least 20 millimolar) of a divalent cation, or (ii) an antioxidant, such as, but not limited to, a low-molecular-weight thiol antioxidant; or (iii) hypoxic conditions; or (iv) any combination of (i), (ii), and (iii); (b) gene editing molecules (e.g., (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA; (iv) one or more polynucleotide(s) encoding a sequence-specific endonuclease and a donor template polynucleotide; or (v) any combination thereof); and (c) optionally, at least one delivery agent (such as at least one chemical, enzymatic, or physical agent). Embodiments include compositions including at least one protoplast having improved viability and/or increased gene-editing frequencies and an RNA guide for an RNA-guided nuclease (or a polynucleotide encoding an RNA guide for an RNA-guided nuclease) and/or an RNA-guided DNA nuclease (or a polynucleotide encoding an RNA-guided DNA nuclease); optionally such compositions further include at least one chemical, enzymatic, or physical delivery agent. In a related aspect, the disclosure provides arrangements of protoplasts having improved viability and/or improved cell division rates as provided by the methods and culture conditions described herein, such as arrangements of protoplasts convenient for screening purposes. In an aspect, the disclosure provides an array including a plurality of containers, each including at least one protoplast having improved viability, increased gene-editing frequencies, and/or improved cell division rates, provided by including in the culture conditions of the protoplast (i) a relatively high concentration (such as at least 20 millimolar) of a divalent cation, or (ii) an antioxidant, such as, but not limited to, a low-molecular-weight thiol antioxidant; or (iii) hypoxic conditions; or (iv) any combination of (i), (ii), and (iii). In certain embodiments, the disclosure provides compositions comprising: (a) at least one plant cell or plant protoplast having improved viability and/or increased gene-editing frequencies; (b) at least one effector molecule for inducing a genetic alteration in the plant cell or plant protoplast, wherein the at least one effector molecule is selected from the group consisting of: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; (iii) a polynucleotide encoding one or more of any aforementioned or other nuclease capable of effecting site-specific alteration of a target nucleotide sequence; and/or (iv) at least one donor template polynucleotide; (c) at least one of: (i) at least 40 millimolar $Ca^{2+}$ or $Mg^{2+}$; and/or (ii) at least 1 millimolar low-molecular-weight thiol, and; (e) optionally, at least one delivery agent selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; and antioxidants; particles or nanoparticles, magnetic particles or nanoparticles, abrasive or scarifying agents, needles or microneedles, matrices, grids, and combinations thereof. In certain embodiments of any of the aforementioned compositions or plant cell cultures, the genome editing molecule(s) comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA; (iv) one or more polynucleotide(s) encoding a sequence-specific endonuclease and a donor template polynucleotide; or (v) any combination thereof.

Methods are provided for making a plant cell having a genomic modification comprising: (a) providing genome editing molecules to a plant cell previously, concurrently, or subsequently exposed to a hypoxic condition, a reactive oxygen species (ROS) concentration lowering agent, or combination thereof; wherein the molecules comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) a polynucleotide encoding a sequence-specific endonuclease and a donor template polynucleotide; or (v) any combination thereof, to modify the plant cell's genome; and, (b) isolating or propagating a plant cell comprising the genome modification. In certain embodiments, the methods further comprise obtaining callus, a propagule, or a plant from the isolated or propagated plant cell of step (b) comprising the genome modification, wherein the callus, propagule, or plant comprises a genome modified by the molecule(s) and wherein the propagule is optionally a seed.

Methods are provided for producing a plant having a genomic modification comprising: (a) providing genome editing molecules to a plant cell previously, concurrently, or subsequently exposed to a hypoxic condition, a reactive oxygen species (ROS) concentration lowering agent, or combination thereof, wherein the molecules comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) a polynucleotide encoding a sequence-specific endonuclease and a donor template polynucleotide; or (v) any combination thereof, to modify the plant cell's genome; (b) isolating or propagating a plant cell comprising the genome modification; and, (c) regenerating or obtaining a plant comprising the genome modification from the plant cell. In certain embodiments, the methods further comprise harvesting seed from the plant, propagating the plant, or multiplying the plant.

Systems are provided for producing a plant cell having a genomic modification comprising: (a) a plant cell subjected to a hypoxic condition, or treated with a reactive oxygen species (ROS) scavenging agent, or both subjected to the hypoxic condition and treated with the ROS scavenging agent; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein said plant cell is associated with, contacts, and/or contains said molecule(s).

Systems are provided for producing a plant cell having a genomic modification comprising: (a) a plant cell wherein a reactive oxygen species (ROS) concentration is lowered in comparison to a control plant cell; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein said plant cell is associated with, contacts, and/or contains said molecule(s).

Compositions are provided that comprise: (a) a plant cell wherein a reactive oxygen species (ROS) concentration is lowered in comparison to a control plant cell; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein said plant cell is associated with, contacts, and/or contains said agent and said molecule(s).

Plant cell cultures are provided that comprise: (a) a plant cell culture medium; (b) a plant cell exposed to a hypoxic condition, or to a reactive oxygen species (ROS) concentration lowering agent, or to a combination thereof, wherein the plant cell is contained or supported by the plant cell culture medium; and, (c) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the molecule(s).

Methods are provided for making a plant cell having a genomic modification that comprise: (a) providing genome editing molecules to a plant cell previously, concurrently, or subsequently subjected to a hypoxic condition, or to a reactive oxygen species (ROS) concentration lowering agent, or to a combination thereof; wherein the molecules comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) a polynucleotide encoding a sequence-specific endonuclease and a donor template polynucleotide; or (v) any combination thereof, to modify the plant cell's genome; and, (b) isolating, selecting, identifying, and/or propagating a plant cell comprising the genome modification, thereby making the plant cell having a genomic modification. In certain embodiments, the methods can further comprise obtaining callus, a propagule, or a plant from the isolated, selected, identified, and/or propagated plant cell of step (b) comprising the genome modification, wherein the callus, propagule, or plant comprises a genome modified by the molecule(s) and wherein the propagule is optionally a seed.

Systems are provided for producing a plant cell having a genomic modification comprising: (a) a plant cell subjected to a hypoxic condition, or treated with a reactive oxygen species (ROS) scavenging agent, or both subjected to the hypoxic condition and treated with the ROS scavenging agent; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the molecule(s).

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate embodiments and aspects of the disclosure described by the plural of that term.

The term "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "gene-editing" includes genome modification by homology directed repair (HDR) mechanisms. Such gene-editing includes embodiments where a site specific nuclease and a donor template are provided.

As used herein, the terms "expose" or "exposed" and the like are synonymous with the terms "subject" or "subjected" and the like.

As used herein, an "exogenous" agent or molecule refers to any agent or molecule from an external source that is provided to or introduced into a system, composition, plant cell culture, reaction system, or plant cell. In certain embodiments, the exogenous agent (e.g., polynucleotide, protein, or compound) from the external source can be an agent that is also found in a plant cell. In certain embodiments, the exogenous agent (e.g., polynucleotide, protein, or compound) from the external source can be an agent that is heterologous to the plant cell.

As used herein, a "heterologous" agent or molecule refers to any agent or molecule that is not found in a wild-type, untreated, or naturally occurring composition or plant cell; and/or (ii) to a polynucleotide or peptide sequence located in, e. g., a genome or a vector, in a context other than that in which the sequence occurs in nature. For example, a promoter that is operably linked to a gene other than the gene that the promoter is operably linked to in nature is a heterologous promoter.

As used herein, the terms "include," "includes," and "including" are to be construed as at least having the features to which they refer while not excluding any additional unspecified features.

As used herein, the phrases "low-molecular-weight antioxidant" or "low-molecule-weight thiol" respectively refer to antioxidant or thiol compounds having a molecular weight of less than about 1000.

As used herein, the phrase "plant cell" includes plant cells located within a plant, plant tissue, callus tissue, embryogenic callus, or plant part in an undissociated form, plant cells in a dissociated form or semi-dissociated form that have a cell wall or a portion of a cell wall, as well as plant protoplasts that lack a cell well in a dissociated or semi-dissociated form.

As used herein, the phrase "plant cell culture" refers to plant tissue, callus tissue, embryogenic callus, or plant part in an undissociated form, plant cells in a dissociated form or semi-dissociated form that have a cell wall or a portion of a cell wall, as well as plant protoplasts in a dissociated or semi-dissociated form that lack a cell well, wherein the plant tissue, callus tissue, embryogenic callus, plant part, plant cells or plant protoplasts are contained in or supported by a plant cell culture medium.

As used herein, the phrase "plant cell culture medium" refers to any of a liquid, solid, and/or gel that contains nutrients sufficient to support viability and/or growth of a plant cell maintained therein or thereon. Examples of plant cell culture medium include compositions comprising at least salts and vitamins that support plant viability and/or growth (e.g., Gamborg's B-5 Basal Medium, Murashige and Skoog Basal Medium (MS), Schenk and Hildebrandt Basal Salt Mixture, and the like).

By "polynucleotide" is meant a nucleic acid molecule containing 2 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Methods of using polynucleotides or compositions containing polynucleotides are provided herein. Embodiments of the methods and compositions provided herein can employ or include: one or more polynucleotides of 2 to 25 residues in length, one or more polynucleotides of more than 26 residues in length, or a mixture of both. Polynucleotides can comprise single- or double-stranded RNA, single- or double-stranded DNA, double-stranded DNA/RNA hybrids, chemically modified analogues thereof, or a mixture thereof. In certain embodiments, a polynucleotide includes a combination of ribonucleotides and deoxyribonucleotides (e. g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In certain embodiments, the polynucleotide includes chemically modified nucleotides (see, e. g., Verma and Eckstein (1998) *Annu. Rev. Biochem.*, 67:99-134). Chemically modified nucleotides that can be used in the polynucleotides provided herein include: (i) phosphorothioate, phosphorodithioate, or methylphosphonate internucleotide linkage modifications; (ii) modified nucleoside bases and/or modified sugars; (iii) detectable labels including a fluorescent moiety (e. g., fluorescein or rhodamine or a fluorescence resonance energy transfer or FRET pair of chromophore labels) or other label (e. g., biotin or an isotope). Polynucleotides provided or used herein also include modified nucleic acids, particularly modified RNAs, which are disclosed in U.S. Pat. No. 9,464,124, incorporated by reference in its entirety herein.

As used herein the term "synergistic" refers to an effect of combining at least two factors that exceeds the sum of the effects obtained when the factors are not combined.

As used herein, the phrase "target plant gene" refers to a gene located in the plant genome that is to be modified by gene editing molecules provided in a system, method, composition and/or plant cell provided herein. Embodiments of target plant genes include (protein-) coding sequence, non-coding sequence, and combinations of coding and non-coding sequences. Modifications of a target plant gene include nucleotide substitutions, insertions, and/or deletions in one or more elements of a plant gene that include a transcriptional enhancer or promoter, a 5' or 3' untranslated region, a mature or precursor RNA coding sequence, an exon, an intron, a splice donor and/or acceptor, a protein coding sequence, a polyadenylation site, and/or a transcriptional terminator. In certain embodiments, all copies or all alleles of a given target gene in a diploid or polyploid plant cell are modified to provide homozygosity of the modified target gene in the plant cell. In certain embodiments, where a desired trait is conferred by a loss-of-function mutation that is introduced into the target gene by gene editing, a plant cell, population of plant cells, plant, or seed is homozygous for a modified target gene with the loss-of-function mutation. In other embodiments, only a subset of the copies or alleles of a given target gene are modified to provide heterozygosity of the modified target gene in the plant cell. In certain embodiments where a desired trait is conferred by a dominant mutation that is introduced into the target gene by gene editing, a plant cell, population of plant cells, plant, or seed is heterozygous for a modified target gene with the dominant mutation. Traits imparted by such modifications to certain plant target genes include improved yield, resistance to insects, fungi, bacterial pathogens, and/or nematodes, herbicide tolerance, abiotic stress tolerance (e.g., drought, cold, salt, and/or heat tolerance), protein quantity and/or quality, starch quantity and/or quality, lipid quantity and/or quality, secondary metabolite quantity and/or quality, and the like, all in comparison to a control plant that lacks the modification.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Systems, methods, and compositions that provide for increased frequencies of plant gene editing in comparison to controls are provided herein. Such systems, methods and compositions can comprise a combination at least two features that provide for such increased plant gene editing frequencies. In certain embodiments, a first feature comprises plant cells that have been exposed to hypoxic conditions and/or agents that reduce reactive oxygen species (ROS) or plant cells that have lowered ROS concentrations. In certain embodiments, a second feature comprises treatment of the plant cells that have been exposed to hypoxic conditions and/or agents that reduce ROS or the plant cells that have lowered ROS concentrations with a non-conventionally high concentration of a divalent cation or divalent cation mixture.

In one aspect, the disclosure provides a plant cell or a plant protoplast culture including: (a) at least one plant cell or one plant protoplast; and (b) a culture medium including (i) a non-conventionally high concentration (such as at least 30, at least 40, at least 60, at least 80, or at least 100 millimolar) of a divalent cation or divalent cation mixture, or (ii) an antioxidant; or (iii) a combination of (i) and (ii). In an embodiment, the plant cell or a plant protoplast culture includes (a) at least one plant cell or one plant protoplast; and (b) a culture medium including: (i) at least 40 millimolar $Ca^{2+}$ or $Mg^{2+}$; (ii) about 0.1 to about 10 millimolar of a low-molecular-weight (non-enzymatic) antioxidant, such as, but not limited to, a low-molecular-weight thiol antioxidant; or (iii) a combination of (i) and (ii). Embodiments include plant cell or plant protoplast cultures wherein the culture medium contains:

(a) between about 40 to about 60 millimolar, or about 40 to about 60 millimolar, $Ca^{2+}$ and/or $Mg^{2+}$;
(b) between about 40 to about 80 millimolar, or about 40 to about 80 millimolar, $Ca^{2+}$ and/or $Mg^{2+}$;
(c) between about 40 to about 100 millimolar, or about 40 to about 100 millimolar, $Ca^{2+}$ and/or $Mg^{2+}$;
(d) between about 40 to about 150 millimolar, or about 40 to about 150 millimolar, $Ca^{2+}$ and/or $Mg^{2+}$;
(e) between about 60 to about 80 millimolar, or about 60 to about 80 millimolar, $Ca^{2+}$ and/or $Mg^{2+}$;
(f) between about 60 to about 100 millimolar, or about 60 to about 100 millimolar, $Ca^{2+}$ and/or $Mg^{2+}$;
(g) between about 60 to about 150 millimolar, or about 60 to about 150 millimolar, $Ca^{2+}$ and/or $Mg^{2+}$;
(h) between about 80 to about 100 millimolar, or about 80 to about 100 millimolar, $Ca^{2+}$ and/or $Mg^{2+}$;
(i) between about 80 to about 150 millimolar, or about 80 to about 150 millimolar, $Ca^{2+}$ and/or $Mg^{2+}$;
(j) between about 0.1 to about 1 millimolar, or about 0.1 to about 1 millimolar, low-molecular-weight antioxidant;
(k) between about 1 to about 10 millimolar, or about 1 to about 10 millimolar, low-molecular-weight antioxidant;
(l) between about 0.1 to about 1 millimolar, or about 0.1 to about 1 millimolar, low-molecular-weight thiol (e. g., glutathione, cysteine, cysteinyl glycine, gamma-glutamyl cysteine, N-acetylcysteine, cysteine, thiocysteine, homocysteine, lipoic acid, and dithiothreitol); and/or
(m) between about 1 to about 10 millimolar, or about 1 to about 10 millimolar, low-molecular-weight thiol (e. g., glutathione, cysteine, cysteinyl glycine, gamma-glutamyl cysteine, N-acetylcysteine, cysteine, thiocysteine, homocysteine, lipoic acid, and dithiothreitol).

Embodiments of the methods, systems, or compositions provided herein include plant cell cultures having any of the aforementioned divalent cation and/or antioxidants set forth in (a), (b), (c), (d), (e), (f), (g), (h), (i), (j), and/or (k).

Embodiments of the systems, methods, or compositions provided herein include cultures, plants, and/or plant parts wherein the plant cell is exposed or treated with an enzymatic and/or a non-enzymatic ROS scavenging agent. In certain embodiments, such exposure or treatment with the enzymatic and/or a non-enzymatic ROS scavenging agent results in lowered concentrations of ROS (e.g., hydrogen peroxide, a superoxide radical, a peroxide ion, a hydroperoxyl radical, and/or a hydroxyl radical) in the exposed or treated plant cell in comparison to an unexposed or untreated plant cell. In certain embodiments, the non-enzymatic ROS scavenging agents include low-molecular-weight antioxidants, including lipid-soluble antioxidants and water-soluble antioxidants (e.g., low-molecular-weight thiol antioxidants, pro-thiols, ascorbic acid, tocopherols, carotenoids, flavonoids, butylated hydroxytoluene, and butylated hydroxyanisole). In certain embodiments, the non-enzymatic ROS scavenging agents are provided at a concentration of about 0.1 to about 10 millimolar. Specific embodiments include cultures wherein the culture medium includes about 0.1 to about 10 millimolar low-molecular-weight thiol antioxidants. Low-molecular-weight thiol antioxidants useful in the systems, methods, and compositions include glutathione (gamma-glutamylcysteinyl glycine), cysteine, cysteinyl glycine, gamma-glutamyl cysteine, N-acetylcysteine, cysteine, thiocysteine, homocysteine, lipoic acid, and/or dithiothreitol (any of which can also be used in combination with each other at a similar final thiol concentration). ROS scavenging agents useful in the systems, methods, and compositions also include pro-thiols (e.g., L-2-oxothiazolidine-4-carboxylate (OTC)) which are converted to thiols in the cell. In certain embodiments, the plant cell is exposed or treated with enzymatic ROS scavenging agents. Enzymatic ROS scavenging agents include any catalase, ascorbate peroxidase, a dehydroascorbate reductase, guaiacol peroxidase, monodehydroascorbate reductase, a peroxidase, and/or superoxide dismutase. In certain embodiments, an enzymatic ROS scavenging agents is provided in the culture medium. In certain embodiments, an enzymatic ROS scavenging agent or polynucleotides encoding the same can be introduced into the plant cell (e.g., by transient or stable transformation, transfection, or with a delivery agent). A combination of at least one enzymatic and at least one non-enzymatic ROS scavenging agent can also be used. Specific embodiments also include plant cell or plant protoplast cultures wherein the culture medium includes about 20, about 40, or about 60 to about 80, about 100, about 120, or about 150 millimolar $Ca^{2+}$ and/or $Mg^{2+}$ and/or in which the culture medium includes about 0.1, about 0.25, about 0.5, about 0.75, about 1, or about 2 to about 4, about 6, about 8, or about 10 millimolar low-molecular-weight thiol antioxidant. Further embodiments encompassed are plant cell or plant protoplast cultures wherein the culture medium includes combinations of divalent cations and low-molecular-weight antioxidants, with the individual components present in the culture at concentrations similar to those listed above. In certain embodiments, the plant cells (e.g., plant protoplasts) are exposed to the ROS scavenging agents about 5, 10, 15, 30, or 45 minutes to about 60, 75, 90, or 120 minutes after exposure to the gene-editing molecules. In certain embodiments, the plant cells (e.g., plant protoplasts) are exposed to the ROS scavenging agents prior to or at the same time that they are exposed to the gene-editing molecules.

Embodiments of the methods, systems, or compositions provided herein also include plant cell or plant protoplast cultures wherein the culture medium includes at least 40 millimolar $Ca^{2+}$, or at least 50 millimolar $Ca^{2+}$, or at least 100 millimolar $Ca^{2+}$. Embodiments include plant cell or plant protoplast cultures wherein the culture medium includes at least 40 millimolar $Mg^{2+}$, or at least 50 millimolar $Mg^{2+}$, or at least 100 millimolar $Mg^{2+}$. Embodiments include plant cell or plant protoplast cultures wherein the culture medium includes between or about 0.1 to about 10 millimolar low-molecular-weight antioxidants, including lipid-soluble antioxidants and water-soluble antioxidants, for example, low-molecular-weight thiol antioxidants, ascorbic acid, tocopherols, butylated hydroxytoluene, and butylated hydroxyanisole. Specific embodiments include plant cell or plant protoplast cultures wherein the culture medium includes between about 0.1 to about 10 millimolar low-molecular-weight thiol antioxidants see, e. g., Pivato et al. (2014) *Archives Biochem. Biophys.*, 560:83-99. Low-molecular-weight thiol antioxidants useful in compositions and methods provided herein include, but are not limited to, glutathione (gamma-glutamylcysteinyl glycine), cysteine, cysteinyl glycine, gamma-glutamyl cysteine, N-acetylcysteine, cysteine, thiocysteine, homocysteine, lipoic acid, and dithiothreitol (any of which can also be used in combination with each other at a similar final thiol concentration). Specific embodiments include plant cell or plant protoplast cultures wherein the culture medium includes about 20, about 40, about 60, about 80, about 100, about 120, or about 150 millimolar $Ca^{2+}$, or in which the culture medium includes about 0.1, about 0.25, about 0.5, about 0.75, about 1, about 2, about 4, about 6, about 8, or about 10 millimolar low-molecular-weight thiol antioxidant. Further embodiments encompassed are plant cell or plant protoplast cultures wherein the culture medium includes combinations of divalent cations and low-molecular-weight antioxidants or low-molecular-weight thiols, with the individual components present in the culture at concentrations similar to those listed above.

In certain embodiments of the methods, systems, and compositions provided herein, the culture medium is maintained under hypoxic conditions, e. g., under about one-half normal atmospheric oxygen concentrations or less, for example, at between or about 5 to about 10% oxygen by volume. Normal (i.e., "normoxic") oxygen conditions comprise about 21% oxygen by volume. Hypoxic conditions used in the systems, methods, and compositions provided herein can in certain embodiments comprise about 14%, 13%, 12%, 11%, or 10% to about 8%, 7%, 6%, or 5% oxygen by volume. In certain embodiments, hypoxic conditions can comprise treating the plant cells with a hypoxia mimetic (e.g., desferrioxamine or cobalt chloride). In certain embodiments, a hypoxic condition can comprises maintaining the cell in a liquid culture media having a dissolved oxygen concentration that is lower than the dissolved oxygen concentration obtained when the liquid culture media is under normoxic conditions. Such exposure of the plant cell to the hypoxic condition can in certain embodiments be limited to a period of time necessary to realize improvements in gene editing frequencies (e.g., prior to and/or during association, contact, and/or containment to/of an ROS lowering agent and/or gene editing molecule; prior to and/or during exposure and/or after to an ROS lowering agent and/or gene editing molecule). Such exposure and or maintenance of a plant cell under hypoxic conditions can be achieved in the context of a plant cell in isolated form (e.g., as a protoplast), a plant cell in a plant embryo, plant callus, especially embryogenic callus, in an isolated plant tissue or part (e.g., an ovule, anther, leaf, meristematic tissue, and the like), or in a whole plant. In certain embodiments, the plant cell in any of the aforementioned contexts can be in a liquid or solid culture medium that includes about 20, about 40, or about 60 to about 80, about 100, about 120, or about 150 millimolar $Ca^{2+}$ and/or $Mg^{2+}$, and is exposed to and/or maintained under hypoxic conditions. In certain embodiments, the plant cells (e.g., plant protoplasts) are exposed to the hypoxic conditions about 5, 10, 15, 30, or 45 minutes to about 60, 75, 90, or 120 minutes after exposure to the gene-editing molecules and/or ROS lowering agent In certain embodiments, the culture medium includes about 20, about 40, about 60, about 80, about 100, about 120, or about 150 millimolar $Ca^{2+}$ or $Mg^{2+}$, and is maintained under hypoxic conditions. In certain embodiments, the culture medium includes between or about 40 to about 150 millimolar $Ca^{2+}$, and is maintained between or about 5 to about 10% oxygen by volume. In certain embodiments, the cell division rate of the protoplasts is improved compared to that of protoplasts in control cultures without (i) a relatively high concentration (such as at least 20 millimolar) of a divalent cation, or (ii) an antioxidant, such as, but not limited to, a low-molecular-weight thiol antioxidant; or (iii) hypoxic conditions; or (iv) any combination of (i), (ii), and (iii). In certain embodiments, the cell division rate of the plant cells or plant protoplasts is improved by at least 20%, or by at least 50%, or by at least 75%, or by at least 100%. In an embodiment, the culture conditions include at least 40 millimolar $Ca^{2+}$ and about one-half normal atmospheric oxygen concentrations, and the cell division rate of the plant cells or plant protoplasts is improved by at least 100% (i. e., cell division rate is about twice that observed in similar cultures grown under or subjected to normal atmospheric oxygen concentrations).

In certain embodiments, the plant cell or plant protoplast cultures are exposed to the aforementioned culture media immediately after introduction of a gene editing molecule. In certain embodiments, the plant cell or plant protoplast cultures are exposed to the aforementioned culture media during the time that they are treated with a gene editing molecule and immediately afterwards. In certain embodiments, the plant cell or plant protoplast cultures are exposed to the aforementioned culture media before and/or during the time that they are treated with a gene editing molecule and/or immediately afterwards. Exposure of the plant cell or plant protoplast cultures to the culture media can be for about 1, 2, 4, 6, or 8 to about 12, 18, 24, 36, or 48 hours after introduction of a gene editing molecule. Gene editing molecules can be introduced by methods that include transfection, *Agrobacterium*-mediated transformation, Agro-infection, electroporation, and the like. In certain embodiments, the plant cell or plant protoplast is maintained at a temperature of about 30° C., 32° C., 34° C., or 36° C. to about 38° C., 40° C., or 42° C. for at least about 30, 40, 50, or 60 minutes, or for about 30, 40, 50, 60, to about 70, 80, 90, or 120 minutes, following introduction of the gene editing molecules.

In certain embodiments, plant cells or plant protoplasts in the culture system, method, composition or reaction mixtures provided herein are generally isolated plant cells or plant protoplasts, that is to say, not located in undissociated or intact plant tissues, plant parts, or whole plants. In certain embodiments, the culture includes plant cells or plant protoplasts obtained from any part or tissue or callus. In certain embodiments, the culture includes plant cells or plant protoplasts obtained from a plant tissue, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, ovule, pollen, microspore, anther, hypocotyl, cotyledon, leaf, petiole, stem, tuber, root, callus, or plant cell suspension.

In certain embodiments, plant cells in the system, method, composition or reaction mixtures provided herein are plant cells that are located in undissociated or intact plant tissues, plant parts, or whole plants. In certain embodiments, the plant cell can be located in an intact nodal bud, shoot apex or shoot apical meristem, root apex or root apical meristem, lateral meristem, intercalary meristem, seedling, whole seed, halved seed or other seed fragment, zygotic embryo, somatic embryo, ovule, pollen, microspore, anther, hypocotyl, cotyledon, leaf, petiole, stem, tuber, root, or callus.

In embodiments, the culture includes haploid, diploid, or polyploid plant cells or plant protoplasts, for example, those obtained from a haploid, diploid, or polyploid plant, plant part or tissue, or callus. In certain embodiments, the plant cells or plant protoplasts in the culture (or a regenerated plant, progeny seed, and progeny plant obtained from the plant cells or protoplasts) are haploid or can be induced to become haploid; techniques for making and using haploid plants and plant cells are known in the art, see, e. g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; Ravi et al. (2014) *Nature Communications*, 5:5334, doi: 10.1038/ncomms6334). Haploids can also be obtained in a wide variety of monocot plants (e.g., maize, wheat, rice, sorghum, barley) or dicot plants (e.g., soybean, *Brassica* sp. including canola, cotton, tomato) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e. g., from flowers, developing flowers or flower buds, ovaries, ovules, megaspores, anthers, pollen, and microspores. In certain embodiments where the plant cell or plant protoplast is haploid, the genetic complement can be doubled by chromosome doubling (e. g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another aspect of the disclosure is related to a hybrid plant having at least one parent plant that is a doubled haploid plant provided by this approach. Production of doubled haploid plants provides homozygosity in one generation, instead of requiring several generations of self-crossing to obtain homozygous plants; this may be particularly advantageous in slow-growing plants, such as fruit and other trees, or for producing hybrid plants that are offspring of at least one doubled-haploid plant.

In certain embodiments of the methods or systems provided herein, a plant cell or protoplast containing a genomic modification or a composition or plant cell culture comprising the plant cell or protoplast containing a genomic modification, can be used to obtain callus tissue, a propagule, or a plant containing the genomic modification. In certain embodiments, a propagule or plant is obtained by subjecting the plant cell or protoplast to culture systems comprising suitable amounts of plant nutrients, vitamins, phytohormones, and the like that result in regeneration of the propagule or plant. Conditions for induction of callus and regeneration of plants and propagules from plant cells and protoplasts of a variety of plant species disclosed in the patent literature (US20170145430; US20090038025; US20140173780; each of which are specifically incorporated herein by reference in their entireties) and non-patent literature (e.g., S Roest, L J W Gilissen, 1989, Acta botanica neerlandica, 38(1):1-23; Bhaskaran and Smith, Crop Sci. 30(6):1328-1337; Ikeuchi et al., Development, 2016, 143: 1442-1451) can be adapted for use obtaining callus, plant propagules, and plants from the plant cells and protoplasts disclosed herein. Propagules that can be obtained include buds, bulbs, corms, rhizomes, stolons, shoots, roots, stems, tubers, or cuttings thereof; as well as seeds, pollen, megaspores, and the like.

In embodiments, the culture, methods, systems, and/or compositions provided herein includes plant cells or plant protoplasts obtained from or located in any monocot or dicot plant species of interest, for example, row crop plants, fruit-producing plants and trees, vegetables, trees, and ornamental plants including ornamental flowers, shrubs, trees, groundcovers, and turf grasses. In certain embodiments, the culture, methods, systems, and/or compositions provided herein includes plant cells or plant protoplasts obtained from alfalfa (*Medicago sativa*), almonds (*Prunus dulcis*), apples (*Malus×domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus×paradisi*), grapes (*Vitus* spp.) including wine grapes (*Vitus vinifera*), guava (*Psidium guajava*), hemp and *cannabis* (e.g., *Cannabis sativa* and *Cannabis* spp.), hops (*Humulus lupulus*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), *papaya* (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria×ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), or yams (*Discorea* spp.). In certain embodiments, the culture, methods, systems, and/or compositions provided herein includes plant cells or plant protoplasts obtained from plants that are typically propagated through asexual means, e.g., apples (*Malus×domestica*), apricots (*Prunus armeniaca, P. brigantine, P. mandshurica, P. mume, P. sibirica*), avocado (*Persea americana*), bananas (*Musa* spp.), cherry (*Prunus avium*), grapefruit (*Citrus×paradisi*), grapes (*Vitus* spp.) including wine grapes (*Vitus vinifera*), irises (*Iris* spp.), lemon (*Citrus limon*), limes (*Citrus* spp.), orange (*Citrus sinensis*), peaches and nectarines (*Prunus persica*), pear (*Pyrus* spp.), pineapple (*Ananas comosus*), plantains (*Musa* spp.), plum (*Prunus domestica*), poinsettia (*Euphorbia pulcherrima*), potato (*Solanum tuberosum*), roses (*Rosa* spp.), strawberries (*Fragaria* spp., *Fragaria×ananassa*), sugarcanes (*Saccharum* spp.), sweet potato (*Ipomoea batatas*), tangerine (*Citrus tangerina*), tea (*Camellia sinensis*), yams (*Discorea* spp.), hops (*Humulus lupulus*), and hemp and *cannabis* (*Cannabis sativa* and *Cannabis* spp.) and many other plants and crops that form bulbs, bulbils, tubers, or corms, or which may be propagated by cuttings, root divisions, stolons, runners, or pups.

In embodiments, the culture, methods, systems, compositions, or reaction mixtures provided herein can include plant cells or plant protoplasts that are (a) encapsulated or enclosed in or attached to a polymer (e. g., pectin, agarose, or other polysaccharide) or other support (solid or semi-solid surfaces or matrices, or particles or nanoparticles); (b) encapsulated or enclosed in or attached to a vesicle or liposome or other fluid compartment; or (c) not encapsulated or enclosed or attached. In certain embodiments, the culture includes plant cells or plant protoplasts in liquid or suspension culture, or cultured in or on semi-solid or solid media, or in a combination of liquid and solid or semi-solid media (e. g., plant cells or protoplasts cultured on solid medium with a liquid medium overlay, or plant cells or protoplasts attached to solid beads or a matrix and grown with a liquid medium). In certain embodiments, the culture includes plant cells or plant protoplasts encapsulated in a polymer (e. g., pectin, agarose, or other polysaccharide) or other encapsulating material, enclosed in a vesicle or liposome, suspended in a mixed-phase medium (such as an emulsion or reverse emulsion), or embedded in or attached to a matrix or other solid support (e. g., beads or microbeads, membranes, or solid surfaces).

Viability of plant cells or plant protoplasts in a culture, method, or system provided herein can be determined by various staining techniques, e. g., by staining dead cells or protoplasts with Evans blue, bromophenol blue, methylene blue, or phenosafranin or staining live cells or protoplasts with fluorescein diacetate. Visual examination of unstained samples usually correlates well with staining results; live/intact protoplasts retain their round shape and appear to have good turgor pressure, while dead protoplasts are irregularly shaped, smaller, and appear shriveled. In certain embodiments, in addition to increased cell viability, culture conditions further provide an improved cell division rate; this can also be observed by, e. g., microscopic observations or flow cytometric analysis. Viability of cells or protoplasts in a culture can be expressed as a percentage, i.e., the percentage of living or viable cells or protoplasts relative to the total number of cells or protoplasts in a sample of the culture; viability can further be measured over a time-course and compared among different culture conditions. In certain embodiments, the viability of the protoplasts in the culture is improved, e. g., by at least 10% after at least about one day of culture time, when compared to the viability of protoplasts in control cultures without (i) a relatively high concentration (such as at least 20 millimolar) of a divalent cation, or (ii) an antioxidant, such as, but not limited to, a low-molecular-weight thiol antioxidant; or (iii) a combination of (i) and (ii); in certain embodiments, the viability of the protoplasts in the culture is improved by at least 10%, or by at least 15%, or by at least 20%, or by at least 25% after at least about one day of culture time, when compared to the viability of protoplasts in control cultures. In specific embodiments, the viability of the protoplasts in the culture, when compared to a control plant protoplast culture without (i) at least 40 millimolar Ca' or $Mg^{2+}$; (ii) an antioxidant; or (iii) a combination of (i) and (ii), is:

(a) at least 10% higher after 30 hours' culture;
(b) at least 10% higher after 48 hours' culture;
(c) at least 10% higher after 72 hours' culture; or
(d) at least 10% higher after 96 hours' culture.

In a specific embodiment, the culture includes at least one plant cell or plant protoplast obtained from maize, the culture medium includes at least 40, 60, 80, or 100 millimolar $Ca^{2+}$, and protoplast viability is at least 20% higher after 64 hours' culture when compared to a control plant protoplast culture without at least 40, 60, 80, or 100 millimolar $Ca^{2+}$. In a specific embodiment, the culture includes at least one plant cell or plant protoplast obtained from maize, the culture medium includes at least 1 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these), and protoplast viability is at least 10% higher after 64 hours' culture when compared to a control plant protoplast culture without at least 100 millimolar $Ca^{2+}$.

In another aspect, the disclosure provides a method of improving viability of a plant cell or a plant protoplast in culture, wherein the method comprises including in the culture conditions (i. e., in at least one medium used in culture) of the plant cell or plant protoplast: (i) a nonconventionally high concentration (such as at least 30, at least 40, at least 60, at least 80, or at least 100 millimolar) of a divalent cation (e.g., $Ca^{2+}$ and/or $Mg^{2+}$), or (ii) an antioxidant; or (iii) a combination of (i) and (ii). In an embodiment, the method comprises including in the culture conditions of the plant cell or plant protoplast at least one of: (i) about 40 to about 150 millimolar $Ca^{2+}$ and/or $Mg^{2+}$; and (ii) about 0.1 to about 10 millimolar low-molecular-weight (non-enzymatic) antioxidant, including lipid-soluble antioxidants and water-soluble antioxidants, for example, low-molecular-weight thiol antioxidants, ascorbic acid, tocopherols, butylated hydroxytoluene, and butylated hydroxyanisole. In an embodiment, the method comprises including in the culture conditions of the plant cell or plant protoplast at least one of: (i) at least 40 millimolar $Ca^{2+}$ and/or $Mg^{2+}$; and (ii) about 0.1 to about 10 millimolar low-molecular-weight antioxidant, such as, but not limited to, a low-molecular-weight thiol antioxidant. In an embodiment, the method comprises including in the culture conditions of the plant cell or plant protoplast at least one of (i) at least 40 millimolar $Ca^{2+}$ and/or $Mg^{2+}$; and (ii) at least 1 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these). In some embodiments, the method comprises culture conditions that further include hypoxia, or oxygen concentrations that are less than normal atmospheric concentrations, for example, about one-half normal atmospheric oxygen concentrations or about 5% to about 10% oxygen by volume. In certain embodiments, such conditions additionally result in an improved cell division rate in the culture. In certain embodiments, the culture conditions include at least 40 millimolar $Ca^{2+}$ and/or $Mg^{2+}$ in the medium and further include maintaining the culture under hypoxic conditions (e.g., about 5% to about 10% oxygen by volume). In certain embodiments, the cell division rate of the plant cells or plant protoplasts is improved by at least 20%, or by at least 50%, or by at least 75%, or by at least 100%. In an embodiment, the culture conditions include at least 40 millimolar $Ca^{2+}$ and about one-half normal atmospheric oxygen concentrations or about 5% to about 10% oxygen by volume, and the cell division rate of the plant cells or plant protoplasts is improved by at least 100% (i. e., cell division rate is about twice that observed in similar cultures grown under or subjected to normal atmospheric oxygen concentrations).

In embodiments, the method improves the viability of a plant cell or plant protoplast by at least 10% after at least about one day of culture time, when compared to the viability of plant cells or plant protoplasts in control cultures without (i) a relatively high concentration (such as at least 20 millimolar) of a divalent cation, or (ii) an antioxidant, such as, but not limited to, a low-molecular-weight thiol antioxidant; or (iii) a combination of (i) and (ii); in certain embodiments, the method improves the viability of the plant cells or plant protoplasts in the culture by at least 10%, or by at least 15%, or by at least 20%, or by at least 25% after at least about one day of culture time, when compared to the viability of plant cells or plant protoplasts in control cultures.

In specific embodiments, the method comprises including in the culture conditions of the plant cell or plant protoplast at least one of: (i) between or about 40 to about 150 millimolar $Ca^{2+}$ and/or $Mg^{2+}$; and (ii) between or about 0.1 to about 10 millimolar low-molecular-weight antioxidant; or (iii) a combination of (i) and (ii), whereby viability of the plant cells or plant protoplasts in the culture is improved by at least 10%, or by at least 15%, or by at least 20%, or by at least 25% after at least about one day of culture time, when compared to plant cells or plant protoplasts in a control culture without: (i) between or about 40 to about 150 millimolar $Ca^{2+}$ or $Mg^{2+}$; (ii) between or about 0.1 to about 10 millimolar low-molecular-weight antioxidant; or (iii) a combination of (i) and (ii). In specific embodiments, the method comprises including in the culture conditions of the plant cell or plant protoplast at least one of: (i) at least 40 millimolar $Ca^{2+}$ or $Mg^{2+}$; and (ii) between or about 0.1 to about 10 millimolar low-molecular-weight antioxidant; or (iii) a combination of (i) and (ii), whereby viability of the plant cells or plant protoplasts in the culture is improved by:

(a) at least 10% over at least 24 hours' culture;
(b) at least 10% over at least 48 hours' culture;
(c) at least 10% over at least 72 hours' culture; or
(d) at least 10% over at least 96 hours' culture, when compared to plant cells or plant protoplasts in a control culture without: (i) at least 40 millimolar $Ca^{2+}$ or $Mg^{2+}$; (ii) between or about 0.1 to about 10 millimolar low-molecular-weight antioxidant; or (iii) a combination of (i) and (ii). In specific embodiments, the method comprises including in the culture conditions of the plant cell or plant protoplast at least one of: (i) at least 40 millimolar $Ca^{2+}$ or $Mg^{2+}$; and (ii) between or about 0.1 to about 10 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these); or (iii) a combination of (i) and (ii), whereby viability of the plant cells or plant protoplasts in the culture is improved by:

(a) at least 10% over at least 24 hours' culture;
(b) at least 10% over at least 48 hours' culture;
(c) at least 10% over at least 72 hours' culture; or
(d) at least 10% over at least 96 hours' culture, when compared to plant cells or plant protoplasts in a control culture without: (i) at least 40 millimolar $Ca^{2+}$ or $Mg^{2+}$; (ii) between or about 0.1 to about 10 millimolar low-molecular-weight thiol; or (iii) a combination of (i) and (ii). In specific embodiments, the method comprises including in the culture conditions of the plant cell or plant protoplast at least one of: (i) at least 100 millimolar $Ca^{2+}$ and/or $Mg^{2+}$; and (ii) at least 1 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these); or (iii) a combination of (i) and (ii), whereby viability of the plant cells or plant protoplasts in the culture is improved by:
(a) at least 10% over at least 24 hours' culture;
(b) at least 10% over at least 48 hours' culture;
(c) at least 10% over at least 72 hours' culture; or
(d) at least 10% over at least 96 hours' culture, when compared to plant cells or plant protoplasts in a control culture without: (i) at least 100 millimolar $Ca^{2+}$ or $Mg^{2+}$; (ii) at least 1 millimolar low-molecular-weight thiol; or (iii) a combination of (i) and (ii).

In embodiments, the method further comprises maintaining the culture medium under hypoxic conditions, e. g., under about one-half normal atmospheric oxygen concentrations or less, for example, at between or about 5 to about 10% oxygen by volume, at about 5 to about 10% oxygen by volume; in certain embodiments, such conditions additionally result in an improved cell division rate in the culture. In certain embodiments, the culture conditions include at least 40 millimolar $Ca^{2+}$ and/or $Mg^{2+}$ in the medium and further include maintaining the culture under hypoxic conditions. In certain embodiments, the method further comprises maintaining the culture medium under between or about 5 to about 10% oxygen by volume. In certain embodiments, the cell division rate of the protoplasts is improved compared to that of protoplasts in control cultures without (i) a relatively high concentration (such as at least 20 millimolar) of a divalent cation, or (ii) an antioxidant, such as, but not limited to, a low-molecular-weight thiol antioxidant; or (iii) hypoxic conditions; or (iv) any combination of (i), (ii), and (iii). In certain embodiments, the cell division rate of the plant cells or plant protoplasts is improved by at least 20%, or by at least 50%, or by at least 75%, or by at least 100%. In an embodiment, the culture conditions include at least 40 millimolar $Ca^{2+}$ and about one-half normal atmospheric oxygen concentrations, and the cell division rate of the plant cells or plant protoplasts is improved by at least 100% (i. e., cell division rate is about twice that observed in similar cultures grown under or subjected to normal atmospheric oxygen concentrations).

In certain embodiments, the plant cells or plant protoplasts in the culture are generally isolated plant cells or plant protoplasts, that is to say, not located in undissociated or intact plant tissues, plant parts, or whole plants. In certain embodiments, however, plant cells in undissociated or intact plant tissues, plant parts, or whole plants are pre-treated with (i) a non-conventionally high concentration (such as at least 30, at least 40, at least 60, at least 80, or at least 100 millimolar) of a divalent cation, or (ii) an antioxidant; or (iii) a combination of (i) and (ii), prior to the plant cells or plant protoplasts being isolated from the treated plant tissues, plant parts, or whole plants. In an embodiment, plant cells in undissociated or intact plant tissues, plant parts, or whole plants are pre-treated with: (i) between or about 40 to about 150 millimolar $Ca^{2+}$ or $Mg^{2+}$; (ii) between or about 0.1 to about 10 millimolar low-molecular-weight antioxidant; or (iii) a combination of (i) and (ii), prior to the plant cells or plant protoplasts being isolated from the pre-treated plant tissues, plant parts, or whole plants, whereby the viability of the isolated plant cells or protoplasts is improved, relative to control plant cells or plant protoplasts isolated from plant tissues, plant parts, or whole plants not so pre-treated.

In certain embodiments, of the systems, methods, and compositions disclosed herein, dissociated plant cells or plant cells in undissociated or intact plant tissues, plant parts, or whole plants are treated with (i) a non-conventionally high concentration (e.g., 30, 40, or 60, to 80, 100, 120, or 150 millimolar) of a divalent cation (e.g., $Ca^{2+}$ and/or $Mg^{2+}$); (ii) a reactive oxygen species (ROS) lowering or scavenging agent (e.g., an antioxidant); (iii) a hypoxia inducing agent or condition (e.g. about 5% to about 10% or 12% oxygen by volume); or (iv) any combination of (i)-(iii). In certain embodiments, such treatments are made prior to the plant cells or plant protoplasts being isolated from the treated plant tissues, plant parts, or whole plants for use in the systems, methods and compositions disclosed herein. In certain embodiments, such treatments are made prior to the plant cells that are located within the plant being used in the systems, methods and compositions disclosed herein. In an embodiment, the disassociated plant cells or plant cells in undissociated or intact plant tissues, plant parts, or whole plants are treated with: (i) about 40 to about 150 millimolar $Ca^{2+}$ and/or $Mg^{2+}$; (ii) a ROS scavenging agent comprising about 0.1 to about 10 millimolar low-molecular-weight antioxidant; (iii) a hypoxia inducing agent or condition (e.g. about 5% to about 10% or 12% oxygen by volume); or (iv) any combination of (i)-(iii)). In certain embodiments, such treatments are made prior to the plant cells or plant protoplasts being isolated from the pre-treated plant tissues, plant parts, or whole plants for use in the systems, methods and compositions disclosed herein. In certain embodiments, such treatments are made prior to the plant cells that are located within the plant being used in the systems, methods and compositions disclosed herein. In certain embodiments, any of such aforementioned treatments of the plant cells can be made in the methods or systems provided herein prior, during, and/or after exposure of the plant cells to genome editing molecules.

In embodiments, the culture, methods, system, or composition includes plant cells or plant protoplasts obtained from or located in any plant part or tissue or callus. In certain embodiments, the culture includes plant cells or plant protoplasts obtained from a plant tissue, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, ovule, pollen, microspore, anther, hypocotyl, cotyledon, leaf, petiole, stem, tuber, root, callus, or plant cell suspension. In certain embodiments, the systems, methods, compositions, or cultures include a plant cell located in a plant tissue, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, ovule, pollen, microspore, anther, hypocotyl, cotyledon, leaf, petiole, stem, tuber, root, callus, or plant cell suspension. In certain embodiments, the culture includes haploid, diploid, or polyploid plant cells or plant protoplasts, for example, those obtained from a haploid, diploid, or polyploid plant, plant part or tissue, or callus. In certain embodiments, the culture, method, system, or composition includes plant cells or plant protoplasts obtained from or located in any monocot or dicot plant species of interest, for example, row crop plants, fruit-producing plants and trees, vegetables, trees, and ornamental plants including ornamental flowers, shrubs, trees, groundcovers, and turf grasses; a non-limiting list of plant species of interest is provided above under the heading "Plant cell and plant protoplast cultures". In certain embodiments, the culture, method, system, or composition includes plant cells or plant protoplasts that are (a) encapsulated or enclosed in or attached to a polymer (e. g., pectin, agarose, or other polysaccharide) or other support (solid or semi-solid surfaces or matrices, or particles or nanoparticles); (b) encapsulated or enclosed in or attached to a vesicle or liposome or other fluid compartment; or (c) not encapsulated or enclosed or attached. In certain embodiments, the culture includes plant cells or plant protoplasts in liquid or suspension culture, or cultured in or on semi-solid or solid media, or in a combination of liquid and solid or semi-solid media (e. g., plant cells or protoplasts cultured on solid medium with a liquid medium overlay, or plant cells or protoplasts attached to solid beads or a matrix and grown with a liquid medium). In certain embodiments, the culture includes plant cells or plant protoplasts encapsulated in a polymer (e. g., pectin, agarose, or other polysaccharide) or other encapsulating material, enclosed in a vesicle or liposome, suspended in a mixed-phase medium (such as an emulsion or reverse emulsion), or embedded in or attached to a matrix or other solid support (e. g., beads or microbeads, membranes, or solid surfaces).

A related aspect of the disclosure relates to the plant cell or plant protoplast or populations thereof having improved viability and/or increased gene-editing frequencies, provided by the methods disclosed herein. Also provided by the disclosure are compositions derived from or grown from the plant cell or plant protoplast having improved viability and/or increased gene-editing frequencies, provided by the methods disclosed herein; such compositions include multiple protoplasts or cells, callus, a somatic embryo, or a regenerated plant, grown from the plant cell or plant protoplast having improved viability and/or increased gene-editing frequencies.

Plant cells or plant protoplasts having increased gene-editing frequencies are provided by the systems and methods disclosed herein. Also provided by the disclosure are compositions derived from or grown from the plant cell or plant protoplast having increased gene-editing frequencies, or provided by the systems and methods disclosed herein. In certain embodiments, such compositions include multiple protoplasts or cells, callus, a somatic embryo. Also provided are a regenerated or otherwise obtained plant, grown from the plant cell or plant protoplast having increased gene-editing frequencies. In certain embodiments, where the genome modification comprises homology directed repair (HDR) of the genome, the frequency of HDR is increased by at least 2-fold, for example, by about 2-, 3-, 4-, or 5-fold to about 10-, 20, 50-, 100-, 200-fold, or more in comparison to a control method wherein a control plant cell is provided with the genome editing molecules but is not exposed to an ROS concentration lowering agent or a hypoxic condition and/or is not exposed to a high concentration of a divalent cation (e.g., at least 30 millimolar of $Ca^{2+}$ and/or $Mg^{2+}$). Also provided herein are populations of plant cells or plant protoplasts that are produced by the systems, methods, or compositions disclosed herein where the percentage of the plant cells or protoplasts in the population comprising the desired genetic modification in a target gene of interest resulting from the activity of the gene editing molecules is increased in comparison to a control system, method, or composition wherein at least one of an ROS concentration lowering agent, a hypoxic condition, and/or a high concentration of divalent cation (e.g., $Ca^{2+}$ and/or $Mg^{2+}$) is absent. In certain embodiments, wherein the genome modification comprises homology directed repair (HDR) of the genome, the frequency of plant cells in the population having the desired genetic modification in a target gene of interest resulting from the activity of the gene editing molecules is increased by at least 2-fold, for example, by about 2-, 3-, 4-, or 5-fold to about 10-, 20, 50-, 100-, 200-fold, or more in comparison to a population produced by a control method wherein a control plant cell is provided with the genome editing molecules but is not exposed to an ROS concentration lowering agent or a hypoxic condition and/or is not exposed to a high concentration of divalent cation (e.g., $Ca^{2+}$ and/or $Mg^{2+}$). In certain embodiments, the increased frequency of plant cells in the population having the desired genetic modification in a target gene of interest resulting from the activity of the gene editing molecules is an additive or synergistic increase in comparison to a population produced by a control system, method, or composition wherein at least one of a ROS concentration lowering agent, a hypoxic condition, and/or a high concentration of divalent cation (e.g., $Ca^{2+}$ and/or $Mg^{2+}$) is absent.

In some embodiments, the method includes the additional step of growing or regenerating a plant from a plant cell or plant protoplast having improved viability and/or increased gene-editing frequencies, a target gene edit, and/or a genome edit as provided by the methods, systems, and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having improved viability and/or increased gene-editing frequencies, a target gene edit, or a genome edit, as well as the seeds of such plants, including seeds with a target gene edit or a genome edit. In certain embodiments wherein the plant cell or plant protoplast having improved viability and/or increased gene-editing frequencies is subjected to genetic or epigenetic modification (for example, stable or transient expression of a transgene, gene silencing, epigenetic silencing, or genome editing by use of genome modification molecules, e. g., an RNA-guided DNA nuclease and guide RNA), the grown or regenerated plant exhibits a phenotype associated with the genetic or epigenetic modification. In certain embodiments, the grown or regenerated plant includes in its genome two or more genetic or epigenetic modifications that in combination provide at least one phenotype of interest. In certain embodiments, a heterogeneous population of plant cells or plant protoplasts having improved viability and/or increased gene-editing frequencies, at least some of which include at least one genetic or epigenetic modification, or a target gene edit, and/or genome edit, is provided by the culture, method, system, or composition. Related aspects include a plant having a phenotype of interest associated with the genetic or epigenetic modification, provided by either regeneration of a plant having the phenotype of interest from a plant cell or plant protoplast selected from the heterogeneous population of plant cells or plant protoplasts having improved viability and/or increased gene-editing frequencies, or by selection of a plant having the phenotype of interest from a heterogeneous population of plants grown or regenerated from the population of plant cells or plant protoplasts having improved viability and/or increased gene-editing frequencies, a target gene edit, and/or a genome edit. Examples of phenotypes of interest include herbicide resistance, improved tolerance of abiotic stress (e. g., tolerance of temperature extremes, drought, or salt) or biotic stress (e. g., resistance to bacterial, nematode, or fungal pathogens), improved utilization of nutrients or water, modified lipid, carbohydrate, or protein composition, improved flavour or appearance, improved storage characteristics (e. g., resistance to bruising, browning, or softening), increased yield, altered morphology (e. g., floral architecture or colour, plant height, branching, root structure). In an embodiment, a heterogeneous population of plant cells or plant protoplasts having improved viability and/or increased gene-editing frequencies (or seedlings or plants grown or regenerated therefrom) is exposed to conditions permitting expression of the phenotype of interest; e. g., selection for herbicide resistance can include exposing the population of plant cells or plant protoplasts having improved viability and/or increased gene-editing frequencies (or seedlings or plants grown or regenerated therefrom) to an amount of herbicide or other substance that inhibits growth or is toxic, allowing identification and selection of those resistant plant cells or plant protoplasts (or seedlings or plants) that survive treatment. Methods for regenerating plants from protoplasts, other plant cells, callus, and the like can be adapted from published procedures (e.g., Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Also provided are heterogeneous populations, arrays, or libraries of such plant cells, plant cell populations, plants, succeeding generations or seeds of such plants grown or regenerated from the plant cells or plant protoplasts having improved viability, target gene edits, and/or genomic edits, parts of the plants (including plant parts used in grafting as scions or rootstocks), or products (e. g., fruits or other edible plant parts, cleaned grains or seeds, edible oils, flours or starches, proteins, and other processed products) made from the plants or their seeds. Embodiments include plants grown or regenerated from the plant cells or plant protoplasts having improved viability and/or increased gene-editing frequencies, target gene edits, and/or genomic edits, wherein the plants contain cells or tissues that do not have a genetic or epigenetic modification, e. g., grafted plants in which the scion or rootstock contains a genetic or epigenetic modification, or chimeric plants in which some but not all cells or tissues contain a genetic or epigenetic modification. Plants in which grafting is commonly useful include many fruit trees and plants such as many citrus trees, apples, stone fruit (e. g., peaches, apricots, cherries, and plums), avocados, tomatoes, eggplant, cucumber, melons, watermelons, and grapes as well as various ornamental plants such as roses. Grafted plants can be grafts between the same or different (generally related) species. Additional related aspects include a hybrid plant provided by crossing a first plant grown or regenerated from a plant cell or plant protoplast having improved viability and/or increased gene-editing frequencies and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. The intact plant itself may be desirable, e. g., plants grown as cover crops or as ornamentals. In other embodiments, processed products are made from the plant or its seeds, such as extracted proteins, oils, sugars, and starches, fermentation products, animal feed or human food, wood and wood products, pharmaceuticals, and various industrial products. Thus, further related aspects of the disclosure include a processed or commodity product made from a plant or seed or plant part that is grown or regenerated from a plant cell or plant protoplast having improved viability and/or increased gene-editing frequencies, target gene edits, and/or genomic edits, as disclosed herein. Commodity and processed products include, but are not limited to, harvested leaves, roots, shoots, tubers, stems, fruits, seeds, or other parts of a plant, meals, oils, extracts, fermentation or digestion products, crushed, macerated, and/or ground whole grains or seeds of a plant, wood and wood pulp, or any food or non-food product.

Compositions, plant cell cultures, systems and reaction mixtures including plant cells or plant protoplasts having improved viability and/or increased gene-editing frequencies are useful, e. g., in methods involving genetic engineering or genome editing. In one aspect, the invention provides a composition including: (a) at least one plant cell or plant protoplast having improved viability, provided by including in the culture conditions (i. e., in at least one medium used in culture) of the plant cell or plant protoplast: (i) a non-conventionally high concentration (such as at least 30, at least 40, at least 60, at least 80, or at least 100 millimolar) of a divalent cation, or (ii) an antioxidant, such as, but not limited to, a low-molecular-weight thiol antioxidant; or (iii) a combination of (i) and (ii); (b) at least one effector or gene editing molecule (e. g., a polynucleotide or a protein or a combination of both) for inducing a genetic alteration in the plant cell or plant protoplast; and (c) optionally, at least one delivery agent (such as at least one chemical, enzymatic, or physical agent). In certain embodiments, the composition is maintained under hypoxic conditions, e. g., at about half of normal atmospheric oxygen concentrations, or at between or about 5% to about 10% oxygen concentrations. Effector or genome editing molecules and delivery agents are described in further detail below. Embodiments include compositions, plant cell cultures, systems, and methods including at least one plant cell or plant protoplast having improved viability and/or increased gene-editing frequencies and at least one effector or genome editing molecule such as an RNA guide for an RNA-guided nuclease (or a polynucleotide encoding an RNA guide for an RNA-guided nuclease); an RNA-guided DNA nuclease (or a polynucleotide encoding an RNA-guided DNA nuclease); an RNA-guided nuclease or RNA-guided DNA nuclease and a guide RNA, and optionally a donor template polynucleotide; a sequence-specific endonuclease and a donor template polynucleotide; one or more polynucleotides encoding an RNA-guided nuclease or RNA-guided DNA nuclease and a guide RNA, and optionally a donor template polynucleotide; one or more polynucleotide(s) encoding a sequence-specific endonuclease and a donor template polynucleotide; or any combination thereof; optionally such compositions further include at least one chemical, enzymatic, or physical delivery agent. In certain embodiments, the at least one plant cell or plant protoplast included in the composition or reaction mixture is characterized as having viability improved by at least 10%, or by at least 15%, or by at least 20%, or by at least 25% after at least about one day of culture time, when compared to the viability of plant cells or plant protoplasts from control cultures without (i) a non-conventionally high concentration (such as at least 30, at least 40, at least 60, at least 80, or at least 100 millimolar) of a divalent cation, or (ii) an antioxidant, such as, but not limited to, a low-molecular-weight thiol antioxidant; or (iii) a combination of (i) and (ii). In certain embodiments where the culture conditions further include hypoxia, the at least one plant cell or plant protoplast included in the composition or reaction mixture is characterized as having improved cell division rates, e. g., improved by at least 25%, or by at least 50%, or by at least about 75%, or by at least about 100%, in comparison to that observed in plant cells or protoplasts from control cultures not maintained under hypoxic conditions.

Compositions, plant cell cultures, systems, methods, and reaction mixtures including plant cells or plant protoplasts having increased target gene or genome editing frequencies compared to controls are provided herein. In certain embodiments, the disclosure provides a composition, system, or method that comprises: (a) at least one plant cell or plant protoplast that is subjected to hypoxic conditions or treated with an ROS scavenging agent; (b) one or more gene or genome editing molecules (e.g., a polynucleotide or a protein or a combination of both); and optionally (c) a non-conventionally high concentration (e.g., 30, 40, or 60, to 80, 100, 120, or 150 millimolar) of a divalent cation (e.g., $Ca^{2+}$ and/or $Mg^{2+}$); for inducing a genetic modification in a target gene of the plant cell or plant protoplast. Such compositions, systems, or methods can also optionally include at least one delivery agent (such as at least one chemical, enzymatic, or physical agent that facilitates polynucleotide entry into a plant cell or protoplast) and/or optionally include a non-conventionally high concentration (such as at least 30, at least 40, at least 60, at least 80, or at least 100 millimolar; or any of the aforementioned ranges) of a divalent cation (e.g., $Mg^{2+}$ and/or $Ca^{2+}$). In certain embodiments, the plant cell in the system, method, or composition is maintained under hypoxic conditions, e.g., at about half of normal atmospheric oxygen concentrations, or at about 5% to about 12% oxygen concentration by volume. Embodiments include aforementioned systems, plant cell cultures, methods, and compositions comprising a gene editing molecule such as an RNA guide for an RNA-guided nuclease (or a polynucleotide encoding an RNA guide for an RNA-guided nuclease) and/or an RNA-guided DNA nuclease (or a polynucleotide encoding an RNA-guided DNA nuclease); optionally such compositions further include a donor template polynucleotide and/or at least one chemical, enzymatic, or physical delivery agent that provides for entry of the gene editing molecule into the plant cell. In certain embodiments of any of the aforementioned compositions, plant cell cultures, systems, methods, and reaction mixtures, the genome editing molecule(s) comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof.

In certain embodiments, the plant cell culture, system, method, or composition includes: (a) at least one plant cell or plant protoplast having improved viability and/or increased gene-editing frequencies, provided by including in the culture conditions: (i) between about or about 40 to about 150 millimolar $Ca^{2+}$ or $Mg^{2+}$; or (ii) between about or about 0.1 to about 10 millimolar low-molecular-weight antioxidant; or (iii) a combination of (i) and (ii); (b) at least one effector or genome editing molecule for inducing a genetic alteration in the plant cell or plant protoplast; and (c) optionally, at least one chemical, enzymatic, or physical delivery agent. In another embodiment, the composition includes: (a) at least one plant cell or plant protoplast having improved viability and/or increased gene-editing frequencies, provided by including in the culture conditions: (i) at least 40 millimolar $Ca^{2+}$ or $Mg^{2+}$; or (ii) between about or about 0.1 to about 10 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these); or (iii) a combination of (i) and (ii); (b) at least one effector or genome editing molecule for inducing a genetic alteration in the plant cell or plant protoplast; and (c) optionally, at least one chemical, enzymatic, or physical delivery agent. In another embodiment, the composition includes: (a) at least one plant cell or plant protoplast having improved viability and/or increased gene-editing frequencies, provided by including in the culture conditions: (i) at least 100 millimolar $Ca^{2+}$ or $Mg^{2+}$; or (ii) at least 1 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these); or (iii) a combination of (i) and (ii); (b) at least one effector or genome editing molecule for inducing a genetic alteration in the plant cell or plant protoplast; and (c) optionally, at least one chemical, enzymatic, or physical delivery agent. In certain embodiments of any of the aforementioned compositions, plant cell cultures, systems, methods, and reaction mixtures, the genome editing molecule(s) comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof.

In specific embodiments, the plant cell culture, system, methods, or composition includes: (a) at least one plant cell or plant protoplast having improved viability and/or increased gene-editing frequencies, provided by including in the culture conditions: (i) between about or about 40 to about 150 millimolar $Ca^{2+}$ or $Mg^{2+}$; and (ii) between about or about 0.1 to about 10 millimolar low-molecular-weight antioxidant; or (iii) a combination of (i) and (ii), whereby viability of the plant cells or plant protoplasts in the culture is improved by at least 10%, or by at least 15%, or by at least 20%, or by at least 25% after at least about one day of culture time, when compared to plant cells or plant protoplasts in a control culture without: (i) between about or about 40 to about 150 millimolar $Ca^{2+}$ or $Mg^{2+}$; (ii) between about or about 0.1 to about 10 millimolar low-molecular-weight antioxidant; or (iii) a combination of (i) and (ii); (b) at least one effector or genome editing molecule for inducing a genetic alteration in the plant cell or plant protoplast; and (c) optionally, at least one chemical, enzymatic, or physical delivery agent. In certain embodiments of any of the aforementioned compositions, plant cell cultures, systems, methods, and reaction mixtures, the genome editing molecule(s) comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof.

In specific embodiments, the plant cell culture, system, method, or composition includes: (a) at least one plant cell or plant protoplast having improved viability and/or increased gene-editing frequencies, provided by including in the culture conditions: (i) at least 40 millimolar $Ca^{2+}$ or $Mg^{2+}$; and (ii) between about or about 0.1 to about 10 millimolar low-molecular-weight antioxidant; or (iii) a combination of (i) and (ii), whereby viability of the plant cells or plant protoplasts in the culture is improved by:
  (a) at least 10% over at least 24 hours' culture;
  (b) at least 10% over at least 48 hours' culture;
  (c) at least 10% over at least 72 hours' culture; or
  (d) at least 10% over at least 96 hours' culture,
when compared to plant cells or plant protoplasts in a control culture without: (i) at least 40 millimolar $Ca^{2+}$ or $Mg^{2+}$; (ii) between about or about 0.1 to about 10 millimolar low-molecular-weight antioxidant; or (iii) a combination of (i) and (ii); (b) at least one effector or genome editing molecule for inducing a genetic alteration in the plant cell or plant protoplast; and (c) optionally, at least one chemical, enzymatic, or physical delivery agent. In specific embodiments, the composition includes: (a) at least one plant cell or plant protoplast having improved viability and/or increased gene-editing frequencies, provided by including in the culture conditions: (i) at least 40 millimolar $Ca^{2+}$ or $Mg^{2+}$; and (ii) between or about 0.1 to about 10 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these); or (iii) a combination of (i) and (ii), whereby viability of the plant cells or plant protoplasts in the culture is improved by:
  (a) at least 10% over at least 24 hours' culture;
  (b) at least 10% over at least 48 hours' culture;
  (c) at least 10% over at least 72 hours' culture; or
  (d) at least 10% over at least 96 hours' culture,
when compared to plant cells or plant protoplasts in a control culture without: (i) at least 40 millimolar $Ca^{2+}$ or $Mg^{2+}$; (ii) between about or about 0.1 to about 10 millimolar low-molecular-weight thiol; or (iii) a combination of (i) and (ii); (b) at least one effector or genome editing molecule for inducing a genetic alteration in the plant cell or plant protoplast; and (c) optionally, at least one chemical, enzymatic, or physical delivery agent. In specific embodiments, the composition includes: (a) at least one plant cell or plant protoplast having improved viability and/or increased gene-editing frequencies, provided by including in the culture conditions: (i) at least 100 millimolar $Ca^{2+}$ or $Mg^{2+}$; and (ii) at least 1 millimolar low-molecular-weight thiol (e. g., glutathione, cysteine, cysteinyl glycine, gamma-glutamyl cysteine, N-acetylcysteine, cysteine, thiocysteine, homocysteine, lipoic acid, dithiothreitol, or a combination of these); or (iii) a combination of (i) and (ii), whereby viability of the plant cells or plant protoplasts in the culture is improved by:
  (a) at least 10% over at least 24 hours' culture;
  (b) at least 10% over at least 48 hours' culture;
  (c) at least 10% over at least 72 hours' culture; or
  (d) at least 10% over at least 96 hours' culture,
when compared to plant cells or plant protoplasts in a control culture without: (i) at least 100 millimolar $Ca^{2+}$ or $Mg^{2+}$; (ii) at least 1 millimolar low-molecular-weight thiol; or (iii) a combination of (i) and (ii); (b) at least one effector molecule for inducing a genetic alteration in the plant cell or plant protoplast (e.g., genome editing molecules for inducing a genetic modification); and (c) optionally, at least one chemical, enzymatic, or physical delivery agent. In various embodiments (such as, but not limited to those described above), the at least one effector or genome editing molecule for inducing a genetic alteration in the plant cell or plant protoplast is selected from the group consisting of: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (iii) a polynucleotide encoding one or more nucleases capable of effecting site-specific alteration of a target nucleotide sequence; and/or (iv) a donor template polynucleotide. In various embodiments (such as, but not limited to those described above), the at least one delivery agent is selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; chelating agents such as ammonium oxalate, EDTA, EGTA, or cyclohexane diamine tetraacetate; non-specific DNA double-strand-break-inducing agents; and antioxidants; particles or nanoparticles, magnetic particles or nanoparticles, abrasive or scarifying agents, needles or microneedles, matrices, and grids. In certain embodiments, the culture, method, system, or composition includes (a) at least one plant cell or plant protoplast having improved viability and/or increased gene-editing frequencies, provided by including in the culture conditions: (i) between about or about 40 to about 150 millimolar $Ca^{2+}$ or $Mg^{2+}$; and (ii) between about or about 0.1 to about 10 millimolar low-molecular-weight antioxidant; or (iii) a combination of (i) and (ii), whereby viability of the plant cells or plant protoplasts in the culture is improved by at least 10%, or by at least 15%, or by at least 20%, or by at least 25% after at least about one day of culture time, when compared to plant cells or plant protoplasts in a control culture without: (i) between about or about 40 to about 150 millimolar $Ca^{2+}$ or $Mg^{2+}$; (ii) between about or about 0.1 to about 10 millimolar low-molecular-weight antioxidant; or (iii) a combination of (i) and (ii); (b) a Cas9, a Cpf1, a CasY, a CasX, a C2c1, or a C2c3 nuclease; (c) at least one guide RNA; and (d) optionally, at least one chemical, enzymatic, or physical delivery agent. In certain embodiments, the composition includes (a) at least one plant cell or plant protoplast having improved viability and/or increased gene-editing frequencies, provided by including in the culture conditions: (i) between or about 40 to about 150 millimolar $Ca^{2+}$ or $Mg^{2+}$; and (ii) between about or about 0.1 to about 10 millimolar low-molecular-weight antioxidant; or (iii) a combination of (i) and (ii), whereby viability of the plant cells or plant protoplasts in the culture is improved by at least 10%, or by at least 15%, or by at least 20%, or by at least 25% after at least about one day of culture time, when compared to plant cells or plant protoplasts in a control culture without: (i) between about or about 40 to about 150 millimolar $Ca^{2+}$ or $Mg^{2+}$; (ii) between about or about 0.1 to about 10 millimolar low-molecular-weight antioxidant; or (iii) a combination of (i) and (ii); (b) at least one ribonucleoprotein including a CRISPR nuclease and a guide RNA; and (c) optionally, at least one chemical, enzymatic, or physical delivery agent. In certain embodiments of any of the aforementioned compositions, plant cell cultures, systems, methods, and reaction mixtures, the genome editing molecule(s) comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof.

Embodiments of the plant cell cultures, methods, systems, and compositions as described in the immediately preceding paragraphs further include those wherein the culture is maintained under hypoxic conditions, e. g., under about one-half normal atmospheric oxygen concentrations or less, for example, at between about or about 5 to about 10%, 11%, or 12% oxygen by volume or any of the other hypoxic conditions disclosed herein. In certain embodiments, such conditions additionally result in an improved cell division rate in the culture. In certain embodiments, the cell division rate of the cells or protoplasts in the composition is improved by at least 10%, or by at least 15%, or by at least 20%, or by at least 25%, or by at least 50%, or by at least 75%, or by at least 100%, or by at least 2-fold, compared to that of cells or protoplasts in control cultures that are similar except that they are not maintained under hypoxic conditions. In certain embodiments, the plant cells (e.g., plant protoplasts) are exposed to the hypoxic conditions about 5, 10, 15, 30, or 45 minutes to about 60, 75, 90, or 120 minutes after exposure to the gene-editing molecules.

In a related aspect, the disclosure provides arrangements of plant cells or plant protoplasts having improved viability and/or increased gene-editing frequencies as provided by the methods and culture conditions described herein, such as arrangements of plant cells or plant protoplasts convenient for screening purposes or for high-throughput and/or multiplex gene editing experiments. Plant cell cultures, compositions, and systems provided herein can be used in the arrangements. Methods provided herein can also be practiced in such arrangements. In an embodiment, the disclosure provides a pooled arrangement of multiple plant cells or plant protoplasts having improved viability and/or increased gene-editing frequencies, provided by including in the culture conditions of the plant cell or plant protoplast (i) a relatively high concentration (such as at least 20 millimolar) of a divalent cation, or (ii) an antioxidant, such as, but not limited to, a low-molecular-weight thiol antioxidant; or (iii) a combination of (i) and (ii); a specific embodiment is such a pooled arrangement of multiple plant cells or plant protoplasts having improved viability and/or increased gene-editing frequencies, further including at least one effector or genome editing molecule (e. g., an RNA-guided DNA nuclease, at least one guide RNA, or a ribonucleoprotein including both an RNA-guided DNA nuclease and at least one guide RNA), and optionally at least one chemical, enzymatic, or physical delivery agent. In certain embodiments, the disclosure provides an arrangement of multiple plant cells or plant protoplasts: (a) a plant cell subjected to a hypoxic condition, or treated with a reactive oxygen species (ROS) scavenging agent, or both subjected to the hypoxic condition and treated with the ROS scavenging agent; and/or (b) a non-conventionally high concentration (e.g., 30, 40, or 60, to 80, 100, 120, or 150 millimolar) of a divalent cation (e.g., $Ca^{2+}$ and/or $Mg^{2+}$); and (c) genome editing molecule(s). In certain embodiments, the arrangements of plant cells can further comprise at least one chemical, enzymatic, or physical delivery agent. In another embodiment, the disclosure provides an array including a plurality of containers, each including at least one plant cell or plant protoplast having improved viability and/or increased gene-editing frequencies, provided by including in the culture conditions of the plant cell or plant protoplast (i) a relatively high concentration (such as at least 20 millimolar) of a divalent cation, or (ii) an antioxidant, such as, but not limited to, a low-molecular-weight thiol antioxidant; or (iii) a combination of (i) and (ii). In an embodiment, the disclosure provides arrangements of plant cells or plant protoplasts having improved viability and/or increased gene-editing frequencies, wherein the plant cells or plant protoplasts are in an arrayed format, for example, in multi-well plates, encapsulated or enclosed in vesicles, liposomes, or droplets (useful, (e. g., in a microfluidics device), or attached discretely to a matrix or to discrete particles or beads; a specific embodiment is such an arrangement of multiple plant cells or plant protoplasts having improved viability and/or increased gene-editing frequencies provided in an arrayed format, further including at least one effector or genome editing molecule (e. g., an RNA-guided DNA nuclease, at least one guide RNA, or a ribonucleoprotein including both an RNA-guided DNA nuclease and at least one guide RNA), which may be different for at least some locations on the array or even for each location on the array, and optionally at least one chemical, enzymatic, or physical delivery agent. In certain embodiments of any of the aforementioned compositions, plant cell cultures, systems, methods, and reaction mixtures involving such arrangements or arrays, the genome editing molecule(s) comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof.

In the systems and methods provided herein, plant cells can be exposed or subjected to gene editing molecules and a reactive oxygen species (ROS) concentration lowering agent and/or hypoxic condition in any temporal order. In certain embodiments, the gene editing molecules and a reactive oxygen species (ROS) concentration lowering agent and/or hypoxic condition are provided simultaneously. In other embodiments, the gene editing molecules are provided simultaneously after a reactive oxygen species (ROS) concentration lowering agent and/or hypoxic condition is provided. In other embodiments, the gene editing molecules are provided and a reactive oxygen species (ROS) concentration lowering agent and/or a hypoxic condition is subsequently provided. In summary, the genome editing molecules can be provided to a plant cell either previous to, concurrently with, or subsequent to exposing the plant cell to: (i) a hypoxic condition, a reactive oxygen species (ROS) concentration lowering agent, or combination thereof.

Effector Molecules: Effector molecules (e.g., gene editing molecules) of use in the compositions and reaction mixtures provided herein include molecules capable of introducing a double-strand break ("DSB") in double-stranded DNA, such as in genomic DNA or in a target gene located within the genomic DNA as well as accompanying guide RNA or donor template polynucleotides. Examples of such gene editing molecules include: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effecting site-specific alteration (such as introduction of a DSB) of a target nucleotide sequence; and (c) a guide RNA (gRNA) for an RNA-guided nuclease, or a DNA encoding a gRNA for an RNA-guided nuclease; and (d) donor template polynucleotides.

CRISPR (Clustered Regularly Interspaced Short Palindromic Repeats)/Cas (CRISPR-associated) systems, or CRISPR systems, are adaptive defense systems originally discovered in bacteria and archaea. CRISPR systems use RNA-guided nucleases termed CRISPR-associated or "Cas" endonucleases (e. g., Cas9 or Cpf1) to cleave foreign DNA. In a typical CRISPR/Cas system, a Cas endonuclease is directed to a target nucleotide sequence (e. g., a site in the genome that is to be sequence-edited) by sequence-specific, non-coding "guide RNAs" that target single- or double-stranded DNA sequences. In microbial hosts, CRISPR loci encode both Cas endonucleases and "CRISPR arrays" of the non-coding RNA elements that determine the specificity of the CRISPR-mediated nucleic acid cleavage.

Three classes (I-III) of CRISPR systems have been identified across a wide range of bacterial hosts and can be adapted for use in the plant cell cultures, systems, methods, and compositions provided herein. The well characterized class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically a 20-nucleotide RNA sequence that corresponds to (i. e., is identical or nearly identical to, or alternatively is complementary or nearly complementary to) a 20-nucleotide target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence.

The target DNA sequence must generally be adjacent to a "protospacer adjacent motif" ("PAM") that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (Streptococcus pyogenes), 5'-NNAGAA (SEQ ID NO:1; Streptococcus thermophilus CRISPR1), 5'-NGGNG (SEQ ID NO:2; Streptococcus thermophilus CRISPR3), 5'-NNGRRT (SEQ ID NO:3); or 5'-NNGRR (SEQ ID NO:4; Staphylococcus aureus Cas9, SaCas9), and 5'-NNNGATT (SEQ ID NO:5: Neisseria meningitidis). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site.

Another class II CRISPR system that can be adapted for use in the plant cell cultures, systems, methods, and compositions provided herein includes the type V endonuclease Cpf1, which is a smaller endonuclease than is Cas9; examples include AsCpf1 (from Acidaminococcus sp.) and LbCpf1 (from Lachnospiraceae sp.). Cpf1-associated CRISPR arrays are processed into mature crRNAs without the requirement of a tracrRNA; in other words, a Cpf1 system requires only the Cpf1 nuclease and a crRNA to cleave the target DNA sequence. Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) *Cell*, 163:759-771. Other CRISPR nucleases useful in methods, systems, and compositions of the disclosure include C2c1 and C2c3 (see Shmakov et al. (2015) *Mol. Cell*, 60:385-397). Like other CRISPR nucleases, C2c1 from *Alicyclobacillus acidoterrestris* (AacC2c1; amino acid sequence with accession ID T0D7A2, deposited on-line at www[dot]ncbi[dot]nlm[dot]nih[dot]gov/protein/ 1076761101) requires a guide RNA and PAM recognition site; C2c1 cleavage results in a staggered seven-nucleotide DSB in the target DNA (see Yang et al. (2016) *Cell*, 167:1814-1828.e12) and is reported to have high mismatch sensitivity, thus reducing off-target effects (see Liu et al. (2016) *Mol. Cell*, available on line at dx[dot]doi[dot]org/10 [dot]1016/j[dot]molce1[dot]2016 [dot]11.040). Another CRISPR nuclease, *Campylobacter jejuni*-derived Cas9 (CjCas9), is only 984 amino acids in length (considerably smaller than, for example, *S. pyogenes* Cas9 at 1368 amino acids or *S. aureus* Cas9 at 1053 amino acids); CjCas9 also requires a guide RNA (reported to be optimal for a 22-nucleotide target sequence) and a PAM recognition site (reported to be 5'-NNNNACAC (SEQ ID NO:6), 5'-NNNNRY (SEQ ID NO:7), 5'-NNNNACA (SEQ ID NO:8), or 5'-NNNNRYAC (SEQ ID NO:9), where R is a purine and Y is a pyrimidine); see Kim et al. (2017) *Nature Communications*, 8:14500 (doi:10.1038/ncomms14500). Yet other CRISPR nucleases include nucleases identified from the genomes of uncultivated microbes, such as CasX and CasY (e. g., a CRISPR-associated protein CasY from an uncultured Parcubacteria group bacterium, amino acid sequence with accession ID APG80656, deposited on-line at www[dot]ncbi[dot]nlm[dot]nih[dot]gov/protein/ APG80656.1]); see Burstein et al. (2016) *Nature*, doi: 10.1038/nature21059.

CRISPR-type genome editing has value in various aspects of agriculture research and development and can be adapted for use in the systems, methods, and compositions provided herein in several ways. CRISPR elements, i. e., CRISPR endonucleases and CRISPR single-guide RNAs, are useful in effecting genome editing without remnants of the CRISPR elements or selective genetic markers occurring in progeny. In certain embodiments, the CRISPR elements are provided directly to the systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate. Alternatively, genome-inserted CRISPR elements are useful in plant lines adapted for multiplex genetic screening and breeding. For instance, a plant species can be created to express one or more of a CRISPR endonuclease such as a Cas9- or a Cpf1-type endonuclease or combinations with unique PAM recognition sites. Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

Whereas wild-type Cas9 generates double-strand breaks (DSBs) at specific DNA sequences targeted by a gRNA, a number of CRISPR endonucleases having modified functionalities are available and can be used in the systems, methods, and compositions provided herein. For example: (1) a "nickase" version of Cas9 generates only a single-strand break; (2) a catalytically inactive Cas9 ("dCas9") does not cut the target DNA but interferes with transcription; dCas9 can further be fused with a repressor peptide; (3) a catalytically inactive Cas9 ("dCas9") fused to an activator peptide can activate or increase gene expression; (4) a catalytically inactive Cas9 (dCas9) fused to FokI nuclease ("dCas9-FokI") can be used to generate DSBs at target sequences homologous to two gRNAs. See, e. g., the numerous CRISPR/Cas9 plasmids disclosed in and publicly available from the Addgene repository (Addgene, 75 Sidney St., Suite 550A, Cambridge, Mass. 02139; addgene[dot]org/crispr/). A "double nickase" Cas9 that introduces two separate double-strand breaks, each directed by a separate guide RNA, is described as achieving more accurate genome editing by Ran et al. (2013) *Cell,* 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include C2c1 and C2c3 (see Shmakov et al. (2015) *Mol. Cell,* 60:385-397) and CasX and CasY (see Burstein et al. (2016) *Nature,* doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of between or about 17-24 nucleotides (frequently 19, 20, or 21 nucleotides) and exact complementarity (i. e., perfect base-pairing) to the targeted gene or nucleic acid sequence; guide RNAs having less than 100% complementarity to the target sequence can be used (e. g., a gRNA with a length of 20 nucleotides and between or about 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991.

In embodiments, the guide RNA (gRNA) has a sequence of between or about 16-24 nucleotides in length (e. g., 16, 17, 18, 19, 20, 21, 22, 23, or 24 nucleotides in length). Specific embodiments include gRNAs of 19, 20, or 21 nucleotides in length and having 100% complementarity to the target nucleotide sequence. In many embodiments the gRNA has exact complementarity (i. e., perfect base-pairing) to the target nucleotide sequence; in certain other embodiments the gRNA has less than 100% complementarity to the target nucleotide sequence. The design of effective gRNAs for use in plant genome editing is disclosed in US Patent Application Publication 2015/0082478 A1, the entire specification of which is incorporated herein by reference. In certain embodiments where multiple gRNAs are employed, the multiple gRNAs can be delivered separately (as separate RNA molecules or encoded by separate DNA molecules) or in combination, e. g., as an RNA molecule containing multiple gRNA sequences or as a DNA molecule encoding an RNA molecule containing multiple gRNA sequences; see, for example, US Patent Application Publication 2016/0264981 A1, the entire specification of which is incorporated herein by reference, which discloses RNA molecules including multiple RNA sequences (such as gRNA sequences) separated by tRNA cleavage sequences. Efficient Cas9-mediated gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing).

Thus, in certain embodiments wherein the nuclease is a Cas9-type nuclease, the gRNA can be provided as a polynucleotide composition including: (a) a CRISPR RNA (crRNA) that includes the gRNA together with a separate tracrRNA, or (b) at least one polynucleotide that encodes a crRNA and a tracrRNA (on a single polynucleotide or on separate polynucleotides), or (c) at least one polynucleotide that is processed into one or more crRNAs and a tracrRNA. In other embodiments wherein the nuclease is a Cas9-type nuclease, the gRNA can be provided as a polynucleotide composition including a CRISPR RNA (crRNA) that includes the gRNA, and the required tracrRNA is provided in a separate composition or in a separate step, or is otherwise provided to the cell (for example, to a plant cell or plant protoplast that stably or transiently expresses the tracrRNA from a polynucleotide encoding the tracrRNA). In other embodiments wherein the nuclease is a Cas9-type nuclease, the gRNA can be provided as a polynucleotide composition comprising: (a) a single guide RNA (sgRNA) that includes the gRNA, or (b) a polynucleotide that encodes a sgRNA, or (c) a polynucleotide that is processed into a sgRNA. Cpf1-mediated gene editing does not require a tracrRNA; thus, in certain embodiments wherein the nuclease is a Cpf1-type nuclease, the gRNA is provided as a polynucleotide composition comprising (a) a CRISPR RNA (crRNA) that includes the gRNA, or (b) a polynucleotide that encodes a crRNA, or (c) a polynucleotide that is processed into a crRNA. In certain embodiments, the gRNA-containing composition optionally includes an RNA-guided nuclease, or a polynucleotide that encodes the RNA-guided nuclease. In other embodiments, an RNA-guided nuclease or a polynucleotide that encodes the RNA-guided nuclease is provided in a separate step. In some embodiments of the method, a gRNA is provided to a cell (e. g., a plant cell or plant protoplast) that includes an RNA-guided nuclease or a polynucleotide that encodes an RNA-guided nuclease, e. g., an RNA-guided nuclease selected from the group consisting of an RNA-guided DNA endonuclease, a type II Cas nuclease, a Cas9, a type V Cas nuclease, a Cpf1, a CasY, a CasX, a C2c1, a C2c3, an engineered RNA-guided nuclease, and a codon-optimized RNA-guided nuclease; in an example, the cell (e. g., a plant cell or plant protoplast) stably or transiently expresses the RNA-guided nuclease. In certain embodiments, the polynucleotide that encodes the RNA-guided nuclease is, for example, DNA that encodes the RNA-guided nuclease and is stably integrated in the genome of a plant cell or plant protoplast, DNA or RNA that encodes the RNA-guided nuclease and is transiently present in or introduced into a plant cell or plant protoplast; such DNA or RNA can be introduced, e. g., by using a vector such as a plasmid or viral vector or as an mRNA, or as vector-less DNA or RNA introduced directly into a plant cell or plant protoplast.

In embodiments, the RNA-guided nuclease is provided as a ribonucleoprotein (RNP) complex, e. g., a preassembled RNP that includes the RNA-guided nuclease complexed with a polynucleotide including the gRNA or encoding a gRNA, or a preassembled RNP that includes a polynucleotide that encodes the RNA-guided nuclease (and optionally encodes the gRNA, or is provided with a separate polynucleotide including the gRNA or encoding a gRNA), complexed with a protein. In certain embodiments, the RNA-guided nuclease is a fusion protein, i. e., wherein the RNA-guided nuclease (e. g., Cas9, Cpf1, CasY, CasX, C2c1, or C2c3) is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In certain embodiments, the RNA-guided nuclease or a polynucleotide that encodes the RNA-guided nuclease is provided as a complex with a cell-penetrating peptide or other transfecting agent. In certain embodiments, the RNA-guided nuclease or a polynucleotide that encodes the RNA-guided nuclease is complexed with, or covalently or non-covalently bound to, a further element, e. g., a carrier molecule, an antibody, an antigen, a viral movement protein, a polymer, a detectable label (e. g., a moiety detectable by fluorescence, radioactivity, or enzymatic or immunochemical reaction), a quantum dot, or a particulate or nanoparticulate. In certain embodiments, the RNA-guided nuclease or a polynucleotide that encodes the RNA-guided nuclease is provided in a solution, or is provided in a liposome, micelle, emulsion, reverse emulsion, suspension, or other mixed-phase composition. In certain embodiments, the DNA or RNA is introduced directly into a plant cell or plant protoplast.

An RNA-guided nuclease can be provided to a cell (e. g., a plant cell or plant protoplast) by any suitable technique. In certain embodiments, the RNA-guided nuclease is provided by directly contacting a plant cell or plant protoplast with the RNA-guided nuclease or the polynucleotide that encodes the RNA-guided nuclease. In certain embodiments, the RNA-guided nuclease is provided by transporting the RNA-guided nuclease or a polynucleotide that encodes the RNA-guided nuclease into a plant cell or plant protoplast using a chemical, enzymatic, or physical agent as provided in detail in the paragraphs following the heading "Delivery Methods and Delivery Agents". In certain embodiments, the RNA-guided nuclease is provided by bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of a plant cell or plant protoplast with a polynucleotide encoding the RNA-guided nuclease; see, e. g., Broothaerts et al. (2005) *Nature*, 433: 629-633. In an embodiment, the RNA-guided nuclease is provided by transcription in a plant cell or plant protoplast of a DNA that encodes the RNA-guided nuclease and is stably integrated in the genome of the plant cell or plant protoplast or that is provided to the plant cell or plant protoplast in the form of a plasmid or expression vector (e. g., a viral vector) that encodes the RNA-guided nuclease (and optionally encodes one or more gRNAs, crRNAs, or sgRNAs, or is optionally provided with a separate plasmid or vector that encodes one or more gRNAs, crRNAs, or sgRNAs). In certain embodiments, the RNA-guided nuclease is provided to the plant cell or plant protoplast as a polynucleotide that encodes the RNA-guided nuclease, e. g., in the form of an mRNA encoding the nuclease.

Where a polynucleotide is concerned (e. g., a crRNA that includes the gRNA together with a separate tracrRNA, or a crRNA and a tracrRNA encoded on a single polynucleotide or on separate polynucleotides, or at least one polynucleotide that is processed into one or more crRNAs and a tracrRNA, or a sgRNA that includes the gRNA, or a polynucleotide that encodes a sgRNA, or a polynucleotide that is processed into a sgRNA, or a polynucleotide that encodes the RNA-guided nuclease), embodiments of the polynucleotide include: (a) double-stranded RNA; (b) single-stranded RNA; (c) chemically modified RNA; (d) double-stranded DNA; (e) single-stranded DNA; (f) chemically modified DNA; or (g) a combination of (a)-(f). Where expression of a polynucleotide is involved (e. g., expression of a crRNA from a DNA encoding the crRNA, or expression and translation of an RNA-guided nuclease from a DNA encoding the nuclease), in some embodiments it is sufficient that expression be transient, i. e., not necessarily permanent or stable in the cell. Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e. g., a sequence-specific recombinase or endonuclease site), T-DNA (e. g., DNA sequence encoding a gRNA, crRNA, tracrRNA, or sgRNA is enclosed between left and right T-DNA borders from *Agrobacterium* spp. or from other bacteria that infect or induce tumours in plants), a DNA nuclear-targeting sequence, a regulatory sequence such as a promoter sequence, and a transcript-stabilizing sequence. Certain embodiments of the polynucleotide include those wherein the polynucleotide is complexed with, or covalently or non-covalently bound to, a non-nucleic acid element, e. g., a carrier molecule, an antibody, an antigen, a viral movement protein, a cell-penetrating or pore-forming peptide, a polymer, a detectable label, a quantum dot, or a particulate or nanoparticulate.

Apart from the CRISPR-type nucleases, other nucleases capable of effecting site-specific alteration or modification of a target nucleotide sequence in the plant cell cultures, systems, methods, and compositions provided herein include zinc-finger nucleases (ZFNs), transcription activator-like effector nucleases (TAL-effector nucleases or TALENs), Argonaute proteins, and a meganuclease or engineered meganuclease. Zinc finger nucleases (ZFNs) are engineered proteins comprising a zinc finger DNA-binding domain fused to a nucleic acid cleavage domain, e. g., a nuclease. The zinc finger binding domains provide specificity and can be engineered to specifically recognize any desired target DNA sequence. For a review of the construction and use of ZFNs in plants and other organisms, see, e. g., Urnov et al. (2010) *Nature Rev. Genet.,* 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotides bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e. g., U.S. Pat. Nos. 6,453,242 and 6,534,261, both incorporated herein by reference in their entirety. Exemplary selection methods (e. g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e. g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonautes are proteins that can function as sequence-specific endonucleases by binding a polynucleotide (e. g., a single-stranded DNA or single-stranded RNA) that includes sequence complementary to a target nucleotide sequence) that guides the Argonaut to the target nucleotide sequence and effects site-specific alteration of the target nucleotide sequence; see, e. g., US Patent Application Publication 2015/0089681, incorporated herein by reference in its entirety.

In related embodiments, zinc finger nucleases, TALENs, and Argonautes are used in conjunction with other functional domains. For example, the nuclease activity of these nucleic acid targeting systems can be altered so that the enzyme binds to but does not cleave the DNA. Examples of functional domains include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SHH1, SUVH2, or SUVH9 polypeptide capable of reducing expression of a target nucleotide sequence via epigenetic modification; see, e. g., US Patent Application Publication 2016/0017348, incorporated herein by reference in its entirety. Genomic DNA may also be modified via base editing using a fusion between a catalytically inactive Cas9 (dCas9) is fused to a cytidine deaminase which convert cytosine (C) to uridine (U), thereby effecting a C to T substitution; see Komor et al. (2016) Nature, 533:420-424.

In some embodiments, one or more vectors driving expression of one or more polynucleotides encoding elements of a genome-editing system (e. g., encoding a guide RNA or a nuclease) are introduced into a plant cell or a plant protoplast, whereby these elements, when expressed, result in alteration of a target nucleotide sequence. In certain embodiments, a vector comprises a regulatory element such as a promoter operably linked to one or more polynucleotides encoding elements of a genome-editing system. In such embodiments, expression of these polynucleotides can be controlled by selection of the appropriate promoter, particularly promoters functional in a plant cell; useful promoters include constitutive, conditional, inducible, and temporally or spatially specific promoters (e. g., a tissue specific promoter, a developmentally regulated promoter, or a cell cycle regulated promoter). In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e. g., Ferré-D'Amaré and Scott (2014) Cold Spring Harbor Perspectives Biol., 2:a003574). In certain embodiments, the promoter is a pol II promoter operably linked to a nucleotide sequence encoding one or more guide RNAs. In certain embodiments, the promoter operably linked to one or more polynucleotides encoding elements of a genome-editing system is a constitutive promoter that drives DNA expression in plant cells; in certain embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and a opaline synthase (NOS) and octapine synthase (OCS) promoter from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the nucleic acid targeting system to germline or reproductive cells (e. g., promoters of genes encoding DNA ligases, recombinases, replicases, or other genes specifically expressed in germline or reproductive cells); in such embodiments, the nuclease-mediated genetic modification (e. g., chromosomal or episomal double-stranded DNA cleavage) is limited only those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

In some embodiments, elements of a genome-editing system (e. g., one or more polynucleotides encoding an RNA-guided nuclease and a guide RNA and optionally a donor template polynucleotide or one or more polynucleotide(s) encoding a sequence-specific endonuclease and a donor template polynucleotide) are operably linked to separate regulatory elements on separate vectors. In other embodiments, two or more elements of a genome-editing system expressed from the same or different regulatory elements or promoters are combined in a single vector, optionally with one or more additional vectors providing any additional necessary elements of a genome-editing system not included in the first vector. For example, multiple guide RNAs can be expressed from one vector, with the appropriate RNA-guided nuclease expressed from a second vector. In another example, one or more vectors for the expression of one or more guide RNAs (e. g., crRNAs or sgRNAs) are delivered to a cell (e. g., a plant cell or a plant protoplast) that expresses the appropriate RNA-guided nuclease, or to a cell that otherwise contains the nuclease, such as by way of prior administration thereto of a vector for in vivo expression of the nuclease.

Genome-editing system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, the endonuclease and the nucleic acid-targeting guide RNA may be operably linked to and expressed from the same promoter. In certain embodiments, a single promoter drives expression of a transcript encoding an endonuclease and the guide RNA, embedded within one or more intron sequences (e. g., each in a different intron, two or more in at least one intron, or all in a single intron), which can be plant-derived; such use of introns is especially contemplated when the expression vector is being transformed or transfected into a monocot plant cell or a monocot plant protoplast.

Expression vectors provided herein may contain a DNA segment near the 3' end of an expression cassette that acts as a signal to terminate transcription and directs polyadenylation of the resultant mRNA. Such a 3' element is commonly referred to as a "3'-untranslated region" or "3'-UTR" or a "polyadenylation signal". Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1, incorporated herein by reference.

In certain embodiments, a vector or an expression cassette includes additional components, e. g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector. In certain embodiments, the vector or expression cassette includes additional elements for improving delivery to a plant cell or plant protoplast or for directing or modifying expression of one or more genome-editing system elements, for example, fusing a sequence encoding a cell-penetrating peptide, localization signal, transit, or targeting peptide to the RNA-guided nuclease, or adding a nucleotide sequence to stabilize a guide RNA; such fusion proteins (and the polypeptides encoding such fusion proteins) or combination polypeptides, as well as expression cassettes and vectors for their expression in a cell, are specifically claimed. In certain embodiments, an RNA-guided nuclease (e. g., Cas9, Cpf1, CasY, CasX, C2c1, or C2c3) is fused to a localization signal, transit, or targeting peptide, e. g., a nuclear localization signal (NLS), a chloroplast transit peptide (CTP), or a mitochondrial targeting peptide (MTP); in a vector or an expression cassette, the nucleotide sequence encoding any of these can be located either 5' and/or 3' to the DNA encoding the nuclease. For example, a plant-codon-optimized Cas9 (pco-Cas9) from *Streptococcus pyogenes* and *S. thermophilus* containing nuclear localization signals and codon-optimized for expression in maize is disclosed in PCT/US2015/018104 (published as WO/2015/131101 and claiming priority to U.S. Provisional Patent Application 61/945,700), incorporated herein by reference. In another example, a chloroplast-targeting RNA is appended to the 5' end of an mRNA encoding an endonuclease to drive the accumulation of the mRNA in chloroplasts; see Gomez, et al. (2010) *Plant Signal Behav.*, 5: 1517-1519. In an embodiment, a Cas9 from *Streptococcus pyogenes* is fused to a nuclear localization signal (NLS), such as the NLS from SV40. In an embodiment, a Cas9 from *Streptococcus pyogenes* is fused to a cell-penetrating peptide (CPP), such as octa-arginine or nona-arginine or a homoarginine 12-mer oligopeptide, or a CPP disclosed in the database of cell-penetrating peptides CPPsite 2.0, publicly available at crdd [dot]osdd[dot]net/raghava/cppsite/. In an embodiment, a Cas9 from *Streptococcus pyogenes* is fused to a chloroplast transit peptide (CTP) sequence. In certain embodiments, a CTP sequence is obtained from any nuclear gene that encodes a protein that targets a chloroplast, and the isolated or synthesized CTP DNA is appended to the 5' end of the DNA that encodes a nuclease targeted for use in a chloroplast. Chloroplast transit peptides and their use are described in U.S. Pat. Nos. 5,188,642, 5,728,925, and 8,420,888, all of which are incorporated herein by reference in their entirety. Specifically, the CTP nucleotide sequences provided with the sequence identifier (SEQ ID) numbers 12-15 and 17-22 of U.S. Pat. No. 8,420,888 are incorporated herein by reference. In an embodiment, a Cas9 from *Streptococcus pyogenes* is fused to a mitochondrial targeting peptide (MTP), such as a plant MTP sequence; see, e. g., Jores et al. (2016) *Nature Communications*, 7:12036-12051.

Plasmids designed for use in plants and encoding CRISPR genome editing elements (CRISPR nucleases and guide RNAs) are publicly available from plasmid repositories such as Addgene (Cambridge, Mass.; also see "addgene[dot] com") or can be designed using publicly disclosed sequences, e. g., sequences of CRISPR nucleases. In certain embodiments, such plasmids are used to co-express both CRISPR nuclease mRNA and guide RNA(s); in other embodiments, CRISPR endonuclease mRNA and guide RNA are encoded on separate plasmids. In certain embodiments, the plasmids are *Agrobacterium* TI plasmids. Materials and methods for preparing expression cassettes and vectors for CRISPR endonuclease and guide RNA for stably integrated and/or transient plant transformation are disclosed in PCT/US2015/018104 (published as WO/2015/ 131101 and claiming priority to U.S. Provisional Patent Application 61/945,700), US Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In certain embodiments, such expression cassettes are isolated linear fragments, or are part of a larger construct that includes bacterial replication elements and selectable markers; such embodiments are useful, e. g., for particle bombardment or nanoparticle delivery or protoplast transformation. In certain embodiments, the expression cassette is adjacent to or located between T-DNA borders or contained within a binary vector, e. g., for *Agrobacterium*-mediated transformation. In certain embodiments, a plasmid encoding a CRISPR nuclease is delivered to cell (such as a plant cell or a plant protoplast) for stable integration of the CRISPR nuclease into the genome of cell, or alternatively for transient expression of the CRISPR nuclease. In certain embodiments, plasmids encoding a CRISPR nuclease are delivered to a plant cell or a plant protoplast to achieve stable or transient expression of the CRISPR nuclease, and one or multiple guide RNAs (such as a library of individual guide RNAs or multiple pooled guide RNAs) or plasmids encoding the guide RNAs are delivered to the plant cell or plant protoplast individually or in combinations, thus providing libraries or arrays of plant cells or plant protoplasts (or of plant callus or whole plants derived therefrom), in which a variety of genome edits are provided by the different guide RNAs.

In certain embodiments where the genome-editing system is a CRISPR system, expression of the guide RNA is driven by a plant U6 spliceosomal RNA promoter, which can be native to the genome of the plant cell or from a different species, e. g., a U6 promoter from maize, tomato, or soybean such as those disclosed in PCT/US2015/018104 (published as WO 2015/131101 and claiming priority to U.S. Provisional Patent Application 61/945,700), incorporated herein by reference, or a homologue thereof; such a promoter is operably linked to DNA encoding the guide RNA for directing an endonuclease, followed by a suitable 3' element such as a U6 poly-T terminator. In another embodiment, an expression cassette for expressing guide RNAs in plants is used, wherein the promoter is a plant U3, 7SL (signal recognition particle RNA), U2, or U5 promoter, or chimerics thereof, e. g., as described in PCT/US2015/018104 (published as WO 2015/131101 and claiming priority to U.S. Provisional Patent Application 61/945,700), incorporated herein by reference. When multiple or different guide RNA sequences are used, a single expression construct may be used to correspondingly direct the genome editing activity to the multiple or different target sequences in a cell, such a plant cell or a plant protoplast. In various embodiments, a single vector includes 1, 2, 3, 4, 5, 6, 7, 8, 9, 10, about 15, about 20, or more guide RNA sequences; in other embodiments, 1, 2, 3, 4, 5, 6, 7, 8, 9, 10, about 15, about 20, or more guide RNA sequences are provided on multiple vectors, which can be delivered to one or multiple plant cells or plant protoplasts (e. g., delivered to an array of plant cells or plant protoplasts, or to a pooled population of plant cells or plant protoplasts).

In embodiments, one or more guide RNAs and the corresponding RNA-guided nuclease are delivered together or simultaneously. In other embodiments, one or more guide RNAs and the corresponding RNA-guided nuclease are delivered separately; these can be delivered in separate, discrete steps and using the same or different delivery techniques. In an example, an RNA-guided nuclease is delivered to a cell (such as a plant cell or plant protoplast)

by particle bombardment, on carbon nanotubes, or by *Agrobacterium*-mediated transformation, and one or more guide RNAs is delivered to the cell in a separate step using the same or different delivery technique. In certain embodiments, an RNA-guided nuclease encoded by a DNA molecule or an mRNA is delivered to a cell with enough time prior to delivery of the guide RNA to permit expression of the nuclease in the cell; for example, an RNA-guided nuclease encoded by a DNA molecule or an mRNA is delivered to a plant cell or plant protoplast between or about 1-12 hours (e. g., about 1, 2, 3, 4, 5, 6, 7, 8, 9, 10, 11, or 12 hours, or between about or about 1-6 hours or between about or about 2-6 hours) prior to the delivery of the guide RNA to the plant cell or plant protoplast. In certain embodiments, whether the RNA-guided nuclease is delivered simultaneously with or separately from an initial dose of guide RNA, succeeding "booster" doses of guide RNA are delivered subsequent to the delivery of the initial dose; for example, a second "booster" dose of guide RNA is delivered to a plant cell or plant protoplast between about or about 1-12 hours (e. g., about 1, 2, 3, 4, 5, 6, 7, 8, 9, 10, 11, or 12 hours, or between about or about 1-6 hours or between about or about 2-6 hours) subsequent to the delivery of the initial dose of guide RNA to the plant cell or plant protoplast. Similarly, in some embodiments, multiple deliveries of an RNA-guided nuclease or of a DNA molecule or an mRNA encoding an RNA-guided nuclease are used to increase efficiency of the genome modification.

In embodiments, the desired genome modification involves homologous recombination, wherein one or more double-stranded DNA break in the target nucleotide sequence is generated by the RNA-guided nuclease and guide RNA(s), followed by repair of the break(s) using a homologous recombination mechanism ("homology-directed repair"). In such embodiments, a donor template that encodes the desired nucleotide sequence to be inserted or knocked-in at the double-stranded break is provided to the cell (such as a plant cell or plant protoplast); examples of suitable templates include single-stranded DNA templates and double-stranded DNA templates (e. g., in the form of a plasmid). In general, a donor template encoding a nucleotide change over a region of less than about 50 nucleotides is conveniently provided in the form of single-stranded DNA; larger donor templates (e. g., more than 100 nucleotides) are often conveniently provided as double-stranded DNA plasmids. In certain embodiments, the various compositions and methods described herein for delivering guide RNAs and nucleases are also generally useful for delivering the donor template polynucleotide to the cell; this delivery can be simultaneous with, or separate from (generally after) delivery of the nuclease and guide RNA to the cell. For example, a donor template can be transiently introduced into a plant cell or plant protoplast, optionally with the nuclease and/or gRNA; in certain embodiments, the donor template is provided to the plant cell or plant protoplast in a quantity that is sufficient to achieve the desired homology-directed repair but that does not persist in the plant cell or plant protoplast after a given period of time (e. g., after one or more cell division cycles). In certain embodiments, a donor template has a core nucleotide sequence that differs from the target nucleotide sequence (e. g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in certain embodiments, the regions of high identity include at least 10, at least 50, at least 100, at least 150, at least 200, at least 300, at least 400, at least 500, at least 600, at least 750, or at least 1000 nucleotides on each side of the core sequence. In certain embodiments where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In certain embodiments where the donor template is in the form of a double-stranded DNA plasmid, the core sequence is flanked by homology arms including at least 500, at least 600, at least 700, at least 800, at least 900, or at least 1000 nucleotides on each side of the core sequence. In an embodiment, two separate double-strand breaks are introduced into the cell's target nucleotide sequence with a "double nickase" Cas9 (see Ran et al. (2013) Cell, 154:1380-1389), followed by delivery of the donor template.

Delivery Methods and Delivery Agents: Various treatments are useful in delivery of a polynucleotide, including a guide RNA (gRNA), such as a crRNA or sgRNA (or a polynucleotide encoding such), donor template polynucleotide, polynucleotide encoding a nuclease (e.g., RNA-guided nuclease or sequence-specific endonuclease), or a polynucleotide encoding an ROS scavenging agent to a plant cell or plant protoplast. In certain embodiments, one or more treatments is employed to deliver the gRNA or other polynucleotide (e.g., donor template polynucleotide, or a polynucleotide encoding an ROS scavenging agent) into a plant, plant cell or plant protoplast, e. g., through barriers such as a cell wall or a plasma membrane or nuclear envelope or other lipid bilayer. In an embodiment, a gRNA- or other polynucleotide-containing composition is delivered directly, for example by direct contact of the polynucleotide composition with a plant cell or plant protoplast. A gRNA- or other polynucleotide (e.g., donor template polynucleotide, polynucleotide encoding a nuclease, or a polynucleotide encoding an ROS scavenging agent)-containing composition in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant cell or plant protoplast (e. g., through abrasion or puncture or otherwise disruption of the cell wall or cell membrane, by spraying or dipping or soaking or otherwise directly contacting, by microinjection). For example, a plant cell or plant protoplast is soaked in a liquid gRNA- or other polynucleotide-containing composition, whereby the gRNA or other polynucleotide is delivered to the plant cell or plant protoplast. In certain embodiments, the gRNA- or other polynucleotide-containing composition is delivered using negative or positive pressure, for example, using vacuum infiltration or application of hydrodynamic or fluid pressure. In certain embodiments, the gRNA- or other polynucleotide-containing composition is introduced into a plant cell or plant protoplast, e. g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e. g., delivery of materials to cells employing microfluidic flow through a cell-deforming constriction as described in US Published Patent Application 2014/0287509, incorporated by reference in its entirety herein. Other techniques useful for delivering the gRNA- or other polynucleotide-containing composition to a plant cell or plant protoplast include: ultrasound or sonication; vibration, friction, shear stress, vortexing, cavitation;

centrifugation or application of mechanical force; mechanical cell wall or cell membrane deformation or breakage; enzymatic cell wall or cell membrane breakage or permeabilization; abrasion or mechanical scarification (e. g., abrasion with carborundum or other particulate abrasive or scarification with a file or sandpaper) or chemical scarification (e. g., treatment with an acid or caustic agent); and electroporation. In certain embodiments, the gRNA- or other polynucleotide-containing composition is provided by bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the gRNA; see, e. g., Broothaerts et al. (2005) *Nature,* 433:629-633. Any of these techniques or a combination thereof are alternatively employed on the plant part or tissue or intact plant (or seed) from which a plant cell or plant protoplast is optionally subsequently obtained or isolated; in certain embodiments, the gRNA- or other polynucleotide (e.g., donor template polynucleotide, polynucleotide encoding a nuclease, or a polynucleotide encoding an ROS scavenging agent)-containing composition is delivered in a separate step after the plant cell or plant protoplast has been obtained or isolated.

In embodiments, a treatment employed in delivery of a polynucleotide including gRNA, a donor template polynucleotide, or a polynucleotide encoding an ROS scavenging agent to a plant cell or plant protoplast is carried out under a specific thermal regime, which can involve one or more appropriate temperatures, e. g., chilling or cold stress (exposure to temperatures below that at which normal plant growth occurs), or heating or heat stress (exposure to temperatures above that at which normal plant growth occurs), or treating at a combination of different temperatures. In certain embodiments, a specific thermal regime is carried out on the plant cell or plant protoplast, or on a plant or plant part from which a plant cell or plant protoplast is subsequently obtained or isolated, in one or more steps separate from the gRNA, the donor template polynucleotide, or the ROS scavenging agent polynucleotide delivery.

In embodiments of the cultures, systems, methods, and compositions provided herein, a whole plant or plant part or seed, or an isolated plant cell or plant protoplast, or the plant or plant part from which a plant cell or plant protoplast is obtained or isolated, is treated with one or more delivery agents which can include at least one chemical, enzymatic, or physical agent, or a combination thereof. In certain embodiments, polynucleotide, e.g., a gRNA-, a donor template polynucleotide-, or a polynucleotide encoding an ROS scavenging agent containing composition further includes one or more one chemical, enzymatic, or physical agents for delivery. In certain embodiments that further include the step of providing an RNA-guided nuclease or a polynucleotide that encodes the RNA-guided nuclease, a gRNA-containing composition including the RNA-guided nuclease or polynucleotide that encodes the RNA-guided nuclease further includes one or more one chemical, enzymatic, or physical agent for delivery. In certain embodiments that further include the step of providing a sequence-specific endonuclease or a polynucleotide that encodes the sequence-specific endonuclease, a donor template polynucleotide-containing composition including the sequence specific endonuclease or polynucleotide that encodes the sequence specific endonuclease can further comprise one or more one chemical, enzymatic, or physical agents for delivery. Treatment with the chemical, enzymatic or physical agent can be carried out simultaneously with the gRNA delivery, with the RNA-guided nuclease delivery, or in one or more separate steps that precede or follow the gRNA delivery or the RNA-guided nuclease delivery. In certain embodiments, a chemical, enzymatic, or physical agent, or a combination of these, is associated or complexed with the polynucleotide composition, with the donor template polynucleotide, with the sequence specific endonuclease or polynucleotide that encodes the sequence specific endonuclease, with the polynucleotide encoding an ROS scavenging agent, with the gRNA or polynucleotide that encodes or is processed to the gRNA, or with the RNA-guided nuclease or polynucleotide that encodes the RNA-guided nuclease; examples of such associations or complexes include those involving non-covalent interactions (e. g., ionic or electrostatic interactions, hydrophobic or hydrophilic interactions, formation of liposomes, micelles, or other heterogeneous composition) and covalent interactions (e. g., peptide bonds, bonds formed using cross-linking agents). In non-limiting examples, a donor template polynucleotide, gRNA or polynucleotide that encodes or is processed to the gRNA is provided as a liposomal complex with a cationic lipid; a gRNA or polynucleotide that encodes or is processed to the gRNA is provided as a complex with a carbon nanotube; and an RNA-guided nuclease is provided as a fusion protein between the nuclease and a cell-penetrating peptide. Examples of agents useful for delivering a donor template polynucleotide, gRNA or polynucleotide that encodes or is processed to the gRNA or a nuclease or polynucleotide that encodes the nuclease include the various cationic liposomes and polymer nanoparticles reviewed by Zhang et al. (2007) *J. Controlled Release,* 123:1-10, and the cross-linked multilamellar liposomes described in US Patent Application Publication 2014/0356414 A 1, incorporated by reference in its entirety herein. In any of the aforementioned embodiments, it is further contemplated that other polynucleotides or polypeptides of interest including: (i) a donor template polynucleotide; (ii) a sequence specific endonuclease or polynucleotide encoding a sequence specific endonuclease; (iii) a combination of (i) and (ii); or (iv) a polynucleotide encoding an ROS scavenging agent can be substituted for the aforementioned gRNA and/or RNA-guided nuclease or polynucleotide encoding the RNA-guided nuclease.

In certain embodiments, the chemical agent can comprise or is at least one selected from the group consisting of:
  (a) solvents (e. g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);
  (b) fluorocarbons (e. g., perfluorodecalin, perfluoromethyldecalin);
  (c) glycols or polyols (e. g., propylene glycol, polyethylene glycol);
  (d) surfactants, including cationic surfactants, anionic surfactants, non-ionic surfactants, and amphiphilic surfactants, e. g., alkyl or aryl sulfates, phosphates, sulfonates, or carboxylates; primary, secondary, or tertiary amines; quaternary ammonium salts; sultaines; betaines; cationic lipids; phospholipids; tallowamine; bile acids such as cholic acid; long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;
(e) lipids, lipoproteins, lipopolysaccharides;
(f) acids, bases, caustic agents;
(g) peptides, proteins, or enzymes (e. g., cellulase, pectolyase, maceroenzyme, pectinase), including cell-penetrating or pore-forming peptides (e. g., (BO100)2K8, Genscript; poly-lysine, poly-arginine, or poly-homoarginine peptides; gamma zein, see US Patent Application publication 2011/0247100, incorporated herein by reference in its entirety; transcription activator of human immunodeficiency virus type 1 ("HIV-1 Tat") and other Tat proteins, see, e. g., www[dot]lifetein[dot]com/Cell_Penetrating_Peptides[dot]html and Järver (2012) *Mol. Therapy-Nucleic Acids,* 1:e27, 1-17); octa-arginine or nona-arginine; poly-homoarginine (see Unnamalai et al. (2004) *FEBS Letters,* 566: 307-310); see also the database of cell-penetrating peptides CPPsite 2.0 publicly available at crdd[dot]osdd[dot]net/raghava/cppsite/
(h) RNase inhibitors;
(i) cationic branched or linear polymers such as chitosan, poly-lysine, DEAE-dextran, polyvinylpyrrolidone ("PVP"), or polyethylenimine ("PEI", e. g., PEI, branched, MW 25,000, CAS #9002-98-6; PEI, linear, MW 5000, CAS #9002-98-6; PEI linear, MW 2500, CAS #9002-98-6);
(j) dendrimers (see, e. g., US Patent Application Publication 2011/0093982, incorporated herein by reference in its entirety);
(k) counter-ions, amines or polyamines (e. g., spermine, spermidine, putrescine), osmolytes, buffers, and salts (e. g., calcium phosphate, ammonium phosphate);
(l) polynucleotides (e. g., non-specific double-stranded DNA, salmon sperm DNA);
(m) transfection agents (e. g., Lipofectin®, Lipofectamine®, and Oligofectamine®, and Invivofectamine® (all from Thermo Fisher Scientific, Waltham, Mass.), PepFect (see Ezzat et al. (2011) *Nucleic Acids Res.,* 39:5284-5298), TransIt® transfection reagents (Mirus Bio, LLC, Madison, Wis.), and poly-lysine, poly-homoarginine, and poly-arginine molecules including octo-arginine and nono-arginine as described in Lu et al. (2010) *J. Agric. Food Chem.,* 58:2288-2294);
(n) antibiotics, including non-specific DNA double-strand-break-inducing agents (e. g., phleomycin, bleomycin, talisomycin); and/or
(o) antioxidants (e. g., glutathione, dithiothreitol, ascorbate).

In embodiments, the chemical agent is provided simultaneously with the polynucleotide (e.g., donor template polynucleotide, gRNA (or polynucleotide encoding the gRNA or that is processed to the gRNA), for example, the polynucleotide composition including the gRNA further includes one or more chemical agent. In certain embodiments, the gRNA or polynucleotide encoding the gRNA or that is processed to the gRNA is covalently or non-covalently linked or complexed with one or more chemical agent; for example, the gRNA or polynucleotide encoding the gRNA or that is processed to the gRNA can be covalently linked to a peptide or protein (e. g., a cell-penetrating peptide or a pore-forming peptide) or non-covalently complexed with cationic lipids, polycations (e. g., polyamines), or cationic polymers (e. g., PEI). In certain embodiments, the gRNA or polynucleotide encoding the gRNA or that is processed to the gRNA is complexed with one or more chemical agents to form, e. g., a solution, liposome, micelle, emulsion, reverse emulsion, suspension, colloid, or gel. In any of the aforementioned embodiments, it is further contemplated that other polynucleotides or polypeptides of interest including: (i) a donor template polynucleotide; (ii) a sequence specific endonuclease or polynucleotide encoding a sequence specific endonuclease; (iii) a combination of (i) and (ii); or (iv) a polynucleotide encoding an ROS scavenging agent can be substituted for the aforementioned gRNA and/or RNA-guided nuclease or polynucleotide encoding the RNA-guided nuclease.

In embodiments, the physical agent (e.g., for delivery of a polynucleotide and/or polypeptide) is at least one selected from the group consisting of particles or nanoparticles (e. g., particles or nanoparticles made of materials such as carbon, silicon, silicon carbide, gold, tungsten, polymers, or ceramics) in various size ranges and shapes, magnetic particles or nanoparticles (e. g., silenceMag Magnetotransfection™ agent, OZ Biosciences, San Diego, Calif.), abrasive or scarifying agents, needles or microneedles, matrices, and grids. In certain embodiments, particulates and nanoparticulates are useful in delivery of the polynucleotide composition or the nuclease or both. Useful particulates and nanoparticles include those made of metals (e. g., gold, silver, tungsten, iron, cerium), ceramics (e. g., aluminum oxide, silicon carbide, silicon nitride, tungsten carbide), polymers (e. g., polystyrene, polydiacetylene, and poly(3,4-ethylenedioxythiophene) hydrate), semiconductors (e. g., quantum dots), silicon (e. g., silicon carbide), carbon (e. g., graphite, graphene, graphene oxide, or carbon nanosheets, nanocomplexes, or nanotubes), and composites (e. g., polyvinylcarbazole/graphene, polystyrene/graphene, platinum/graphene, palladium/graphene nanocomposites). In certain embodiments, such particulates and nanoparticulates are further covalently or non-covalently functionalized, or further include modifiers or cross-linked materials such as polymers (e. g., linear or branched polyethylenimine, poly-lysine), polynucleotides (e. g., DNA or RNA), polysaccharides, lipids, polyglycols (e. g., polyethylene glycol, thiolated polyethylene glycol), polypeptides or proteins, and detectable labels (e. g., a fluorophore, an antigen, an antibody, or a quantum dot). In various embodiments, such particulates and nanoparticles are neutral, or carry a positive charge, or carry a negative charge. Embodiments of compositions including particulates include those formulated, e. g., as liquids, colloids, dispersions, suspensions, aerosols, gels, and solids. Embodiments include nanoparticles affixed to a surface or support, e. g., an array of carbon nanotubes vertically aligned on a silicon or copper wafer substrate. Embodiments include polynucleotide compositions including particulates (e. g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e. g., instruction manual for the Helios® Gene Gun System, Bio-Rad, Hercules, Calif.; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.*, 11:66-71. Other embodiments of useful particulates are nanoparticles, which are generally in the nanometer (nm) size range or less than 1 micrometer, e. g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, Mo.) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e. g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments include polynucleotide compositions including materials such as gold, silicon, cerium, or carbon, e. g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e. g., carbon nanotubes functionalized with amide, amino, carboxylic acid, sulfonic acid, or polyethylene glycol moeities), and graphene or graphene oxide or graphene complexes; see, for example, Wong et al. (2016) *Nano Lett.*, 16:1161-1172; Giraldo et al. (2014) *Nature Materials*, 13:400-409; Shen et al. (2012) *Theranostics*, 2:283-294; Kim et al. (2011) *Bioconjugate Chem.*, 22:2558-2567; Wang et al. (2010) *J Am. Chem. Soc. Comm.*, 132: 9274-9276; Zhao et al. (2016) *Nanoscale Res. Lett.*, 11:195-203; and Choi et al. (2016) *J. Controlled Release*, 235:222-235. See also, for example, the various types of particles and nanoparticles, their preparation, and methods for their use, e.g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In embodiments wherein the polynucleotide (e.g., gRNA (or polynucleotide encoding the gRNA) a donor template polynucleotide, polynucleotide encoding a sequence specific endonuclease, or a polynucleotide encoding an ROS scavenging agent) is provided in a composition that further includes an RNA-guided nuclease (or a polynucleotide that encodes the RNA-guided nuclease), or wherein the method further includes the step of providing an RNA-guided nuclease or a polynucleotide that encodes the RNA-guided nuclease, one or more one chemical, enzymatic, or physical agent can similarly be employed. In certain embodiments, the RNA-guided nuclease (or polynucleotide encoding the RNA-guided nuclease) is provided separately, e. g., in a separate composition including the RNA-guided nuclease or polynucleotide encoding the RNA-guided nuclease. Such compositions can include other chemical or physical agents (e. g., solvents, surfactants, proteins or enzymes, transfection agents, particulates or nanoparticulates), such as those described above as useful in the polynucleotide composition used to provide the gRNA. For example, porous silica nanoparticles are useful for delivering a DNA recombinase into maize cells; see, e. g., Martin-Ortigosa et al. (2015) *Plant Physiol.*, 164:537-547. In an embodiment, the polynucleotide composition includes a gRNA and Cas9 nuclease, and further includes a surfactant and a cell-penetrating peptide. In an embodiment, the polynucleotide composition includes a plasmid that encodes both an RNA-guided nuclease and at least on gRNA, and further includes a surfactant and carbon nanotubes. In an embodiment, the polynucleotide composition includes multiple gRNAs and an mRNA encoding the RNA-guided nuclease, and further includes particles (e.g., gold or tungsten particles), and the polynucleotide composition is delivered to a plant cell or plant protoplast by Biolistics. In any of the aforementioned embodiments, it is further contemplated that other polynucleotides or polypeptides of interest including: (i) a donor template polynucleotide; (ii) a sequence specific endonuclease or polynucleotide encoding a sequence specific endonuclease; (iii) a combination of (i) and (ii); or (iv) a polynucleotide encoding an ROS scavenging agent can be substituted for the aforementioned gRNA and/or RNA-guided nuclease or polynucleotide encoding the RNA-guided nuclease.

In related embodiments, one or more chemical, enzymatic, or physical agent(s) can be used in one or more steps separate from (preceding or following) that in which the polynucleotide (e.g., gRNA, a donor template polynucleotide, polynucleotide encoding a sequence specific endonuclease, or a polynucleotide encoding an ROS scavenging agent) is provided. In an embodiment, the plant or plant part from which a plant cell or plant protoplast is obtained or isolated is treated with one or more one chemical, enzymatic, or physical agent in the process of obtaining or isolating the plant cell or plant protoplast. In certain embodiments, the plant or plant part is treated with an abrasive, a caustic agent, a surfactant such as Silwet L-77 or a cationic lipid, or an enzyme such as cellulase.

In embodiments, a polynucleotide, including a gRNA, a donor template polynucleotide, polynucleotide encoding a sequence specific endonuclease, or a polynucleotide encoding an ROS scavenging agent, is delivered to plant cells or plant protoplasts prepared or obtained from a plant, plant part, or plant tissue that has been treated with the polynucleotide compositions (and optionally the nuclease). In certain embodiments, one or more one chemical, enzymatic, or physical agent, separately or in combination with the polynucleotide composition, is provided/applied at a location in the plant or plant part other than the plant location, part, or tissue from which the plant cell or plant protoplast is obtained or isolated. In certain embodiments, the polynucleotide composition is applied to adjacent or distal cells or tissues and is transported (e. g., through the vascular system or by cell-to-cell movement) to the meristem from which plant cells or plant protoplasts are subsequently isolated. In certain embodiments, a gRNA-containing composition is applied by soaking a seed or seed fragment or zygotic or somatic embryo in the gRNA-containing composition, whereby the gRNA is delivered to the seed or seed fragment or zygotic or somatic embryo from which plant cells or plant protoplasts are subsequently isolated. In certain embodiments, a flower bud or shoot tip is contacted with a gRNA-containing composition, whereby the gRNA is delivered to cells in the flower bud or shoot tip from which plant cells or plant protoplasts are subsequently isolated. In certain embodiments, a gRNA-containing composition is applied to the surface of a plant or of a part of a plant (e. g., a leaf surface), whereby the gRNA is delivered to tissues of the plant from which plant cells or plant protoplasts are subsequently isolated. In certain embodiments a whole plant or plant tissue is subjected to particle- or nanoparticle-mediated delivery (e. g., Biolistics or carbon nanotube or nanoparticle delivery) of a gRNA-containing composition, whereby the gRNA is delivered to cells or tissues from which plant cells or plant protoplasts are subsequently isolated. In any of the aforementioned embodiments, it is further contemplated that other polynucleotides or polypeptides of interest including: (i) a donor template polynucleotide; (ii) a sequence specific endonuclease or polynucleotide encoding a sequence specific endonuclease; (iii) a combination of (i) and (ii); or (iv) a polynucleotide encoding an ROS scavenging agent can be substituted for the aforementioned gRNA and/or RNA-guided nuclease or polynucleotide encoding the RNA-guided nuclease.

EMBODIMENTS

Various embodiments of the cultures, systems, methods, and compositions provided herein are included in the following non-limiting list of embodiments.

Embodiment 1. A plant protoplast culture comprising:
(a) at least one plant protoplast; and
(b) a culture medium comprising: (i) at least 40 millimolar $Ca^{2+}$ or $Mg^{2+}$; (ii) an antioxidant; or (iii) a combination of (i) and (ii).

Embodiment 2. The plant protoplast culture of embodiment 1, wherein the plant protoplast is obtained from a plant tissue, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, ovule, pollen, microspore, anther, hypocotyl, cotyledon, leaf, petiole, stem, tuber, root, callus, or plant cell suspension.

Embodiment 3. The plant protoplast culture of any one of embodiments 1 to 2, wherein the plant protoplast is obtained from (a) a monocot plant, or (b) a dicot plant.

Embodiment 4. The plant protoplast culture of any one of embodiments 1 to 3, wherein the plant protoplast is haploid, diploid, or polyploid.

Embodiment 5. The plant protoplast culture of any one of embodiments 1 to 4, wherein the plant protoplast is obtained from alfalfa (*Medicago sativa*), almonds (*Prunus dulcis*), apples (*Malus×domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum* usitatissumum L.), geraniums (*Pelargonium* spp.), grapefruit (*Citrus×paradisi*), grapes (*Vitus* spp.) including wine grapes (*Vitus vinifera*), guava (*Psidium guajava*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria×ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), or yams (*Discorea* spp.).

Embodiment 6. The plant protoplast culture of any one of embodiments 1 to 5, wherein the plant protoplast is: (a) encapsulated in a polymer, or (b) encapsulated in a vesicle or liposome, or (c) not encapsulated.

Embodiment 7. The plant protoplast culture of any one of embodiments 1 to 6, wherein the culture medium is liquid.

Embodiment 8. The plant protoplast culture of any one of embodiments 1 to 7, wherein the culture medium comprises:
(a) at least 40 millimolar $Ca^{2+}$;
(b) at least 50 millimolar $Ca^{2+}$;
(c) at least 100 millimolar $Ca^{2+}$;
(d) at least 40 millimolar $Mg^{2+}$;
(e) at least 50 millimolar $Mg^{2+}$; or
(f) at least 100 millimolar $Mg^{2+}$.

Embodiment 9. The plant protoplast culture of any one of embodiments 1 to 8, wherein the antioxidant is a low-molecular-weight thiol.

Embodiment 10. The plant protoplast culture of any one of embodiments 1 to 8, wherein the antioxidant is glutathione, dithiothreitol, N-acetylcysteine, lipoic acid, ascorbic acid, tocopherols, butylated hydroxytoluene, butylated hydroxyanisole, or a combination of these.

Embodiment 11. The plant protoplast culture of embodiment 9 or 10, wherein the culture medium comprises at least 1 millimolar glutathione.

Embodiment 12. The plant protoplast culture of any one of embodiments 1 to 11, wherein the culture is subjected to hypoxic conditions.

Embodiment 13. The plant protoplast culture of embodiment 12, wherein the hypoxic conditions comprise:
(a) about one-half normal atmospheric oxygen concentrations;
(b) about 10% oxygen by volume; or
(c) about 5% oxygen by volume.

Embodiment 14. The plant protoplast culture of any one of embodiments 1 to 13, wherein protoplast viability, when compared to a control plant protoplast culture without (i) at least 40 millimolar $Ca^{2+}$ or $Mg^{2+}$; (ii) an antioxidant; or (iii) a combination of (i) and (ii), is:
(a) at least 10% higher after 30 hours' culture;
(b) at least 10% higher after 48 hours' culture;
(c) at least 10% higher after 72 hours' culture; or
(d) at least 10% higher after 96 hours' culture.

Embodiment 15. The plant protoplast culture of any one of embodiments 1 to 14, wherein the culture medium comprises at least 100 millimolar $Ca^{2+}$, wherein the plant protoplast is obtained from maize, and wherein protoplast viability, when compared to a control plant protoplast culture without at least 100 millimolar $Ca^{2+}$, is at least 20% higher after 64 hours' culture.

Embodiment 16. The plant protoplast culture of any one of embodiments 1 to 14, wherein the culture medium comprises at least 1 millimolar low-molecular-weight thiol, wherein the plant protoplast is obtained from maize, and wherein protoplast viability, when compared to a control plant protoplast culture without at least 1 millimolar low-molecular-weight thiol, is at least 10% higher after 64 hours' culture.

Embodiment 17. A method of improving viability of a plant protoplast, comprising including in the culture conditions of the protoplast at least one of:
  (a) at least 40 millimolar $Ca^{2+}$ or $Mg^{2+}$; and
  (b) at least 1 millimolar low-molecular-weight thiol.

Embodiment 18. The method of embodiment 17, wherein the culture conditions of the protoplast comprise hypoxic conditions.

Embodiment 19. The method of embodiment 17 or 18, wherein the hypoxic conditions comprise:
  (a) about one-half normal atmospheric oxygen concentrations;
  (b) about 10% oxygen by volume; or
  (c) about 5% oxygen by volume.

Embodiment 20. The method of embodiment 17 or 18, wherein the viability of a plant protoplast, when compared to that of a control protoplast cultured without at least one of (i) at least 40 millimolar $Ca^{2+}$ or $Mg^{2+}$; and (ii) at least 1 millimolar low-molecular-weight thiol, is improved by:
  (a) at least 10% over at least 24 hours' culture;
  (b) at least 10% over at least 48 hours' culture;
  (c) at least 10% over at least 72 hours' culture;
  (d) at least 10% over at least 96 hours' culture.

Embodiment 21. The method of embodiment 18, wherein the plant protoplast exhibits an improved cell division rate.

Embodiment 22. A protoplast having improved viability, provided by the method of any one of embodiments 17 to 21.

Embodiment 23. Multiple protoplasts or cells, callus, a somatic embryo, or a regenerated plant, grown from the protoplast of embodiment 22.

Embodiment 24. A composition comprising:
  (a) at least one protoplast having improved viability, provided by the method of any one of embodiments 17 to 21;
  (b) at least one effector molecule for inducing a genetic alteration in the plant cell or plant protoplast, wherein the at least one effector molecule is selected from the group consisting of: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (iii) a polynucleotide encoding one or more nucleases capable of effecting site-specific alteration of a target nucleotide sequence; and
  (c) optionally, at least one delivery agent selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; and antioxidants; particles or nanoparticles, magnetic particles or nanoparticles, abrasive or scarifying agents, needles or microneedles, matrices, and grids.

Embodiment 25. An array comprising a plurality of containers, each comprising at least one protoplast having improved viability, provided by the method of any one of embodiments 17 to 21.

Embodiment 26. A method of improving the cell division rate of a plant protoplast culture, wherein the culture conditions comprise hypoxic conditions.

Embodiment 27. The method of embodiment 26, wherein the hypoxic conditions comprise:
  (a) about one-half normal atmospheric oxygen concentrations;
  (b) about 10% oxygen by volume; or
  (c) about 5% oxygen by volume.

Embodiment 28. The method of embodiment 26 or 27, wherein the culture conditions further comprise at least 40 millimolar $Ca^{2+}$ or $Mg^{2+}$.

Embodiment 29. A method for making a plant cell having a genomic modification comprising:
  (a) providing genome editing molecules to a plant cell previously, concurrently, or subsequently exposed to a hypoxic condition, a reactive oxygen species (ROS) concentration lowering agent, or combination thereof; wherein the molecules comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) a polynucleotide encoding a sequence-specific endonuclease and a donor template polynucleotide; or (v) any combination thereof, to modify the plant cell's genome; and,
  (b) isolating or propagating a plant cell comprising the genome modification, thereby making the plant cell having a genomic modification.

Embodiment 30. The method of embodiment 29, further comprising obtaining callus, a propagule, or a plant from the isolated or propagated plant cell of step (b) comprising the genome modification, wherein the callus, propagule, or plant comprises a genome modified by the molecule(s) and wherein the propagule is optionally a seed.

Embodiment 31. A method for producing a plant having a genomic modification comprising:
  (a) providing genome editing molecules to a plant cell previously, concurrently, or subsequently exposed to a hypoxic condition, a reactive oxygen species (ROS) concentration lowering agent, or combination thereof, wherein the molecules comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) a polynucleotide encoding a sequence-specific endonuclease and a donor template polynucleotide; or (v) any combination thereof, to modify the plant cell's genome;

(b) isolating or propagating a plant cell comprising the genome modification; and, (c) regenerating or obtaining a plant comprising the genome modification from the plant cell, thereby producing a plant having the having a genomic modification.

Embodiment 32. The method of embodiment 31, further comprising harvesting seed from the plant, propagating the plant, or multiplying the plant.

Embodiment 33. The method of any one of embodiments 29 to 32, wherein the ROS concentration lowering agent is an ROS scavenging agent.

Embodiment 34. The method of any one of embodiments 29 to 32, wherein the plant cell is exposed by: (i) contacting the plant cell with the ROS concentration lowering agent; or (ii) introducing at least one of the ROS concentration lowering agents into the plant cell.

Embodiment 35. The method of any one of embodiments 29 to 32, wherein ROS concentration lowering agent is introduced into the plant cell by direct application, transfection, electroporation, transformation, *Agrobacterium*-mediated delivery, viral vector mediated delivery, by contacting or fusing the plant cell with a donor plant cell that comprises the agent, by crossing the plant comprising the plant cell to a donor plant that comprises the agent, or any combination thereof.

Embodiment 36. The method of embodiment 35, wherein the donor plant cell or donor plant that comprises the ROS concentration lowering agent is stably or transiently transformed with a polynucleotide encoding the agent.

Embodiment 37. The method of any one of embodiments 29 to 32, wherein the genome editing molecule(s) are provided to the plant cell by introducing the molecule(s) into the plant cell by direct application, transfection, electroporation, transformation, *Agrobacterium*-mediated delivery, viral vector mediated delivery, by fusing or contacting the plant cell with another plant cell that comprises the agent, by crossing the plant comprising the plant cell to a plant that comprises the molecules, or any combination thereof.

Embodiment 38. The method of any one of embodiments 29 to 32, wherein the plant cell exposed to the hypoxiccondition or ROS concentration lowering agent: (i) contains the RNA-guided nuclease or contains one or more polynucleotides encoding an RNA-guided nuclease and is associated with and/or contacts the guide RNA; or (ii) contains the sequence-specific endonuclease or contains one or more polynucleotides encoding a sequence-specific endonuclease and is associated with and/or contacts the donor template polynucleotide.

Embodiment 39. A system for producing a plant cell having a genomic modification comprising: (a) a plant cell subjected to a hypoxic condition, or treated with a reactive oxygen species (ROS) scavenging agent, or both subjected to the hypoxic condition and treated with the ROS scavenging agent; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the molecule(s).

Embodiment 40. A system for producing a plant cell having a genomic modification comprising: (a) a plant cell wherein a reactive oxygen species (ROS) concentration is lowered in comparison to a control plant cell; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the molecule(s).

Embodiment 41. The system of embodiment 40, wherein the ROS concentration is lowered by treating the cell with an exogenously provided ROS scavenging agent and/or subjecting the cell to a hypoxic condition.

Embodiment 42. A composition comprising: (a) (i) a plant cell subjected to a hypoxic condition, or treated with an exogenous reactive oxygen species (ROS) scavenging agent, or both subjected to the hypoxic condition and treated with the ROS scavenging agent; or (ii) a plant cell or plant cell subjected to a hypoxic condition and an exogenous ROS scavenging agent; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the molecule(s).

Embodiment 43. A composition comprising: (a) a plant cell wherein a reactive oxygen species (ROS) concentration is lowered in comparison to a control plant cell; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the agent and the molecule(s).

Embodiment 44. The composition of embodiment 43, wherein the ROS concentration is lowered by treating the cell with an exogenous ROS scavenging agent, by subjecting the cell to a hypoxic condition, or wherein the composition or plant cell comprises an exogenous ROS scavenging agent.

Embodiment 45. The method of any one of embodiments 29 to 32, system of embodiment 39 or 41, or composition of embodiment 42 or 44, wherein the ROS concentration lowering agent or ROS scavenging agent comprises a non-enzymatic ROS scavenging agent.

Embodiment 46. The method, system or composition of embodiment 45, wherein the non-enzymatic ROS scavenging agent is ascorbic acid, a low-molecular-weight thiol, a pro-thiol, a tocopherol, a carotenoid, a flavonoid, or combination thereof.

Embodiment 47. The method of any one of embodiments 29 to 32, system of embodiment 39 or 41, or composition of embodiment 42 or 44, wherein the ROS concentration lowering agent or the ROS scavenging agent comprises an enzymatic ROS scavenging agent.

Embodiment 48. The method of embodiment 47, wherein the enzymatic ROS scavenging agent comprises a catalase, an ascorbate peroxidase, a dehydroascorbate reductase, guaiacol peroxidase, monodehydroascorbate reductase, a peroxidase, a superoxide dismutase, or a combination thereof.

Embodiment 49. The method of any one of embodiments 29 to 32, system of embodiment 39 or 41, or composition of embodiment 42 or 44, wherein the ROS concentration lowering agent or the ROS scavenging agent comprises a combination of at least one enzymatic and at least one non-enzymatic ROS scavenging agent.

Embodiment 50. The method of any one of embodiments 29 to 32, system of embodiment 39 or 41, or composition of embodiment 42 or 44, wherein the cell comprises an exogenous polynucleotide that produces the ROS concentration lowering agent or ROS scavenging agent in the cell.

Embodiment 51. The method of any one of embodiments 29 to 32, system of any one of embodiments 39 to 41, or composition of any one of embodiments 42 to 44, wherein: (i) the hypoxic condition comprises maintaining the cell in air comprising an oxygen concentration of about 12% to about 5% oxygen by volume; or (ii) the ROS concentration is lowered by maintaining the cell in air comprising an oxygen concentration of about 12% to about 5% oxygen by volume.

Embodiment 52. The method of any one of embodiments 29 to 32, system of any one of embodiments 39 to 41, or composition of any one of embodiments 42 to 44, wherein the cell is in a liquid culture media and wherein the hypoxic growth condition or hypoxic condition comprises maintaining the cell and the media in air comprising an oxygen concentration of about 12% to about 5% oxygen by volume or wherein the ROS level is lowered by maintaining the cell and the media in air comprising an oxygen concentration of about 12% to about 5% oxygen by volume.

Embodiment 53. The method of any one of embodiments 29 to 32, system of any one of embodiments 39 to 41, or composition of any one of embodiments 42 to 44, wherein the hypoxic condition comprises maintaining the cell in a liquid culture media having a dissolved oxygen concentration that is lowered in comparison to a dissolved oxygen concentration of liquid culture media kept under an oxygen concentration of 20% by volume or wherein the ROS concentration is lowered by maintaining the cell in a liquid culture media having a dissolved oxygen concentration that is lowered in comparison to a dissolved oxygen concentration of liquid culture media kept under an oxygen concentration of 20% by volume.

Embodiment 54. The method of any one of embodiments 29 to 32, system of any one of embodiments 39 to 41, or composition of any one of embodiments 42 to 44, wherein the hypoxic condition or hypoxic condition is induced by treating the cell with a hypoxia mimetic, wherein the ROS concentration is lowered by treating the cell with a hypoxia mimetic, or wherein the composition comprises an exogenous hypoxia mimetic.

Embodiment 55. The method of any one of embodiments 29 to 32, system of any one of embodiments 39 to 41, or composition of any one of embodiments 42 to 44, wherein the concentration of more than one ROS is lowered.

Embodiment 56. The method of any one of embodiments 29 to 32, system of any one of embodiments 39 to 41, or composition of any one of embodiments 42 to 44, wherein the ROS is hydrogen peroxide, a superoxide radical, a peroxide ion, a hydroperoxyl radical, or a hydroxyl radical.

Embodiment 57. The method of any one of embodiments 29 to 32, system of any one of embodiments 39 to 41, or composition of any one of embodiments 42 to 44, wherein the plant cell is in culture media, in a plant, or in a plant tissue.

Embodiment 58. The method of any one of embodiments 29 to 32, system of any one of embodiments 39 to 41, or composition of any one of embodiments 42 to 44, wherein the plant cell is part of a callus culture, an embryogenic callus culture, or an embryo.

Embodiment 59. The method of any one of embodiments 29 to 32, system of any one of embodiments 39 to 41, or composition of any one of embodiments 42 to 44, wherein the plant cell is a plant protoplast, a mature pollen cell, a microspore, or a megaspore.

Embodiment 60. The method of any one of embodiments 29 to 32, system of any one of embodiments 39 to 41, or composition of any one of embodiments 42 to 44, wherein the genome editing molecule(s) can provide for a substitution or deletion of a single nucleotide residue in an endogenous gene of the plant cell.

Embodiment 61. The method of any one of embodiments 29 to 32, system of any one of embodiments 39 to 41, or composition of any one of embodiments 42 to 44, wherein frequency of the genome modification is increased in comparison to a control method wherein a control plant cell is not exposed to a ROS concentration lowering agent, a ROS scavenging agent, or a hypoxic condition.

Embodiment 62. The method of any one of embodiments 29 to 32, system of any one of embodiments 39 to 41, or composition of any one of embodiments 42 to 44, wherein a frequency of homology directed repair (HDR) of a target gene in the plant cell is increased by at least 1.1-fold in comparison to a control composition comprising the genome editing molecules, wherein: (i) a control plant cell of the control composition is not subjected to the hypoxic condition, is not treated with the ROS scavenging agent, or wherein the ROS scavenging agent is absent; or (ii) ROS concentrations are not lowered in a control plant cell of the control composition.

Embodiment 63. The method of any one of embodiments 29 to 32, system of any one of embodiments 39 to 41, or composition of any one of embodiments 42 to 44, wherein the plant cell is a monocot plant cell.

Embodiment 64. The method, system, or composition of embodiment 63, wherein the monocot plant cell is a barley, maize, millet, oat, rice, rye, sorghum, or wheat plant cell.

Embodiment 65. The method of any one of embodiments 29 to 32, system of any one of embodiments 39 to 41, or composition of any one of embodiments 42 to 44, wherein the plant cell is a dicot plant cell.

Embodiment 66. The method, system, or composition of embodiment 65, wherein the dicot plant cell is an alfalfa, canola, oilseed rape, cotton, flax, potato, soybean, or tomato plant cell.

Embodiment 67. The method of any one of embodiments 29 to 32, system of any one of embodiments 39 to 41, or composition of any one of embodiments 42 to 44, wherein the RNA-guided nuclease comprises an RNA-guided DNA endonuclease, a type II Cas nuclease, a Cas9 nuclease, a type V Cas nuclease, a Cpf1 nuclease, a CasY nuclease, a CasX nuclease, a C2c1 nuclease, a C2c3 nuclease, or an engineered nuclease.

Embodiment 68. The method of any one of embodiments 29 to 32, system of any one of embodiments 39 to 41, or composition of any one of embodiments 42 to 44, wherein the sequence-specific endonuclease comprises a zinc-finger nuclease (ZFN), a transcription activator-like effector nuclease (TAL-effector nuclease), Argonaute, a meganuclease, or engineered meganuclease.

Embodiment 69. The method of any one of embodiments 29 to 32, system of any one of embodiments 39 to 41, or composition of any one of embodiments 42 to 44, wherein the ROS concentration lowering agent or the ROS scavenging agent is heterologous to the plant cell and/or wherein the genome editing molecule(s) are heterologous to the plant cell.

Embodiment 70. The method of any one of embodiments 29 to 32, system of any one of embodiments 39 to 41, or composition of any one of embodiments 42 to 44, wherein the ROS concentration lowering agent is an exogenous ROS concentration lowering agent or the ROS scavenging agent is an exogenous ROS scavenging agent and/or wherein the genome editing molecule(s) are exogenous genome editing molecule(s).

Embodiment 71. The method of any one of embodiments 29 to 32, system of any one of embodiments 39 to 41, or composition of any one of claims 42 to 44, wherein $Ca^{2+}$ and/or $Mg^{2+}$ are provided at a concentration of about 40 mM to 150 mM.

Embodiment 72. A plant cell culture comprising:
(a) a plant cell culture medium;
(b) a plant cell exposed to a hypoxic condition, or to a reactive oxygen species (ROS) concentration lowering agent, or to a combination thereof, wherein the plant cell is contained or supported by the plant cell culture medium; and,
(c) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the molecule(s).

Embodiment 73. The plant cell culture of embodiment 72, wherein the hypoxic condition comprises exposing the plant cell to an atmosphere comprising an oxygen concentration of about 12% to about 5% oxygen by volume.

Embodiment 74. The plant cell culture of embodiment 72 or 73, wherein the ROS concentration lowering agent is a ROS scavenging agent.

Embodiment 75. The plant cell culture of embodiment 74, wherein the ROS scavenging agent is ascorbic acid, a low-molecular-weight thiol, a pro-thiol, a tocopherol, a carotenoid, a flavonoid, or combination thereof.

Embodiment 76. The plant cell culture of any one of embodiments 72, 73, 74, or 75, wherein a frequency of homology directed repair (HDR) of a target gene in the plant cell is increased by at least 2-fold in comparison to a control plant cell culture provided with the genome editing molecules and plant cells not exposed to a hypoxic condition, or to a reactive oxygen species (ROS) concentration lowering agent, or to a combination thereof.

Embodiment 77. The plant cell culture of any one of embodiments 72, 73, 74, 75, or 76, wherein $Ca^{2+}$ and/or $Mg^{2+}$ is provided at a concentration of about 40 mM to 150 mM in the plant cell culture medium.

Embodiment 78. A method for making a plant cell having a genomic modification comprising:
(a) providing genome editing molecules to a plant cell previously, concurrently, or subsequently subjected to a hypoxic condition, or to a reactive oxygen species (ROS) concentration lowering agent, or to a combination thereof; wherein the molecules comprise: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) a polynucleotide encoding a sequence-specific endonuclease and a donor template polynucleotide; or (v) any combination thereof, to modify the plant cell's genome; and,
(b) isolating, selecting, identifying, and/or propagating a plant cell comprising the genome modification, thereby making the plant cell having a genomic modification.

Embodiment 79. The method of embodiment 78, further comprising obtaining callus, a propagule, or a plant from the isolated, selected, identified, and/or propagated plant cell of step (b) comprising the genome modification, wherein the callus, propagule, or plant comprises a genome modified by the molecule(s) and wherein the propagule is optionally a seed.

Embodiment 80. The method of embodiment 78 or 79, wherein the hypoxic condition comprises maintaining a plant, plant tissue, plant part, or plant cell culture containing the plant cell under an atmosphere comprising an oxygen concentration of about 12% to about 5% oxygen by volume.

Embodiment 81. The method of any one of embodiments 78, 79, or 80, wherein the ROS concentration lowering agent is a ROS scavenging agent.

Embodiment 82. The method of embodiment 81, wherein the ROS scavenging agent is ascorbic acid, a low-molecular-weight thiol, a pro-thiol, a tocopherol, a carotenoid, a flavonoid, or combination thereof.

Embodiment 83. The method of any one of embodiments 78, 79, 80, 81, or 82, wherein a frequency of homology directed repair (HDR) of a target gene in the plant cell of step (a) is increased by at least 2-fold in comparison to a control plant cell provided with the genome editing molecules and is not exposed to a hypoxic condition, or to a reactive oxygen species (ROS) concentration lowering agent, or to a combination thereof.

Embodiment 84. The method of any one of embodiments 78, 79, 80, 81, 82, or 83, wherein the plant cell in at least step (a) is contained or supported by a plant cell culture medium and $Ca^{2+}$ and/or $Mg^{2+}$ is provided in the plant cell culture medium at a concentration of about 40 mM to 150 mM.

Embodiment 85. The method of any one of embodiments 78, 79, 80, 81, 82, 83, or 84, wherein: (i) the hypoxic condition comprises maintaining a plant, plant tissue, plant part, or plant cell culture containing the plant cell under an atmosphere comprising an oxygen concentration of about 12% to about 5% oxygen by volume; (ii) the ROS lowering agent is ascorbic acid, a low-molecular-weight thiol, a pro-thiol, a tocopherol, a carotenoid, a flavonoid, or combination thereof; and/or (iii) $Ca^{2+}$ and/or $Mg^{2+}$ is provided at a concentration of about 40 mM to 150 mM to the plant cell in at least step (a).

Embodiment 86. A system for producing a plant cell having a genomic modification comprising: (a) a plant cell subjected to a hypoxic condition, or treated with a reactive oxygen species (ROS) scavenging agent, or both subjected to the hypoxic condition and treated with the ROS scavenging agent; and (b) genome editing molecule(s) comprising: (i) an RNA-guided nuclease and a guide RNA and optionally a donor template polynucleotide; (ii) a sequence-specific endonuclease and a donor template polynucleotide; (iii) one or more polynucleotides encoding an RNA-guided nuclease and a guide RNA and optionally a donor template polynucleotide; (iv) one or more polynucleotide(s) encoding a sequence-specific endonuclease and a donor template polynucleotide; or (v) any combination thereof; wherein the plant cell is associated with, contacts, and/or contains the molecule(s).

Embodiment 87. The system of embodiment 86, wherein the hypoxic condition comprises exposing a plant, plant tissue, plant part, or plant cell culture containing the plant cell to an oxygen concentration of about 12% to about 5% oxygen by volume.

Embodiment 88. The system of embodiment 86 or 87, wherein the ROS concentration lowering agent is an ROS scavenging agent.

Embodiment 89. The system of any one of embodiments 86, 87, or 88, wherein the ROS scavenging agent is ascorbic acid, a low-molecular-weight thiol, a pro-thiol, a tocopherol, a carotenoid, a flavonoid, or combination thereof.

Embodiment 90. The system of any one of embodiments 86, 87, 88, or 89, wherein a frequency of homology directed repair (HDR) of a target gene in the plant cell is increased by at least 1.1-fold in comparison to a control plant cell culture comprising the genome editing molecules wherein a control plant cell is not subjected to a hypoxic growth condition and/or a ROS scavenging agent is absent.

Embodiment 91. The system of any one of embodiments 86, 87, 88, 89, or 90, wherein the plant cell is contained or supported by a plant cell culture medium and $Ca^{2+}$ and/or $Mg^{2+}$ is provided at a concentration of about 40 mM to 150 mM in the plant cell culture medium.

EXAMPLES

Example 1

This example illustrates techniques for preparing a plant cell or plant protoplast useful in compositions and methods of the disclosure. More specifically this non-limiting example describes techniques for preparing isolated, viable plant protoplasts from monocot and dicot plants.

The following mesophyll protoplast preparation protocol (modified from one publicly available at molbio[dot]mgh [dot]harvard.edu/sheenweb/protocols_reg[dot]html) is generally suitable for use with monocot plants such as maize (*Zea mays*) and rice (*Oryza sativa*):

Prepare an enzyme solution containing 0.6 molar mannitol, 10 millimolar MES pH 5.7, 1.5% cellulase R10, and 0.3% macerozyme R10. Heat the enzyme solution at 50-55 degrees Celsius for 10 minutes to inactivate proteases and accelerate enzyme solution and cool it to room temperature before adding 1 millimolar $CaCl_2$, 5 millimolar β-mercaptoethanol, and 0.1% bovine serum albumin. Pass the enzyme solution through a 0.45 micrometer filter. Prepare a washing solution containing 0.6 molar mannitol, 4 millimolar MES pH 5.7, and 20 millimolar KCl.

Obtain second leaves of the monocot plant (e. g., maize or rice) and cut out the middle 6-8 centimeters. Stack ten leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of washing buffer. Measure the concentration of protoplasts using a hemocytometer and adjust the concentration to $2 \times 10^5$ protoplasts/milliliter with washing buffer.

The following mesophyll protoplast preparation protocol (modified from one described by Niu and Sheen (2012) *Methods Mol. Biol.*, 876:195-206, doi: 10.1007/978-1-61779-809-2_16) is generally suitable for use with dicot plants such as *Arabidopsis thaliana* and brassicas such as kale (*Brassica oleracea*).

Prepare an enzyme solution containing 0.4 M mannitol, 20 millimolar KCl, 20 millimolar MES pH 5.7, 1.5% cellulase R10, and 0.4% macerozyme R10. Heat the enzyme solution at 50-55 degrees Celsius for 10 minutes to inactivate proteases and accelerate enzyme solution, and then cool it to room temperature before adding 10 millimolar $CaCl_2$), 5 millimolar β-mercaptoethanol, and 0.1% bovine serum albumin. Pass the enzyme solution through a 0.45 micrometer filter. Prepare a "W5" solution containing 154 millimolar NaCl, 125 millimolar $CaCl_2$, 5 millimolar KCl, and 2 millimolar MES pH 5.7. Prepare a "MMg solution" solution containing 0.4 molar mannitol, 15 millimolar $MgCl_2$, and 4 millimolar MES pH 5.7.

Obtain second or third pair true leaves of the dicot plant (e. g., a *brassica* such as kale) and cut out the middle section. Stack 4-8 leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri dish with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of MMg solution. Measure the concentration of protoplasts using a hemocytometer and adjust the concentration to $2 \times 10^5$ protoplasts/milliliter with MMg solution.

Example 2

This example illustrates culture conditions effective in improving viability of plant cells or plant protoplasts. More specifically, this non-limiting example describes media and culture conditions for improving viability of isolated plant protoplasts.

Table 1 provides the compositions of different liquid basal media suitable for culturing plant cells or plant protoplasts; final pH of all media was adjusted to 5.8 if necessary.

TABLE 1*

| Component | Concentration (mg/L unless otherwise noted) | | | | |
|---|---|---|---|---|---|
| | SH | 8p | PIM | P2 | YPIM B- |
| Casamino acids | | 250 | | | |
| Coconut water | | 20000 | | | |
| Ascorbic acid | | 2 | | | |
| biotin | | 0.01 | 0.01 | | |
| Cholicalciferol (Vitamin D-3) | | 0.01 | | | |
| choline chloride | | 1 | | | |
| Citric acid | | 40 | | | |
| Cyanocobalamin (Vitamin B-12) | | 0.02 | | | |
| D-calcium pantothenate | | 1 | 1 | | |
| D-Cellobiose | | 250 | | | |
| D-Fructose | | 250 | | | |
| D-Mannose | | 250 | | | |
| D-Ribose | | 250 | | | |
| D-Sorbitol | | 250 | | | |
| D-Xylose | | 250 | | | |
| folic acid | | 0.4 | 0.2 | | |
| Fumaric acid | | 40 | | | |
| L-Malic acid | | 40 | | | |
| L-Rhamnose | | 250 | | | |
| p-Aminobenzoic acid | | 0.02 | | | |
| Retinol (Vitamin A) | | 0.01 | | | |
| Riboflavin | | 0.2 | | | |
| Sodium pyruvate | | 20 | | | |
| 2,4-D | 0.5 | 0.2 | 1 | 5 | 1 |
| 6-benzylaminopurine (BAP) | | | | | 1 |
| Indole-3-butyric acid (IBA) | | | | 2.5 | |
| Kinetin | 0.1 | | | | |
| Naphthaleneacetic acid (NAA) | | 1 | | | |
| parachlorophenoxyacetate (pCPA) | 2 | | | | |
| Thidiazuron | | | 0.022 | | |
| Zeatin | | 0.5 | | | |
| AlCl3 | | | 0.03 | | |
| Bromocresol purple | | | 8 | | |
| $CaCl_2 \cdot 2H_2O$ | 200 | 600 | 440 | 200 | 440 |
| $CoCl_2 \cdot 6H_2O$ | 0.1 | 0.025 | | 0.1 | |
| $CuSO_4 \cdot 5H_2O$ | 0.2 | 0.025 | 0.03 | 0.2 | 0.03 |
| D-Glucose | | 68400 | 40000 | | 40000 |
| D-Mannitol | 52000 | 250 | 60000 | 52000 | 60000 |
| $FeSO_4 \cdot 7H_2O$ | 15 | 27.8 | 15 | 15 | 15 |
| $H_3BO_3$ | 5 | 3 | 1 | 5 | 1 |
| KCl | | 300 | | | |
| $KH_2PO_4$ | | 170 | 170 | | 170 |
| KI | 1 | 0.75 | 0.01 | 1 | 0.01 |
| $KNO_3$ | 2500 | 1900 | 505 | 2500 | 505 |
| MES pH 5.8 (mM) | | | 3.586 | 25 | 25 |
| $MgSO_4 \cdot 7H_2O$ | 400 | 300 | 370 | 400 | 370 |
| $MnSO_4 \cdot H_2O$ | 10 | 10 | 0.1 | 10 | 0.1 |
| $Na_2EDTA$ | 20 | 37.3 | 20 | 20 | 20 |
| $Na_2MoO_4 \cdot 2H_2O$ | 0.1 | 0.25 | | 0.1 | |
| $NH_4H_2PO_4$ | 300 | | | 300 | |
| $NH_4NO_3$ | | 600 | 160 | | 160 |
| $NiCl_2 \cdot 6H_2O$ | | | 0.03 | | |
| Sucrose | 30000 | 2500 | | 30000 | |
| $ZnSO_4 \cdot 7H_2O$ | 1 | 2 | 1 | 1 | 1 |
| Tween-80 (microliter/L) | | | 10 | | 10 |
| Inositol | 1000 | 100 | 100 | 1000 | 100 |
| Nicotinamide | | 1 | | | |
| Nicotinic acid | 5 | | 1 | 5 | 1 |
| Pyridoxine•HCl | 0.5 | 1 | 1 | 0.5 | 1 |
| Thiamine•HCl | 5 | 1 | 1 | 5 | 1 |

*Sources for basal media:
SH—Schenk and Hildebrandt, *Can. J. Bot.* 50: 199 (1971).
8p—Kao and Michayluk, *Planta* 126: 105 (1975).
P2—SH but with hormones from Potrykus et al., *Mol. Gen. Genet.* 156: 347 (1977).
PIM—Chupeau et al., *The Plant Cell* 25: 2444 (2013).

Example 3

This example illustrates culture conditions effective in improving viability of plant cells or plant protoplasts. More specifically, this non-limiting example describes methods for encapsulating isolated plant protoplasts.

When protoplasts are encapsulated in alginate or pectin, they remain intact far longer than they would in an equivalent liquid medium. In order to encapsulate protoplasts, a liquid medium ("calcium base") is prepared that is in all other respects identical to the final desired recipe with the exception that the calcium (usually $CaCl_2 \cdot 2H_2O$) is increased to 80 millimolar. A second medium ("encapsulation base") is prepared that has no added calcium but contains 10 g/L of the encapsulation agent, e. g., by making a 20 g/L solution of the encapsulation agent and adjusting its pH with KOH or NaOH until it is about 5.8, making a 2× solution of the final medium (with no calcium), then combining these two solutions in a 1:1 ratio. Encapsulation agents include alginate (e. g., alginic acid from brown algae, catalogue number A0682, Sigma-Aldrich, St. Louis, Mo.) and pectin (e. g., pectin from citrus peel, catalogue number P9136, Sigma-Aldrich, St. Louis, Mo.; various pectins including non-amidated low-methoxyl pectin, catalogue number 1120-50 from Modernist Pantry, Portsmouth, N.H.). The solutions, including the encapsulation base solution, is filter-sterilized through a series of filters, with the final filter being a 0.2-micrometer filter. Protoplasts are pelleted by gentle centrifugation and resuspended in the encapsulation base; the resulting suspension is added dropwise to the calcium base, upon which the protoplasts are immediately encapsulated in solid beads.

Example 4

This example illustrates culture conditions effective in improving viability of plant cells or plant protoplasts. More specifically, this non-limiting example describes observations of effects on protoplast viability obtained by adding non-conventionally high levels of divalent cations to culture media.

Typical plant cell or plant protoplast media contain between or about 2 to about 4 millimolar calcium cations and between or about 1-1.5 millimolar magnesium cations. In the course of experiments varying and adding components to media, it was discovered that the addition of non-conventionally high levels of divalent cations had a surprisingly beneficial effect on plant cell or plant protoplast viability. Beneficial effects on plant protoplast viability begin to be seen when the culture medium contains about 30 millimolar calcium cations (e. g., as calcium chloride) or about 30 millimolar magnesium cations (e. g., as magnesium chloride). Even higher levels of plant protoplast viability were observed with increasing concentrations of calcium or magnesium cations, i. e., at about 40 millimolar or about 50 millimolar calcium or magnesium cations. The result of several titration experiments indicated that greatest improvement in protoplast viability was seen using media containing between or about 50 to about 100 millimolar calcium cations or 50 to about 100 millimolar magnesium cations; no negative effects on protoplast viability or physical appearance was observed at these high cation levels. This was observed in multiple experiments using protoplasts obtained from several plant species including maize (multiple germplasms, e. g., B73, A188, B104, HiIIA, HiIIB, BMS), rice, wheat, soy, kale, and strawberry; improved protoplast viability was observed in both encapsulated protoplasts and non-encapsulated protoplasts. Addition of potassium chloride at the same levels had no effect on protoplast viability. It is possible that inclusion of slightly lower (but still non-conventionally high) levels of divalent cations (e. g., about 10 millimolar, about 15 millimolar, about 20 millimolar, or about 25 millimolar calcium cations or magnesium cations) in media is beneficial for plant cells or plant protoplasts of additional plant species.

Example 5

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize B73 and A188 protoplasts ($2 \times 10^5$ cells per milliliter) were prepared in YPIM B-liquid medium containing various combinations of the added salts calcium chloride, potassium ascorbate, and magnesium chloride or magnesium sulfate. One-half milliliter aliquots of the suspensions were dispensed into a 24-well microtiter plate in the arrangement shown in Table 2, which lists the concentrations of calcium chloride ("Ca"), potassium ascorbate ("A"), and magnesium chloride ("MgCl2") or magnesium sulfate ("MgSO4") in millimolar values.

TABLE 2

| YPIM B- | Ca = 0, A = 0.1 | Ca = 0, A = 0.2 | Ca = 0, A = 0.5 | Ca = 0, A = 1 | YPIM B- |
|---|---|---|---|---|---|
| Ca = 50, A = 0 | Ca = 50, A = 0.1 | Ca = 50, A = 0.2 | Ca = 50, A = 0.5 | Ca = 50, A = 1 | YPIM B- |
| Ca = 100, A = 0 | Ca = 100, A = 0.1 | Ca = 100, A = 0.2 | Ca = 100, A = 0.5 | Ca = 100, A = 1 | YPIM B- |
| YPIM B- | $MgCl_2$ = 50 | $MgCl_2$ = 100 | $MgSO_4$ = 50 | $MgSO_4$ = 100 | YPIM B- |

Viability was judged by Evans blue staining and visualization under a light microscope. After 96 hours, both maize species were still highly viable in all wells. After 288 hours, there were clear differences at various calcium and magnesium concentrations, but only slight effects at various ascorbate concentrations.

The observations at 288 hours were recorded as follows: Maize B73: protoplasts in all Ca=0 wells appeared small and dead; protoplasts in Ca=50 wells appeared larger but were now also almost all dead; protoplasts in Ca=100 wells still appeared larger and had a viability of between or 10-20%. Protoplasts in MgCl2=50 wells were similar to those in Ca=100 wells, and protoplasts in MgCl2=100 wells had much higher viability than any well. Wells with MgSO4=50 or 100 showed only a modest improvement in protoplast viability. Maize A188: protoplasts in all Ca=0 wells appeared small and dead; protoplasts in Ca=50 wells appeared and had about 20% viability; protoplasts in Ca=100 wells had about 70% viability and were visibly healthier. Addition of ascorbate at 0.2 millimolar and above to the wells with added calcium appeared to slightly decrease viability. Wells with MgSO4=50 had about 30-40% viability, and wells with MgCl2=100 had about 70% viability. Wells with MgSO4=50 or 100 showed only a modest improvement in protoplast viability. These results demonstrate that calcium chloride or magnesium chloride added at non-conventionally high levels improved maize protoplast viability over a culture time of ~12 days.

Example 6

This example illustrates culture conditions effective in improving viability of plant cells or plant protoplasts. More specifically, this non-limiting example describes observations of effects on maize, soybean, and strawberry protoplast viability obtained by adding non-conventionally high levels of divalent cations to culture media.

Separate suspensions of maize B73, winter wheat, soy, and strawberry protoplasts (2×10^5 cells per milliliter) were prepared in YPIM B-liquid medium containing calcium chloride at 0, 50, or 100 millimolar. One-half milliliter aliquots of the suspensions were dispensed into a 24-well microtiter plate.

Viability at day 8 of culture was judged by visualization under a light microscope. At this point, the viability of the maize protoplasts in the 0, 50, and 100 millimolar calcium conditions was 10%, 30%, and 80%, respectively. There were no large differences observed at this time point for protoplasts of the other species.

Viability at day 13 was judged by Evans blue staining and visualization under a light microscope. At this point, the viability of the maize protoplasts in the 0, 50, and 100 millimolar calcium conditions was 0%, 0%, and 10%, respectively; viability of the soybean protoplasts in the 0, 50, and 100 millimolar calcium conditions was 0%, 50%, and 50%, respectively; and viability of the maize protoplasts in the 0 and 50 millimolar calcium conditions was 0% and 50%, respectively (viability was not measured for the 100 millimolar condition). These results demonstrate that culture conditions including calcium cations at 50 or 100 millimolar improved viability of both monocot and dicot protoplasts over a culture time of ~13 days.

Example 7

This example illustrates culture conditions effective in improving viability of plant cells or plant protoplasts. More specifically, this non-limiting example describes observations of effects on maize protoplast viability obtained by adding non-conventionally high levels of divalent cations to culture media. Separate suspensions of maize A188 protoplasts (2×10^5 cells per milliliter) were prepared in YPIM B-liquid medium containing calcium chloride at 0 or 50 millimolar. One-half milliliter aliquots of the suspensions were dispensed into a 24-well microtiter plate.

Viability was judged by visualization under a light microscope. At 96 hours, protoplasts grown with 50 millimolar calcium cations appeared healthier than those grown with no added calcium. At 168 hours (7 days), wells with 50 millimolar calcium cations still contained very many large, healthy-looking protoplasts, whereas protoplasts in the wells with no added calcium were nearly all dead. This experiment was carried on to day 20, at which point the protoplasts in the wells with 50 millimolar calcium had generated cell walls and undergone at least some cell division. These results demonstrate that culture conditions including calcium cations at 50 millimolar improved viability, cell wall regeneration, and cell division of maize protoplasts over a culture time of at least 7 to 20 days.

Example 8

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize B73 protoplasts (2×10^5 cells per milliliter) were prepared in PIM B-liquid medium (identical to YPIM B-medium except with the 6-benzylaminopurine substituted with 0.022 milligrams/L thidiazuron) containing calcium chloride added at 0, 5, 20, 40, 70, or 100 millimolar. One-half milliliter aliquots of the suspensions were dispensed into a 24-well microtiter plate.

Viability was judged by visualization under a light microscope at day 7 and at day 14 of culture. In this experiment, by day 7 the maize protoplasts were dead in the wells containing less than 40 millimolar calcium; the maize protoplasts in the wells containing 40, 70, or 100 millimolar calcium formed clusters of viable, healthy cells with cell division occurring, with the strongest enhanced viability and cell division observed at 100 millimolar calcium. These results demonstrate that culture conditions including calcium cations at 40, 70, or 100 improved viability, cell wall regeneration, and cell division of maize protoplasts over a culture time of at least 7 to 14 days.

Example 9

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize B73 and A188 protoplasts (2×10^5 cells per milliliter) were prepared in PIM B-liquid medium (identical to YPIM B-medium except with the 6-benzylaminopurine substituted with 0.022 milligrams/L thidiazuron) containing calcium chloride added at 0 or 50 millimolar. One-half milliliter aliquots of the suspensions were dispensed into a 24-well microtiter plate.

Viability was judged by visualization under a light microscope. In this experiment, by day 6 the maize A188 protoplasts were about 40% viable in the wells containing no added calcium but showed much higher viability in the wells containing 50 millimolar calcium, where several wells showed 100% viability. The maize B73 protoplasts in the wells containing no added calcium had all died, but wells containing 50 millimolar calcium still contained viable cells.

Example 10

This example illustrates culture conditions effective in improving viability of plant cells or plant protoplasts. More specifically, this non-limiting example describes observations of effects on maize protoplast viability obtained by adding non-conventionally high levels of divalent cations or a low-molecular-weight antioxidant to culture media.

Separate suspensions of maize B73 and A188 protoplasts (2×10^5 cells per milliliter) were prepared in YPIM B-liquid medium containing (a) calcium chloride added at 100 millimolar, or (b) 1 millimolar glutathione, or (c) no added calcium or glutathione. One-milliliter aliquots of the suspensions were dispensed into a 24-well microtiter plate. At 16, 40, 64, and 136 hours of culture, 50-microliter samples were taken for hemocytometer analysis from each well; for the plates containing maize A188 protoplasts, parallel 50-microliter samples were taken from a replicate well at 16, 40, and 64 hours of culture for quantification using a Cellometer cell counter (Nexcelom Bioscience LLC, Lawrence, Mass.).

Viability was determined by Evans blue staining and quantification using a hemocytometer. Under conditions with high concentrations of calcium, Evans blue can create precipitates that interfere with cell counting; to prevent this, 5 microliters of an EDTA solution was added to the samples from the wells containing 100 millimolar calcium chloride immediately prior to staining. Results from the hemocytometer analysis are provided in Table 3 (results from the Cellometer analysis were very similar); "Control"=YPIM B-medium with no added calcium or glutathione. These results demonstrate that inclusion in the medium of either non-conventionally high (100 millimolar) calcium cations or the low-molecular-weight thiol antioxidant glutathione resulted in increasing protoplast viability of both maize lines by (a) at least 10% higher after 30 hours (in this example, about 10-34% higher at 40 hours) culture; (b) at least 10% higher after 48 hours' culture hours (in this example, between 17-53% higher at 64 hours); or (c) at least 10% higher after 72 hours' culture hours or at least 10% higher after 96 hours' culture hours (in this example, about 12—at least 46% higher at 138 hours).

TABLE 3

| Cell Type | Hours | Viability (%) | | |
|---|---|---|---|---|
| | | Control | 100 mM Ca | 1 mM GSH |
| B73 | 0 | 90 | 90 | 90 |
| | 16 | 65 | 65 | 77 |
| | 40 | 38 | 57 | 72 |
| | 64 | 31 | 58 | 48 |
| | 136 | 12 | 30 | 24 |
| A188 | 0 | 90 | 90 | 90 |
| | 16 | 60 | 67 | 69 |
| | 40 | 40 | 57 | 50 |
| | 64 | 6 | 59 | 50 |
| | 136 | 0 | 46 | 42 |

Example 11

This example illustrates culture conditions effective in improving viability of plant cells or plant protoplasts. More specifically, this non-limiting example describes the effects on maize protoplast viability obtained by adding non-conventionally high levels of divalent cations to culture media.

Separate suspensions of maize protoplasts from five different germplasm lines (A188, B73, B104, HiIIA, HiIIB) (2×10^5 cells per milliliter) were prepared in YPIM B-liquid medium containing calcium chloride added at 0, 50, or 100 millimolar. One-half milliliter aliquots of the suspensions were dispensed into a 24-well microtiter plate.

Viability was judged by visualization under a light microscope. At 19 hours, protoplasts of all five maize lines grown under the different conditions appeared healthy, with large proportions of round, green cells; slightly more debris was observed in the 0 calcium conditions. At 34 hours, protoplasts of all five maize lines showed a response to the increased calcium conditions similar to what had been previously observed; across the five maize lines, viability of protoplasts grown without added calcium was about 40%, while those grown with 50 millimolar calcium was about 55%, and those grown with 100 millimolar calcium was about 70%. These results demonstrate that culture conditions including calcium cations at 50 or 100 millimolar improved viability of protoplasts from various maize germplasm over a culture time of 34 hours.

Example 12

This example illustrates culture conditions effective in improving viability and cell division rates of plant cells or plant protoplasts. More specifically, this non-limiting example describes the effects on maize protoplast cultures of unconventionally hypoxic conditions. Thus, another aspect of the disclosure provides a method of improving the cell division rate of a plant protoplast culture, wherein the culture conditions include hypoxic conditions, for example, about one-half normal atmospheric oxygen concentrations; in certain embodiments of the method, the culture conditions further include at least 40 millimolar $Ca^{2+}$ or $Mg^{2+}$ in the medium. In certain embodiments, the cell division rate of the plant cells or plant protoplasts is improved by at least 20%, or by at least 50%, or by at least 75%, or by at least 100%. In an embodiment, the culture conditions include at least 40 millimolar Ca' and about one-half normal atmospheric oxygen concentrations, and the cell division rate of the plant cells or plant protoplasts is improved by at least 100% (i. e., cell division rate is about twice that observed in similar cultures grown under or subjected to normal atmospheric oxygen concentrations).

Normal atmospheric oxygen conditions are about 20.95% oxygen by volume; embodiments of the method thus include maintaining a plant cell or plant protoplast culture at less than about 20% oxygen by volume, for example, at less than about 4%, less than about 6%, less than about 8%, less than about 10%, less than about 12%, less than about 14%, less than about 16%, or less than about 18% oxygen by volume. In certain embodiments, the method involves maintaining a plant cell or plant protoplast culture between or about 5 to about 10% oxygen by volume, or even below about 5% oxygen by volume (e. g., at about 2%, about 3%, or about 4% oxygen by volume).

Plant cell or protoplast cultures are conveniently maintained under hypoxia (oxygen concentration less than normal atmospheric oxygen concentration) with incubation systems that use nitrogen gas pressure to increase the percentage of nitrogen in the atmosphere with concomitant decrease of the percentage of oxygen in the atmosphere. An oxygen sensor is used to control and rapidly re-equilibrate oxygen levels as needed. Commercial bioreactor or incubation systems (e. g., the "Avatar" bioreactor/incubator, XCell Biosciences, San Francisco, Calif.) can be employed.

Initial experiments indicated that decreasing atmospheric oxygen concentrations were beneficial to the plant cells or protoplasts. Similar effects of hypoxia were observed for cell cultures from several maize lines (HiIIA, B104, B73, A188, and BMS), as well as from kale. Cells incubated under normal ambient (about 21% by volume) oxygen concentrations showed a brown-coloured phenotype (caused by production of phenolic compounds, an indicator of cellular stress) faster than those incubated under 5% oxygen by volume. Cell division was monitored, e. g., by microscopic observations. For example, a greater number of living cells, resulting from cell division, were observed in cultures incubated under 5% or 10% oxygen by volume, when compared to cultures grown under or subjected to normal atmospheric (about 21%) oxygen. Two experiments demonstrated that approximately twice as many living cells resulting from cell division in cultures incubated under 5% oxygen by volume, when compared to cultures grown under or subjected to about 21% oxygen by volume. Evidence of cell division was observed by microscopy and included increased cell or protoplast size, bulging membranes, and large groups of organelles occupying the separating daughter cells. Quantification of cell division was carried out using fluorescent staining. Cells were treated with the thymidine analogue 5-ethynyl-2'-deoxyuridine (EdU), which is incorporated into DNA during S-phase and can be fluorescently activated using a fluorochrome that has been conjugated to an azide molecule. Cells that are the result of cellular division in the presence of EdU were identified by the resulting green fluorescent signal, which can be quantified by various means, e. g., with a microplate reader, cell counter, or cell sorter.

In one experiment, maize A188 protoplasts were grown under either 5% or 21% oxygen by volume in YPIM B-liquid medium containing 100 millimolar $Ca^{2+}$. On day 8 of culture, the culture grown under 5% oxygen by volume were observed to have many more protoplasts displaying signs of cell division ("budding" and bulging of membranes, with organelles distributed among both forming daughter cells), in comparison to the culture grown under 21% oxygen by volume.

In a separate experiment, maize HiIIA protoplasts were grown in 24-well plates using YPIM B-liquid medium containing 100 millimolar $Ca^{2+}$ and 20 micromolar EdU. Identical plates were incubated under hypoxia (5% oxygen by volume, 26 degrees Celsius, 80% relative humidity) or ambient oxygen (21% oxygen by volume, 26 degrees Celsius, 80% relative humidity). Entire wells (250 microliters) were taken for EdU detection at four time points. The contents of each well was centrifuged and the pellet subjected to the Click-iT™ EdU Alexa Fluor™ 488 Imaging Kit (catalogue number C10337, Thermo Fisher Scientific, Waltham, Mass.) fluorescent labelling protocol. The labelled protoplasts were resuspended in YPIM B-medium and samples analyzed on a Nexcelom Cellometer (Nexcelom Bioscience LLC, Lawrence, Mass.). This assay was developed to detect the EdU signal from the nucleus of a cell resulting from cell division, as well as the fluorescent signal from chloroplasts as a measure of total cell count. Results are provided in Table 4 as a percentage of cells displaying the EdU signal relative to the total cell count ("% EdU"). The data indicate that the rate of cell division (expressed as % EdU) was increased by between about 2- to about 4-fold (about 100 to about 400 percent increase) in the cultures grown under hypoxic conditions (5% oxygen by volume), compared to the rate of cell division in cultures grown under normal atmospheric oxygen (21% by volume).

TABLE 4

| % oxygen by volume | culture time (hours) | % EdU |
|---|---|---|
| 5 | 93 | 12 |
|  | 93 | —* |
|  | 117 | 19 |
|  | 117 | 19 |
|  | 141 | 11 |
|  | 141 | 33 |
|  | 165 | 19 |
|  | 165 | 15 |

TABLE 4-continued

| % oxygen by volume | culture time (hours) | % EdU |
|---|---|---|
| 21 | 93 | 6.5 |
|  | 93 | —* |
|  | 117 | 6.9 |
|  | 117 | 8.0 |
|  | 141 | 13 |
|  | 141 | 4.8 |
|  | 165 | 5.0 |
|  | 165 | 0.0 |

*only single samples taken

Another experiment was carried out using protocols similar to those used in the immediately preceding experiment but using maize B104 protoplasts grown 24-well plates using YPIM B-liquid medium containing 100 millimolar $Ca^{2+}$ and 20 micromolar EdU, with or without 0.5 millimolar glutathione added to the medium. Entire wells (1000 microliters) were taken for EdU detection at three time points; analyses were of duplicate samples of each of two replicate wells. Results are provided in Table 5 as a percentage of cells displaying the EdU signal relative to the total cell count ("% EdU"). The data indicate that, in the cultures grown with 100 millimolar $Ca^{2+}$ but no added glutathione, the rate of cell division (expressed as % EdU) was increased by about 2- to 2.5-fold (about 100 to about 250 percent increase) under hypoxic conditions (5% oxygen by volume), compared to the rate of cell division in cultures grown under normal atmospheric oxygen (21% by volume). In the cultures grown under hypoxic conditions, the addition of 0.5 millimolar glutathione resulted in little change in the rate of cell division (expressed as % EdU), but in the cultures grown under normal atmospheric oxygen, the addition of 0.5 millimolar glutathione resulted in an increase in the rate of cell division (expressed as % EdU) of about 2-fold (about 100% increase), indicating that, under normal atmospheric conditions where greater oxidative stress is possible, the beneficial antioxidant effects of glutathione are significant.

TABLE 5

| | | | | EdU staining | |
|---|---|---|---|---|---|
| $O_2$ (% volume) | $Ca^{2+}$ (mM) | Glutathione (mM) | culture time (h) | mean % | standard deviation |
| 5 | 100 | 0 | 90 | 21.9 | 5.2 |
|  |  |  | 138 | 27.8 | 1.0 |
|  |  |  | 186 | 19.7 | 2.3 |
| 21 | 100 | 0 | 90 | 8.0 | 1.3 |
|  |  |  | 138 | 12.9 | 1.0 |
|  |  |  | 186 | 8.2 | 1.2 |
| 5 | 100 | 0.5 | 90 | 18.4 | 0.7 |
|  |  |  | 138 | 28.0 | 4.7 |
|  |  |  | 186 | 21.1 | 0.8 |
| 21 | 100 | 0.5 | 90 | 16.9 | 4.9 |
|  |  |  | 138 | 21.9 | 4.9 |
|  |  |  | 186 | 18.3* | —* |

*mean of duplicate samples from single well

Example 13

This example illustrates methods and compositions effective in improving the efficacy of homology-directed repair (HDR) genome editing in plant cells or plant protoplasts. More specifically, this non-limiting example describes improving the efficacy of homology-directed repair (HDR) genome editing in plant protoplasts by subjecting the protoplasts to unconventionally hypoxic conditions or by treating with a reactive oxygen species (ROS) concentration-lowering agent. Thus, an aspect of the invention provides a method of improving the efficacy of HDR genome editing in plant cells or plant protoplasts, by providing genome editing molecules to a plant cell previously, concurrently, or subsequently exposed to a hypoxic condition, or to a ROS concentration-lowering agent, or to a combination thereof; in embodiments, the culture conditions further include at least 40 millimolar $Ca^{2+}$ or $Mg^{2+}$ in the medium. Another aspect of the invention provides compositions comprising at least one HDR genome editing agent (such as a sequence-specific nuclease, guide RNA, or donor template polynucleotide) and a plant cell or protoplast in which the ROS concentration is decreased (for example, by subjecting the protoplasts to unconventionally hypoxic conditions or by treating with a ROS concentration-lowering agent), relative to a control plant cell or protoplast; in embodiments, the composition further includes a culture medium containing at least 40 millimolar $Ca^{2+}$ or $Mg^{2+}$.

In this example, hypoxia is demonstrated to increase the efficiency of HDR editing in a non-endogenous reporter gene. A "traffic light" reporter was designed to contain a blue fluorescent protein (BFP) and a red fluorescent protein "mCherry" in the construct encoding the polyprotein BFP-LP4/2A-mCherry-NLS. LP4/2A is a hybrid linker peptide that contains the first nine amino acids of LP4 and 20 amino acids of 2A (see doi[dot]org/10[dot]1371/journal[dot]pone[dot]0174804), and has high cleavage splicing efficiency within the polyprotein construct. To create the "traffic light" reporter, two nucleotides are added in front of LP4/2A to make the translation of mCherry out of frame. The DNA sequence encoding the polyprotein BFP-LP4/2A-mCherry-NLS is provided as:

```
                                        (SEQ ID NO: 10)
ATGGTCAGCAAGGGAGAGGAGCTTTTCACGGGGGTGGTCCCCATCCTCG

TGGAATTGGACGGCGATGTTAATGGGCACAAATTTTCCGTTTCTGGAGA

GGGTGAGGGCGATGCGACATATGGGAAGTTGACCCTTAAATTTATCTGC

ACGACTGGCAAGCTCCCTGTCCCCTGGCCTACACTTGTCACGACGTTGA

CTCACGGAGTCCAGTGCTTTTCGAGGTATCCTGATCATATGAAACAGCA

CGATTTTTTCAAGTCAGCTATGCCCGAGGGGTATGTTCAGGAAAGAACT

ATCTTCTTTAAAGATGATGGCAATTACAAGACGAGAGCGGAGGTGAAGT

TTGAGGGGGATACACTTGTTAATAGAATCGAACTGAAGGGAATCGACTT

TAAGGAGGACGGAAACATACTGGGTCACAAACTTGAGTATAACTACAAC

TCTCACAATGTCTACATAATGGCGGACAAGCAGAAGAACGGTATTAAAG

TCAACTTCAAAATCCGCCACAACATTGAGGACGGATCCGTCCAATTGGC

CGATCATTACCAGCAAAATACTCCGATAGGTGACGGGCCCGTTTTGCTG

CCCGATAATCACTATTTGTCCACCCAGTCCAAGCTCTCTAAGGATCCGA

ATGAGAAGAGAGACCATATGGTCCTCCTTGAGTTTGTTACCGCTGCGGG

TATAACGCTTGGCATGGATGAACTTTACAAGTGtccaacgcggcggacg aggtggctacccagctgttgaattttgaccttcttaagcttgcgggaga cgtcgagtccaaccctgggcctATGGTCAGCAAGGGCGAGGAGGACAAT ATGGCTATCATCAAGGAGTTCATGAGGTTTAAGGTTCACATGGAAGGCT
```
-continued
```
CAGTCAACGGGCACGAGTTCGAGATCGAGGGCGAGGGCGAGGGCAGGCC

TTACGAGGGCACCCAGACCGCTAAGCTGAAGGTGACGAAGGGCGGCCCC

CTCCCTTTCGCCTGGGACATCCTGTCCCCGCAGTTCATGTACGGCAGCA

AGGCCTACGTCAAGCACCCGGCGGACATCCCGGACTACCTCAAGCTGTC

CTTCCCGGAGGGCTTCAAGTGGGAGCGCGTGATGAACTTCGAGGACGGC

GGCGTGGTCACGGTCACCCAGGACTCCAGCCTCCAGGACGGCGAGTTCA

TCTACAAGGTGAAGCTGCGGGGCACCAACTTCCCTTCGGACGGCCCGGT

CATGCAGAAGAAGACGATGGGCTGGGAGGCTTCCTCGGAGAGGATGTAC

CCTGAGGACGGAGCCCTGAAGGGCGAGATCAAGCAGAGGCTCAAGCTGA

AGGACGGCGGCCACTACGACGCCGAGGTGAAGACGACGTACAAGGCGAA

GAAGCCTGTGCAGCTCCCGGGCGCATACAACGTCAACATCAAGCTGGAC

ATCACGTCCCACAACGAGGACTACACGATCGTGGAGCAGTACGAGCGGG

CGGAGGGGCGGCATAGCACGGGCGGGATGGACGAGCTGTACAAG cctaagaagaagaggaaggttTGA,
``` where the BFP sequence is in bold, uppercase with the gRNA targeting region is underlined; the LP4/2A sequence is in lowercase, the mCherry sequence is in italicized uppercase; and the nuclear localization signal (NLS) is double underlined and in lowercase. An HDER donor template with the DNA sequence AAGTTGACCCTTAAATT-TATCTGCACGACTGGCAAGCTCCCTGTCCCCTGGCC-TACACTTGTCAC GACGTTGACTTACG-GAGTCCAGTGCTTTTCGAGGTATCCTGATCATAT-GAAACAGCACGATTTTT TCAAGTCAGCTATG (SEQ ID NO:11, Integrated DNA Technologies, Coralville, Iowa) was provided as a single-stranded DNA (ssDNA), phosphorylated on the 5' end and containing three phosphorothioate linkages at each terminus (i. e., the three linkages between the most distal four bases on either end of the strand). A guide crRNA with the sequence CUUGU-CACGACGUUGACUCAGUUUUAGAGCUAUGCU (SEQ ID NO:12, BFP guide crRNA; Integrated DNA Technologies, Coralville, Iowa) was designed to introduce a double-stranded break (DSB) within the "traffic light" reporter's BFP coding sequence. This DSB can be repaired through the NHEJ pathway with an indel that leads to in-frame expression of mCherry, resulting in red fluorescence. Alternatively, if the donor template is provided and integrated at the DSB by the HDR pathway, this results in a change of His67 to Tyr in the original BFP sequence, changing the BFP reporter to a green fluorescent protein (GFP).

To prepare a guide RNA duplex, 63 microliters of 100 micromolar the BFP guide crRNA (SEQ ID NO:12) was added to 63 microliters of 100 micromolar tracrRNA (Integrated DNA Technologies, Coralville, Iowa), heated to 95 degrees Celsius for 5 minutes, and then removed from the heating block and allowed to cool to room temperature. Before transfection, 18 microliters (180 milligrams) of Cas9 protein (Aldevron, Fargo, N. Dak.) was added to the gRNA complex and the mixture allowed to incubate for 5 minutes at room temperature to form the ribonucleoprotein (RNP) complex; 4.5 microliters (45 micrograms) of salmon sperm DNA was added to the RNP solution.

Transfections were carried out as follows. Maize B73 plant protoplast cells were prepared essentially as described in Example 1. The protoplasts were at a concentration of 2×10^5 protoplasts/milliliter. About 40×10^4 protoplasts in 2004 of MMg solution were used in each transfection experiment. To each tube was added 14 microliters of the RNP solution, 10 microliters of the reporter plasmid, with or without 10 microliters of the donor template, plus 244 microliters of 40% PEG and sufficient buffer if needed to equalize volumes; the tubes were tapped to mix and allowed to incubate for 5 minutes at room temperature. The reaction was stopped by addition of 976 microliters of maize washing buffer. The protoplast cells were centrifuged at 1200 rpm for 2 minutes, and the supernatant was removed. The pelleted cells were then resuspended in PIM medium containing 50 millimolar $CaCl_2$ and then plated in 6-well plates coated with 5% calf serum. The plates were sealed with Parafilm™ and allowed to incubate at 37 degrees Celsius for 1 hour. For the hypoxia treatment, the Parafilm™ was removed and the plates were then placed in a hypoxia chamber having about 5% oxygen by volume at 26 degrees Celsius in the dark. For normoxia treatment, the Parafilm™ was kept in place and the plates were incubated at 26 degrees Celsius in a growth chamber in the dark. Cells were harvested 48 hours after transfection for imaging on a fluorescent microscope, which allows quantification of HDR editing efficiency by measuring GFP fluorescence based either on individual cell fluorescence or on averaged fluorescence ("relative fluorescence units", RFU) measured across a well.

In a first experiment using these procedures, HDR editing frequency was quantitated by individual cell fluorescence. The HDR editing frequency under normoxic conditions was 1.97% of the cell population. HDR editing frequency was increased by hypoxia treatment to 3.91% of the cell population (about a 2-fold increase over normoxia). In a second experiment using these procedures, HDR editing frequency was quantitated by averaged fluorescence measured across a well and expressed as an RFU ratio normalized to the RNP-only (no donor template) control. No marked difference was observed between the NHEJ editing frequency under normoxic conditions (1.11) and under hypoxic conditions (1.02), but the HDR editing frequency observed under normoxic conditions (0.897) increased about 9-fold under hypoxic conditions (8.19). The data from these experiments indicate that exposure of the plant cells to hypoxia, which is expected to reduce reactive oxygen species (ROS) concentrations in the cells, increased efficacy of homology-directed repair (HDR) of a target gene in the plant cells.

Example 14

This example illustrates methods and compositions effective in improving the efficacy of homology-directed repair (HDR) genome editing in plant cells or plant protoplasts. More specifically, this non-limiting example describes improving the efficacy of homology-directed repair (HDR) genome editing in plant protoplasts by subjecting the protoplasts to unconventionally hypoxic conditions or by treating with a reactive oxygen species (ROS) concentration-lowering agent. Thus, an aspect of the invention provides a method of improving the efficacy of HDR genome editing in plant cells or plant protoplasts, by providing genome editing molecules to a plant cell previously, concurrently, or subsequently exposed to a hypoxic condition, or to a ROS concentration-lowering agent, or to a combination thereof; in embodiments, the culture conditions further include at least 40 millimolar $Ca^{2+}$ or $Mg^{2+}$ in the medium. Another aspect of the invention provides compositions comprising at least one HDR genome editing agent (such as a sequence-specific nuclease, guide RNA, or donor template polynucleotide) and a plant cell or protoplast in which the ROS concentration is decreased (for example, by subjecting the protoplasts to unconventionally hypoxic conditions or by treating with a ROS concentration-lowering agent), relative to a control plant cell or protoplast; in embodiments, the composition further includes a culture medium containing at least 40 millimolar $Ca^{2+}$ or $Mg^{2+}$.

In this example, hypoxia is demonstrated to increase the efficiency of HDR editing in an endogenous plant gene, the maize (*Zea mays*) alcohol dehydrogenase ADH1 gene with the partial genomic sequence provided as:

```
                                             (SEQ ID NO: 13)
GAACAGTGCCGCAGTGGCGCTGATCTTGTATGCTATCCTGCAATCGTGG

TGAACTTATTTCTTTTATATCCTTTACTCCCATGAAAAGGCTAGTAATC

TTTCTCGATGTAACATCGTCCAGCACTGCTATTACCGTGTGGTCCATCC

GACAGTCTGGCTGAACACATCATACGATCTATGGAGCAAAAATCTATCT

TCCCTGTTCTTTAATGAAGGACGTCATTTTCATTAGTATGATCTAGGAA

TGTTGCAACTTGCAAGGAGGCGTTTCTTTCTTTGAATTTAACTAACTCG

TTGAGTGGCCCTGTTTCTCGGACGTAAGGCCTTTGCTGCTCCACACATG

TCCATTCGAATTTTACCGTGTTTAGCAAGGGCGAAAAGTTTGCATCTTG

ATGATTTAGCTTGACTATGCGATTGCTTTCCTGGACCCGTCAGCTGCG

GTGGCATGGGAGGCCGGCAAGCCACTGTCGATCGAGGAGGTGGAGGTAG

CGCCTCCGCAGGCCATGGAGGTGCGCGTCAAGATCCTCTTCACCTCGCT

CTGCCACACCGACGTCTACTTCTGGGAGGCCAAGGTATCTAATCAGCCA

TCCCATTTGTGATCTTTGTCAGTAGATATGATCAACAACTCGCGGTTG

ACTTGCGCCTTCTTGGCGGCTTATCTGTCTTAGGGGCAGACTCCCGTGT

TCCCTCGGATCTTTGGCCACGAGGCTGGAGGGTA.
```

The first exon located at nucleotide positions 409-571 is indicated by bold, underlined text.

A ribonucleoprotein (RNP) was prepared with Cas9 nuclease (Aldevron, Fargo, N. Dak.) and a guide RNA complex designed to edit the first ADH1 exon, consisting of a crRNA (ZmADH1-B) with the sequence GGC-CUCCCAGAAGUAGACGUGUUUUAGAGCUAUGCU (SEQ ID NO:14) complexed with a tracrRNA (both purchased from Integrated DNA Technologies, Coralville, Iowa). A single-stranded DNA donor template designed for homology-directed repair of the ADH exon had the sequence AGGAGGTGGAGGTAGCGCCTCCGCAGGCCATG-GAGGTGCGCGTCAAGATCCTCTTCACCTCGCT CTGGTACCCCGACGTCTACTTCTGGGAGGC-CAAGGTATCTAATCAGCCATCCCATTTGTGATCTT TGTCAGTAGATATGA (SEQ ID NO:15, Integrated DNA Technologies, Coralville, Iowa); the donor ssDNA contained three phosphorothioate linkages at each terminus (i. e., the three linkages between the most distal four bases on either end of the strand), and contained a KpnI restriction enzyme digestion site at nucleotide positions 67-72 (shown as underlined text). A double-stranded DNA (purchased from Integrated DNA Technologies, Coralville, Iowa) was designed with a forward strand having the sequence GTTTAATT-GAGTTGTCATATGTTAATAACGGTAT (SEQ ID NO:16) and a reverse strand having the sequence ATACCGTTAT-TAACATATGACAACTCAATTAAAC (SEQ ID NO:17), wherein each strand was phosphorylated on the 5' end and contained two phosphorothioate linkages at each terminus (i.e., the two linkages between the most distal three bases on either end of the strand); this contained an NdeI restriction site located at nucleotide positions 16-21 of the forward strand (SEQ ID NO:16), shown as underlined font. Insertion of this sequence into the first exon of the target gene ADH1 serves as a proxy readout for efficiency of the NHEJ pathway (i.e., non-homologous repair of the expected DSB).

Transfection procedures were essentially as described in Example 13. In a first experiment, cells were treated with the HDR ssDNA donor containing a KpnI restriction site, or with no donor polynucleotide. After transfection with the editing reagents, the washed and pelleted cells were then resuspended in PIM containing 50 millimolar $CaCl_2$, and then plated in 6-well plates coated with 5% calf serum. The plates were sealed with Parafilm™ and allowed to incubate at 37 degrees Celsius for 1 hour. For the hypoxia treatment, the Parafilm™ was removed and the plates were then placed in a hypoxia chamber having about 5% oxygen by volume at 26 degrees Celsius in the dark. For normoxia treatment, the Parafilm™ was kept in place and the plates were incubated at 26 degrees Celsius in a growth chamber in the dark. Cells were harvested 48 hours and HDR editing efficacy was quantitated by PCR analysis using Phusion™ Flash PCR (Thermo Fisher Scientific, Waltham, Mass.). Under normoxic conditions, HDR editing efficacy was 0%. Under hypoxic conditions, HDR editing efficacy was increased to 1.35%. Thus, treatment with hypoxia, which is expected to reduce reactive oxygen species (ROS) concentrations in the cell, increased HDR editing efficiency in an endogenous plant gene.

In a second experiment, cells were treated with the HDR ssDNA donor containing a Kpn1 restriction site, or with the NHEJ dsDNA containing an NdeI restriction site, or with no donor polynucleotide. After transfection with the editing reagents, the washed and pelleted cells were then resuspended in PIM containing 50 millimolar $CaCl_2$, with or without 0.5 millimolar glutathione (GSH), and then plated in 6-well plates coated with 5% calf serum. The plates were sealed with Parafilm™ and allowed to incubate at 37 degrees Celsius for 1 hour. For the hypoxia treatment, the Parafilm™ was removed and the plates were then placed in a hypoxia chamber having about 5% oxygen by volume at 26 degrees Celsius in the dark. For normoxia treatment, the Parafilm™ was kept in place and the plates were incubated at 26 degrees Celsius in a growth chamber in the dark. Cells were harvested 48 hours and subjected to PCR analysis using Phusion™ Flash PCR (Thermo Fisher Scientific, Waltham, Mass.). Results are provided in Table 6. Under normoxic conditions, no HDR editing was detected in cells treated with the homologous HDR donor, in contrast to cells treated with the non-homologous NHEJ donor, where 24% NHEJ editing efficiency was observed. With treatment with glutathione, HDR efficiency was 5.0% and NHEJ efficiency was about 15%. Under hypoxia, HDR efficiency was 3.25% and NHEJ efficiency was about 14%. These data indicate that treatment with a low-molecular-weight thiol antioxidant or with hypoxia, treatments that are expected to reduce reactive oxygen species (ROS) concentrations in the cell, increased HDR editing efficiency in an endogenous plant gene.

TABLE 6

| Treatment | Editing Reagents | % KpnI (HDR) | % NdeI (NHEJ) |
|---|---|---|---|
| Normoxia | Null | 0.00 | 0.00 |
| Normoxia | RNP only | 0.00 | 0.00 |
| Normoxia | RNP plus HDR donor | 0.00 | — |
| Normoxia | RNP plus NHEJ donor | — | 24.00 |
| 0.5 mM GSH | Null | 0.00 | 0.00 |
| 0.5 mM GSH | RNP only | 0.00 | 0.00 |
| 0.5 mM GSH | RNP plus HDR donor | 5.00 | — |
| 0.5 mM GSH | RNP plus NHEJ donor | — | 15.01 |
| Hypoxia | Null | 0.00 | 0.00 |
| Hypoxia | RNP only | 0.00 | 0.00 |
| Hypoxia | RNP plus HDR donor | 3.25 | — |
| Hypoxia | RNP plus NHEJ donor | — | 14.35 |

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this disclosure have been described in terms of embodiments and illustrative examples, it will be apparent to those of skill in the art that substitutions and variations can be applied to the materials and methods described herein without departing from the concept, spirit, and scope of the disclosure. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the disclosure as encompassed by the embodiments recited herein and the specification and appended claims.

What is claimed is:

1. A method for making a maize plant protoplast having a genomic modification comprising:
   (a) providing genome editing molecules to a maize plant protoplast lacking a cell wall wherein the genome editing molecules are designed for homology-directed repair of a target gene in the plant cell's genome and comprise: (i) an RNA-guided nuclease and a guide RNA and a donor template polynucleotide; (ii) a sequence-specific endonuclease and a donor template polynucleotide; (iii) one or more polynucleotides encoding an RNA-guided nuclease and a guide RNA and a donor template polynucleotide; (iv) a polynucleotide encoding a sequence-specific endonuclease and a donor template polynucleotide; or (v) any combination thereof,
   (b) exposing the maize plant protoplast from step (a) to plant cell culture medium comprising a reactive oxygen species (ROS) concentration lowering agent at a concentration of 0.1 millimolar to 10 millimolar and Ca2+ and/or Mg2+ at a concentration of about 40 mM to 150 mM for at least one hour to effect homology-directed repair of the target gene in the plant cell's genome at a frequency that is increased by at least 2-fold in comparison to a control method wherein a control plant cell is provided with the genome editing molecules but is not subjected to a ROS concentration lowering agent at a concentration of 0.1 millimolar to 10 millimolar, wherein the ROS concentration lowering agent is a ROS scavenging agent or an antioxidant; and,
   (c) isolating, selecting, identifying, and/or propagating a maize plant protoplast comprising the genome modification, thereby making the maize plant protoplast having a genomic modification.

2. The method of claim 1, wherein the ROS concentration lowering agent is one or more low-molecular-weight thiol compound(s) wherein the molecular weight of the thiol compound is less than 1,000.

3. The method of claim 2, wherein the thiol compound(s) are glutathione, cysteine, cysteinyl glycine, gamma-glutamyl cysteine, N-acetylcysteine, cysteine, thiocysteine, homocysteine, lipoic acid, dithiothreitol, or a combination thereof.

4. The method of claim 2, wherein the thiol compound is gluthathione.

* * * * *

SEQUENCE LISTING

```
<160> NUMBER OF SEQ ID NOS: 17

<210> SEQ ID NO 1
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 1
``` nnagaa                                                                6

<210> SEQ ID NO 2
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 2 nggng                                                                 5

<210> SEQ ID NO 3
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: r is g or a
<220> FEATURE:
<221> NAME/KEY: misc_feature
<222> LOCATION: (5)..(5)
<223> OTHER INFORMATION: r is g or a

<400> SEQUENCE: 3 nngrrt                                                                6

<210> SEQ ID NO 4
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: r is g or a
<220> FEATURE:
<221> NAME/KEY: misc_feature
<222> LOCATION: (5)..(5)
<223> OTHER INFORMATION: r is g or a

<400> SEQUENCE: 4 nngrr                                                                 5

<210> SEQ ID NO 5
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (1)..(3)
<223> OTHER INFORMATION: n is a, c, g, or t

<400> SEQUENCE: 5 nnngatt                                                                         7

<210> SEQ ID NO 6
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 6 nnnnacac                                                                        8

<210> SEQ ID NO 7
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (5)..(5)
<223> OTHER INFORMATION: r is g or a
<220> FEATURE:
<221> NAME/KEY: misc_feature
<222> LOCATION: (6)..(6)
<223> OTHER INFORMATION: y is  t/u or c

<400> SEQUENCE: 7 nnnnry                                                                          6

<210> SEQ ID NO 8
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 8 nnnnaca                                                                         7

<210> SEQ ID NO 9
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (5)..(5)
<223> OTHER INFORMATION: r is g or a
<220> FEATURE:
```

```
<221> NAME/KEY: misc_feature
<222> LOCATION: (6)..(6)
<223> OTHER INFORMATION: y is t/u or c

<400> SEQUENCE: 9 nnnnryac                                                                    8

<210> SEQ ID NO 10
<211> LENGTH: 1538
<212> TYPE: DNA
<213> ORGANISM: Artificial Sequence
<220> FEATURE:
<223> OTHER INFORMATION: Synthetic

<400> SEQUENCE: 10
atggtcagca agggagagga gcttttcacg ggggtggtcc ccatcctcgt ggaattggac     60
ggcgatgtta atgggcacaa attttccgtt tctggagagg gtgagggcga tgcgacatat    120
gggaagttga cccttaaatt tatctgcacg actggcaagc tccctgtccc ctggcctaca    180
cttgtcacga cgttgactca cggagtccag tgcttttcga ggtatcctga tcatatgaaa    240
cagcacgatt ttttcaagtc agctatgccc gaggggtatg ttcaggaaag aactatcttc    300
tttaaagatg atggcaatta caagacgaga gcggaggtga agtttgaggg ggatacactt    360
gttaatagaa tcgaactgaa gggaatcgac tttaaggagg acggaaacat actgggtcac    420
aaacttgagt ataactacaa ctctcacaat gtctacataa tggcggacaa gcagaagaac    480
ggtattaaag tcaacttcaa aatccgccac aacattgagg acggatccgt ccaattggcc    540
gatcattacc agcaaaatac tccgataggt gacgggcccg ttttgctgcc cgataatcac    600
tatttgtcca cccagtccaa gctctctaag gatccgaatg agaagagaga ccatatggtc    660
ctccttgagt ttgttaccgc tgcgggtata acgcttggca tggatgaact ttacaagtgt    720
ccaacgcggc ggacgaggtg gctacccagc tgttgaattt tgaccttctt aagcttgcgg    780
gagacgtcga gtccaacccct gggcctatgg tcagcaaggg cgaggaggac aatatggcta    840
tcatcaagga gttcatgagg tttaaggttc acatggaagg ctcagtcaac gggcacgagt    900
tcgagatcga gggcgagggc gagggcaggc cttacgaggg cacccagacc gctaagctga    960
aggtgacgaa gggcggcccc ctccctttcg cctgggacat cctgtccccg cagttcatgt   1020
acggcagcaa ggcctacgtc aagcacccgg cggacatccc ggactacctc aagctgtcct   1080
tcccggaggg cttcaagtgg gagcgcgtga tgaacttcga ggacggcggc gtggtcacgg   1140
tcacccagga ctccagcctc caggacgcg agttcatcta caaggtgaag ctgcggggca   1200
ccaacttccc ttcggacggc ccggtcatgc agaagaagac gatgggctgg gaggcttcct   1260
cggagaggat gtaccctgag gacgagccc tgaaggcga gatcaagcag aggctcaagc   1320
tgaaggacgg cggccactac gacgccgagg tgaagacgac gtacaaggcg aagaagcctg   1380
tgcagctccc gggcgcatac aacgtcaaca tcaagctgga catcacgtcc cacaacgagg   1440
actacacgat cgtggagcag tacgagcggg cggaggggcg gcatagcacg ggcgggatgg   1500
acgagctgta caagcctaag aagaagagga aggtttga                            1538

<210> SEQ ID NO 11
<211> LENGTH: 144
<212> TYPE: DNA
<213> ORGANISM: Artificial Sequence
<220> FEATURE:
<223> OTHER INFORMATION: Synthetic
<220> FEATURE:
<221> NAME/KEY: modified_base
```

```
<222> LOCATION: (1)..(1)
<223> OTHER INFORMATION: phosphorothioate bond to residue 2
<220> FEATURE:
<221> NAME/KEY: modified_base
<222> LOCATION: (1)..(1)
<223> OTHER INFORMATION: phosphorylated 5' end
<220> FEATURE:
<221> NAME/KEY: modified_base
<222> LOCATION: (2)..(2)
<223> OTHER INFORMATION: phosphorothioate bond to residue 3
<220> FEATURE:
<221> NAME/KEY: modified_base
<222> LOCATION: (3)..(3)
<223> OTHER INFORMATION: phosphorothioate bond to residue 4
<220> FEATURE:
<221> NAME/KEY: modified_base
<222> LOCATION: (141)..(141)
<223> OTHER INFORMATION: phosphorothioate bond to residue 142
<220> FEATURE:
<221> NAME/KEY: modified_base
<222> LOCATION: (142)..(142)
<223> OTHER INFORMATION: phosphorothioate bond to residue 143
<220> FEATURE:
<221> NAME/KEY: modified_base
<222> LOCATION: (143)..(143)
<223> OTHER INFORMATION: phosphorothioate bond to residue 144

<400> SEQUENCE: 11
aagttgaccc ttaaatttat ctgcacgact ggcaagctcc ctgtcccctg gcctacactt      60
gtcacgacgt tgacttacgg agtccagtgc ttttcgaggt atcctgatca tatgaaacag     120
cacgattttt tcaagtcagc tatg                                            144

<210> SEQ ID NO 12
<211> LENGTH: 36
<212> TYPE: RNA
<213> ORGANISM: Artificial Sequence
<220> FEATURE:
<223> OTHER INFORMATION: Synthetic

<400> SEQUENCE: 12
cuugucacga cguugacuca guuuuagagc uaugcu                               36

<210> SEQ ID NO 13
<211> LENGTH: 720
<212> TYPE: DNA
<213> ORGANISM: Zea mays

<400> SEQUENCE: 13
gaacagtgcc gcagtggcgc tgatcttgta tgctatcctg caatcgtggt gaacttattt      60
cttttatatc ctttactccc atgaaaaggc tagtaatctt tctcgatgta acatcgtcca     120
gcactgctat taccgtgtgg tccatccgac agtctggctg aacacatcat acgatctatg     180
gagcaaaaat ctatcttccc tgttctttaa tgaaggacgt catttttcatt agtatgatct    240 aggaatgttg caacttgcaa ggaggcgttt cttttctttga atttaactaa ctcgttgagt    300
ggccctgttt ctcggacgta aggcctttgc tgctccacac atgtccattc gaattttacc    360
gtgtttagca agggcgaaaa gtttgcatct tgatgattta gcttgactat gcgattgctt    420
tcctggaccc gtgcagctgc ggtggcatgg gaggccggca agccactgtc gatcgaggag    480
gtggaggtag cgcctccgca ggccatggag gtgcgcgtca agatcctctt cacctcgctc    540
tgccacaccg acgtctactt ctgggaggcc aaggtatcta atcagccatc ccatttgtga    600
tctttgtcag tagatatgat acaacaactc gcggttgact tgcgccttct tggcggctta    660
tctgtcttag gggcagactc ccgtgttccc tcggatcttt ggccacgagg ctggagggta    720
```

<210> SEQ ID NO 14
<211> LENGTH: 36
<212> TYPE: RNA
<213> ORGANISM: Artificial Sequence
<220> FEATURE:
<223> OTHER INFORMATION: Synthetic

<400> SEQUENCE: 14
ggccucccag aaguagacgu guuuuagagc uaugcu                                36

<210> SEQ ID NO 15
<211> LENGTH: 144
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: phosphorothioate bond to residue 2
<220> FEATURE:
<221> NAME/KEY: modified_base
<222> LOCATION: (2)..(2)
<223> OTHER INFORMATION: phosphorothioate bond to residue 3
<220> FEATURE:
<221> NAME/KEY: modified_base
<222> LOCATION: (3)..(3)
<223> OTHER INFORMATION: phosphorothioate bond to residue 4
<220> FEATURE:
<221> NAME/KEY: modified_base
<222> LOCATION: (141)..(141)
<223> OTHER INFORMATION: phosphorothioate bond to residue 142
<220> FEATURE:
<221> NAME/KEY: modified_base
<222> LOCATION: (142)..(142)
<223> OTHER INFORMATION: phosphorothioate bond to residue 143
<220> FEATURE:
<221> NAME/KEY: modified_base
<222> LOCATION: (143)..(143)
<223> OTHER INFORMATION: phosphorothioate bond to residue 144

<400> SEQUENCE: 15
aggaggtgga ggtagcgcct ccgcaggcca tggaggtgcg cgtcaagatc ctcttcacct      60
cgctctggta ccccgacgtc tacttctggg aggccaaggt atctaatcag ccatcccatt     120
tgtgatcttt gtcagtagat atga                                           144

<210> SEQ ID NO 16
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: phosphorylated 5' end
<220> FEATURE:
<221> NAME/KEY: modified_base
<222> LOCATION: (1)..(1)
<223> OTHER INFORMATION: phosphorothioate bond to residue 2
<220> FEATURE:
<221> NAME/KEY: modified_base
<222> LOCATION: (2)..(2)
<223> OTHER INFORMATION: phosphorothioate bond to residue 3
<220> FEATURE:
<221> NAME/KEY: modified_base
<222> LOCATION: (32)..(32)
<223> OTHER INFORMATION: phosphorothioate bond to residue 33
<220> FEATURE:
<221> NAME/KEY: modified_base
<222> LOCATION: (33)..(33)
<223> OTHER INFORMATION: phosphorothioate bond to residue 34

```
<400> SEQUENCE: 16
gtttaattga gttgtcatat gttaataacg gtat                                34

<210> SEQ ID NO 17
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: Phosphorylated 5' end
<220> FEATURE:
<221> NAME/KEY: modified_base
<222> LOCATION: (1)..(1)
<223> OTHER INFORMATION: phosphorothioate bond to residue 2
<220> FEATURE:
<221> NAME/KEY: modified_base
<222> LOCATION: (2)..(2)
<223> OTHER INFORMATION: phosphorothioate bond to residue 3
<220> FEATURE:
<221> NAME/KEY: modified_base
<222> LOCATION: (32)..(32)
<223> OTHER INFORMATION: phosphorothioate bond to residue 33
<220> FEATURE:
<221> NAME/KEY: modified_base
<222> LOCATION: (33)..(33)
<223> OTHER INFORMATION: phosphorothioate bond to residue 34

<400> SEQUENCE: 17
ataccgttat taacatatga caactcaatt aaac                                34
```